(12) United States Patent
McBean et al.

(10) Patent No.: US 8,585,620 B2
(45) Date of Patent: Nov. 19, 2013

(54) POWERED ORTHOTIC DEVICE AND METHOD OF USING SAME

(75) Inventors: John M. McBean, Boston, MA (US); Kailas Narendran, South Burlington, VT (US)

(73) Assignee: Myomo, Inc., Cambridge, MA (US)

( * ) Notice: Subject to any disclaimer, the term of this patent is extended or adjusted under 35 U.S.C. 154(b) by 574 days.

(21) Appl. No.: 12/406,732

(22) Filed: Mar. 18, 2009

(65) Prior Publication Data
US 2009/0227925 A1 Sep. 10, 2009

Related U.S. Application Data

(63) Continuation-in-part of application No. 11/857,881, filed on Sep. 19, 2007.

(60) Provisional application No. 61/037,556, filed on Mar. 18, 2008, provisional application No. 60/826,188, filed on Sep. 19, 2006, provisional application No. 60/889,773, filed on Feb. 14, 2007.

(51) Int. Cl.
*A61H 1/00* (2006.01)
*A61F 5/00* (2006.01)

(52) U.S. Cl.
USPC .................. 601/5; 601/24; 601/33; 600/546

(58) Field of Classification Search
USPC ........ 601/5, 23, 24, 26, 33; 602/5, 16, 18, 20, 602/21; 600/546
See application file for complete search history.

(56) References Cited

U.S. PATENT DOCUMENTS

| | | | |
|---|---|---|---|
| 3,631,542 A | 1/1972 | Potter | 3/1.1 |
| 4,030,141 A | 6/1977 | Graupe | 3/1.1 |

(Continued)

FOREIGN PATENT DOCUMENTS

| | | | | |
|---|---|---|---|---|
| JP | H8687 | 1/1996 | | |
| JP | 2005253650 A | * | 9/2005 | ............... A61H 3/00 |

(Continued)

OTHER PUBLICATIONS

Abul-Haj et al., "Functional Assessment of Control Systems for Cybernetic Elbow Prostheses—Part II: Application of the Technique", 1990, IEEE Transactions on Biomedical Engineering, vol. 37, No. 11, pp. 1037-1047.

(Continued)

*Primary Examiner* — Quang D Thanh
(74) *Attorney, Agent, or Firm* — Sunstein Kann Murphy & Timbers LLP

(57) ABSTRACT

A powered orthotic system includes a wearable component having a brace with a first section and a second section. The first and second sections are coupled to each other at a pivot. Each section is adapted to be removably attached to a corresponding first and second limb segment such that the pivot is proximate to a joint between each limb segment. The first and the second sections are movable with respect to each other to define flexion and extension directions. The wearable component also includes an electromyographic sensor, an electrically powered actuator assembly in communication with the electromyographic sensor, and a controller in communication with the actuator assembly that provides system parameters to control operation of the actuator assembly. The actuator assembly is coupled to the first and the second sections so as to apply a force that moves the first and the second sections in the flexion and/or extension directions and the force is based on signals from the electromyographic sensor. The actuator assembly is positioned proximate to the pivot. The system also includes a control unit in communication with the wearable component. The control unit includes a processor that modifies the system parameters in the controller and a user interface, in communication with the processor, that permits user selection of the system parameters.

20 Claims, 33 Drawing Sheets

(56) References Cited

U.S. PATENT DOCUMENTS

| | | | | |
|---|---|---|---|---|
| 4,209,860 | A | | 7/1980 | Graupe .............................. 3/1.1 |
| 4,650,492 | A | | 3/1987 | Barkhordar et al. ............ 623/24 |
| 4,685,925 | A | | 8/1987 | Childress et al. ............... 623/25 |
| 5,112,296 | A | | 5/1992 | Beard et al. ...................... 602/28 |
| 5,282,460 | A | | 2/1994 | Boldt ........................... 128/25 R |
| 5,466,213 | A | | 11/1995 | Hogan et al. .................... 601/33 |
| 5,682,327 | A | * | 10/1997 | Telepko .......................... 601/34 |
| 5,685,830 | A | | 11/1997 | Bonutti ........................... 602/16 |
| 5,800,561 | A | | 9/1998 | Rodriguez ...................... 623/26 |
| 5,853,005 | A | | 12/1998 | Scanlon ................... 128/662.03 |
| 5,888,212 | A | | 3/1999 | Petrofsky et al. ............... 623/24 |
| 5,888,213 | A | | 3/1999 | Sears et al. ...................... 625/24 |
| 5,951,499 | A | * | 9/1999 | Saringer et al. ................. 601/33 |
| 5,954,621 | A | | 9/1999 | Joutras et al. ................. 482/114 |
| 5,980,435 | A | | 11/1999 | Joutras et al. ................. 482/114 |
| RE37,209 | E | | 6/2001 | Hensly et al. ................... 602/26 |
| 6,379,393 | B1 | | 4/2002 | Mavroidis et al. .............. 623/25 |
| 6,532,383 | B2 | | 3/2003 | Maloney et al. .............. 600/546 |
| 6,599,255 | B2 | * | 7/2003 | Zhang ............................ 600/587 |
| 6,616,579 | B1 | | 9/2003 | Reinbold et al. ................ 482/91 |
| 6,660,042 | B1 | | 12/2003 | Curcie et al. .................... 623/24 |
| 6,821,259 | B2 | | 11/2004 | Rahman et al. ................. 601/34 |
| 6,880,487 | B2 | | 4/2005 | Reinkensmeyer et al. ... 119/700 |
| 6,944,496 | B2 | | 9/2005 | Jeong et al. ................... 600/546 |
| 6,966,882 | B2 | | 11/2005 | Horst ................................ 601/5 |
| 6,969,365 | B2 | | 11/2005 | Scorvo ............................ 602/16 |
| 7,182,738 | B2 | | 2/2007 | Bonutti et al. .................... 601/5 |
| 2002/0169402 | A1 | | 11/2002 | Hatton et al. ................... 602/26 |
| 2002/0183673 | A1 | * | 12/2002 | Naft et al. ....................... 602/16 |
| 2003/0023195 | A1 | | 1/2003 | Rahman et al. ................. 601/20 |
| 2003/0064869 | A1 | | 4/2003 | Reinkensmeyer et al. ... 482/100 |
| 2003/0120183 | A1 | | 6/2003 | Simmons ...................... 600/595 |
| 2004/0106881 | A1 | * | 6/2004 | McBean et al. ................... 601/5 |
| 2005/0006980 | A1 | | 1/2005 | Horst ............................ 310/309 |
| 2006/0004307 | A1 | | 1/2006 | Horst ................................ 601/5 |
| 2006/0052731 | A1 | | 3/2006 | Shimada et al. | |
| 2006/0064044 | A1 | * | 3/2006 | Schmehl .......................... 601/34 |
| 2006/0130594 | A1 | | 6/2006 | Ikeuchi | |
| 2007/0191743 | A1 | * | 8/2007 | McBean et al. ................... 601/5 |
| 2008/0071386 | A1 | | 3/2008 | McBean et al. ................. 623/25 |
| 2008/0139968 | A1 | | 6/2008 | Endo et al. | |
| 2008/0161937 | A1 | | 7/2008 | Sankai ............................. 623/25 |
| 2008/0234608 | A1 | * | 9/2008 | Sankai .............................. 601/5 |

FOREIGN PATENT DOCUMENTS

| | | | |
|---|---|---|---|
| JP | 200687533 | | 4/2006 |
| JP | 2006167313 | | 6/2006 |
| WO | 2004107085 | A2 | 12/2004 |
| WO | 2006064657 | A1 | 6/2006 |

OTHER PUBLICATIONS

Benjuya et al., "Hybrid Arm Orthosis", 1990, American Academy of Orthotics and Prosthetics, Journal of Prosthetics & Orthotics, vol. 2, No. 2, pp. 155-163.

Bowen et al., "Surface EMG and Motor Control of the Upper Extremity in Muscular Dystrophy: A Pilot Study", 2002, IEEE Bioengineering Conf., pp. 289-290.

Brown et al., "The Exoskeleton Glove for Control of Paralyzed Hands", 1993, IEEE, 1050-4729/93, pp. 642-647.

Downes et al., "Distributed Control of an Electrically Powered Hip Orthosis", 1994, IEE Control Conference, pp. 24-30.

Fukuda et al., "EMG-Based Human-Robot Interface for Rehabilitation Aid", Proceedings of the 1998 IEEE International Conference on Robotics and Automation, pp. 3492-3497.

Harwin et al., "A Review of Design Issues in Rehabilitation Robotics with Reference to North American Research", IEEE Transactions on Rehabilitation Engineering, vol. 3, No. 1, Mar. 1995, 1063-6528/95, pp. 3-13.

Harwin et al., "Criteria for Interfacing and Control of a Powered Upper Extremity Orthosis", RERC on Rehabilitation Robotics Applied Science and Engineering Laboratories, University of Delaware/A.I. DuPont Institute, Rehabilitation R&D Progress reports, 1995, vol. 33, p. 215.

Homma et al., "An Upper Limb Motion Assist System, Experiments with Arm Models", Proceedings of the 1996 IEEE/RSJ Int'l Conference on Intelligent Robots and Systems, Victoria, B.C., Canada, Oct. 1998, 0-7803-4465-0/98, pp. 758-763.

Johnson et al., "Development of a Mobility Assist for the Paralyzed, Amputee, and Spastic Patient", 1996, IEEE; 0-7803-3131-1/96; pp. 67-70.

Kawamoto et al., "Comfortable Power Assist Control Method for Walking Aid by HAL-3", 2000, IEEE SMC, TP1B2; 6 sheets.

Kawamura et al., "A Design of Motion-Support Robots for Human Arms using Hexahedron Rubber Actuators", 1997, IROS, IEEE, pp. 1520-1526.

Kazerooni, "Stability and Performance of Robotic Systems Worn by Humans", University of Minnesota, Mechanical Engineering Dept., May 13-18, 1990 IEEE, vol. 1, pp. 558-563.

Kiguchi et al., "An Exoskeletal Robot for Human Elbow Motion Support-Sensor Fusion, Adaptation, and Control", 2001, IEEE Transactions on Systems, Man, and Cybernetics-Part B; Cybernetics, vol. 31, No. 3, Jun. 2001, 1083-4419/01, pp. 353-361.

Kiguchi et al., "An Exoskeleton System for Elbow Joint Motion Rehabilitation", Proceedings of the 2003 IEEE/ASME International Conference on Advanced Intelligent Mechatronics (AIM 2003), pp. 1228-1233.

Krebs et al., "Robot-Aided Neuro-rehabilitation in Stroke: Three-Year Follow-Up", 1999, Int'l Conference on Rehabilitation Robotics, pp. 34-41.

Krebs et al., "Increasing Productivity and Quality of Care: Robot-Aided Neuro-Rehabilitation", Journal of Rehabilitation Research and Development, vol. 37, No. 6, Nov./Dec. 2000, pp. 1-4.

Krebs et al., Robot-Aided Neurorehabilitation, 1998, IEEE Transactions on Rehabilitation Engineering vol. 6, No. 1, Mar. 1998, pp. 75-77.

Lee et al., Power Assist Control for Walking Aid with HAL-3 Based on EMG and Impedance Adjustment around Knee Joint, 2002, IEEE/RSJ Int'l Conf. on Intelligent Robots and Systems, EPFL, Lausanne, Switzerland, Oct. 2002; 2002 IEEE; 0-7803-7396-7.02 pp. 1499-1504.

Lee et al., "A New Exoskeleton-type Masterarm with Force Reflection: Controller and Integration", 1999, IEEE/RSJ International Conference on Intelligent Robots and Systems, pp. 1438-1443.

Lum et al., "A Robotic System for Upper-Limb Exercises to Promote Recovery of Motor Function Following Stroke", ICORR '99: International Conference on Rehabilitation Robotics, Stanford, CA, pp. 235-239.

Lum et al., "Quantification of Force Abnormalities During Passive and Active-Assisted Upper-Limb Reaching Movements in Post-Stroke Hemiparesis", 1999, IEEE Trans on Biomed, vol. 46, No. 6, pp. 652-662.

Lum et al., "Robotic Assist Devices for Bimanual Physical Therapy: Preliminary Experiments", 1993, IEEE Transactions on Rehabilitation Engineering, vol. 1, No. 3, pp. 185-191.

Morita et al., "Basic Study on Rehabilitation Support System for Upper Limb Motor Function", 2002, IEEE AMC, pp. 127-132.

Parsons et al., An Adaptable User Interface and Controller for a Rehabilitation Robotoc Arm, 1997, ICAR, pp. 919-923.

Popovic et al., "Hybrid Assistance System—The Motor Neuroprosthesis", 1989, IEEE Transactions on Biomedical Engineering, vol. 36, No. 7, pp. 729-737.

Rabischong et al., "Control and Command of a Six Degrees of Freedom Active Electrical Orthosis for Paraplegic Patent", 1990, IEEE International Workshop on Intelligent Robots and Systems, pp. 987-991.

Reinkensmeyer et al., "Guidance-Based Quantification of Arm Impairment Following Brain Injury: A Pilot Study", 1999, IEEE Transactions on Rehabilitation Engineering, vol. 7, No. 1, pp. 1-11.

Romilly et al., "A Functional Task Analysis and Motion Stimulation for the Development of a Powered Upper-Limb Orthosis", 1994, IEEE Transactions on Rehabilitation Engineering, vol. 2, No. 3, pp. 119-129.

(56) References Cited

OTHER PUBLICATIONS

Rosen et al., "A Myosignal-Based Powered Exoskeleton System", 2001, IEEE Transactions on System, Man, and Cybernetics, Part A: Systems and Humans, vol. 31, No. 3, pp. 210-222.

Seliktar et al., "Evaluation of Functional Capabilities of People with Muscular Dystrophy as Potential Users of Powered Orthoses", ASME Summer Bioengineering Conference, Jun. 16-20, 1999, Blue Sky Montana, 2 sheets.

Timoszyk et al., "Robot-Assisted Locomotion Training after Spinal Cord Injury: Comparison of Rodent Stepping in Virtual and Physical Treadmill Environments", Department of Mechanical and Aerospace Engineering and Center for Biomedical Engineering, University of California, Irvine, 1990 IEEE International Conference, pp. 1-14.

Triolo et al., "The Theoretical Development of a Multichannel Time-Series Myoprocessor for Simultaneous Limb Function Detection and Muscle Force Estimation", 1989, IEEE Transactions on Biomedical Engineering, vol. 36, No. 10, pp. 1004-1017.

Umetani et al., "Skil Mate", Wearable Exoskeleton Robot, 1999, IEEE, 0-7803-5131, pp. IV984 to IV988.

Wiegner et al., "Design of a Triceps Orthosis for C5/C6 Quadriplegics" 0-7803-0785, Feb. 1992, IEEE, pp. 1485-1486.

Wu et al., "A Study of Neuromuscular-like Control in Rehabilitation Robot", Proceedings of the 1996 IEEE International Conference on Rotobics and Automation, Minneapolis, MN, 0-7803-2988-4/96, Apr. 1996, pp. 1178-1183.

Zardoshti-Kermani et al., "EMG Feature Evaluation for Movement Control of Upper Extremity Prostheses", 1995, IEEE Transactions on Rehabilitation Engineering, vol. 3, No. 4, pp. 324-333.

International Searching Authority, International Search Report—International Application No. PCT/US2007/078900, dated May 20, 2008, together with the Written Opinion of the International Searching Authority, 16 pages.

Benjuya et al., "Myoelectric Hand Orthosis," Journal of Prosthetics and Orthotics, vol. 2, No. 2, pp. 149-152, 1990.

Shibata et al., "A Study on Self-Powered Ankle Foot Orthosis," Japan Society of Mechanical Engineering, No. 06-7, Dynamics and Design Conference 2006, Aug. 6-9, 2006.

* cited by examiner

CO=Command Output to actuation system
$OS_i$ =Output Signal (from particular relationship. Example: $OS_{EMGI}$).

① $CO = A(OS_{EMGI}) + B \cdot (OS_{position}) - C \cdot (OS_{elapsed\ time})$;

where A, B, C are constants.

② $CO = S_{in}(OS_{position}) + \dfrac{(OS_{EMGI})^2}{2} - OS_{current}$

③ If $OS_{time} \leq D$, then $CO = E \cdot OS_{EMGI}$

If $OS_{time} > D$, then $CO = E \cdot OS_{EMGI} - F \cdot OS_{time}$;

where D, E, F are constants.

④ If $OS_{EMGI} \leq G$, and $OS_{temp} \leq H$, and $|OS_{position}| \leq I$, then $CO = OS_{EMGI}$ ELSE, $CO = \emptyset$;
where G, H, I are constants.

*FIG. 20*

OS $_{position}$ = Output Signal (position) (From Figure 25)
OS $_{temperature}$ = Output Signal (temperature) (From Figure 26)
OS $_{EMGI}$ = Output Signal (EMGI) (From Figure 24)

If OS $_{position}$ ≤ E and OS $_{temperature}$ ≤ G,
    then CO = OS $_{EMGI}$
ELSE CO=0

|   | 1 | 2 | 3 |
|---|---|---|---|
| 3 | Increment Flexion Assistance Level | Decrement Extension Assistance Level | Decrement Extension Assistance Level |
| 2 | Increment Flexion Assistance Level | Increment Flexion Assistance Level | Decrement Extension Assistance Level |
| 1 | Increment Flexion Assistance Level | Increment Flexion Assistance Level | N/A |

Current Extension Assistance Level (rows) / Current Flexion Assistance Level (columns)

Adjustments to Flexion and Extension Assistance Levels For "One-Touch" Increase to Flexion Assistance Level, Based on Current Assistance Levels

*FIG. 35*

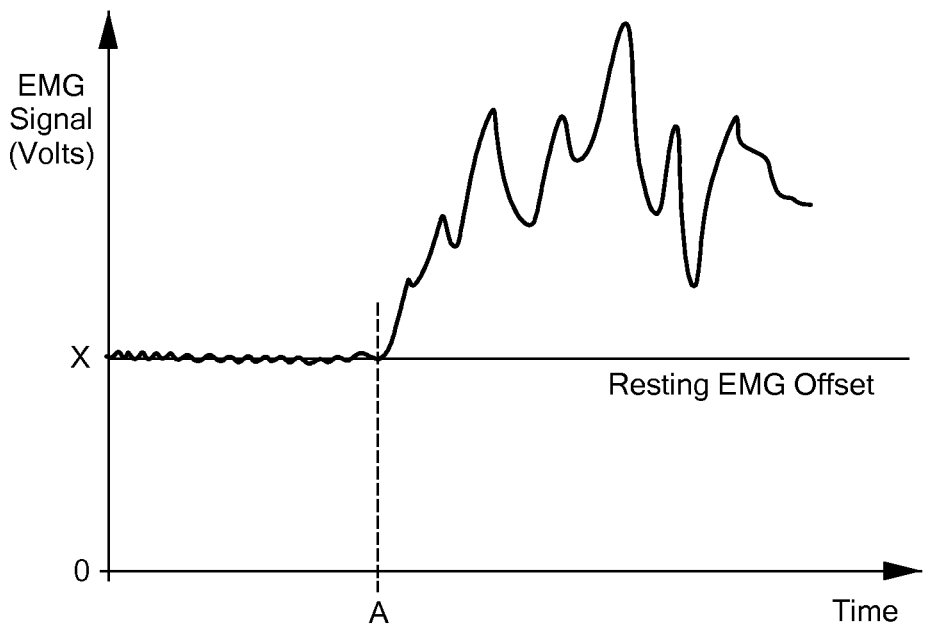

*FIG. 36*

POWERED ORTHOTIC DEVICE AND METHOD OF USING SAME

CROSS-REFERENCE TO RELATED APPLICATIONS

This patent application claims priority to U.S. Provisional Patent Application No. 61/037,556 filed Mar. 18, 2008, and is a continuation-in-part application of U.S. patent application Ser. No. 11/857,881 filed Sep. 19, 2007, which claims priority to U.S. Provisional Patent Application No. 60/826,188 filed Sep. 19, 2006 and U.S. Provisional Patent Application No. 60/889,773 filed Feb. 14, 2007, the disclosures of which are incorporated by reference herein in their entirety.

FIELD OF THE INVENTION

The invention generally relates to orthotic devices and, more particularly, the invention relates to powered orthotic devices and methods of using same for rehabilitation or functional aids.

BACKGROUND OF THE INVENTION

Stroke, brain injury, and other neuromuscular trauma survivors are often left with hemipareisis, or severe weakness in certain parts of the body. The result can be impaired or lost function in one or more limbs. It has been shown that people can rehabilitate significantly from many of the impairments following such neurological traumas. Further, it has been shown that rehabilitation is much more effective, and motor patterns re-learned more quickly, if the rehabilitative exercise regime includes the execution of familiar and functional tasks. Following neuromuscular trauma, however, the control or strength in the afflicted limb or limbs may be so severely diminished that the patient may have difficulty (or be unable) performing constructive, functional rehabilitation exercises without assistance.

SUMMARY OF THE INVENTION

In accordance with one embodiment of the invention, a powered orthotic system includes a wearable component having a brace with a first section and a second section. The first and second sections are coupled to each other at a pivot. Each section is adapted to be removably attached to a corresponding first and second limb segment such that the pivot is proximate to a joint between each limb segment. The first and the second sections are movable with respect to each other to define flexion and extension directions. The wearable component also includes an electromyographic sensor, an electrically powered actuator assembly in communication with the electromyographic sensor, and a controller in communication with the actuator assembly that provides system parameters to control operation of the actuator assembly. The actuator assembly is coupled to the first and the second sections so as to apply a force that moves the first and the second sections in the flexion and/or extension directions and the force is based on signals from the electromyographic sensor. The actuator assembly is positioned proximate to the pivot. The system also includes a control unit in communication with the wearable component. The control unit includes a processor that modifies the system parameters in the controller and a user interface, in communication with the processor, that permits user selection of the system parameters.

In related embodiments, the wearable component may further include a user interface, in communication with the controller, that permits user selection of operational modes of the wearable component. The wearable component's user interface may allow for a single input that causes a plurality of system parameters to be modified in the controller. The wearable component may further include a battery coupled to the electrically powered actuator assembly. The control unit and the wearable component may be in wireless communication with each other. The system may further include one or more additional wearable components, each additional wearable component in communication with the control unit. The system may further include one or more additional control units, each additional control unit in communication with one or more of the wearable components. The wearable component may further include memory, coupled to the controller, that stores the system parameters. The control unit may be removably attachable to the wearable component. The wearable component may further include a plurality of electromyographic sensors. The control unit may include an auto-calibration mode in which an initial electromyographic signal level is measured for one or more muscles of a user when the muscles are at-rest. The initial electromyographic signal level may be used to adjust a electromyographic signal level measured during subsequent operation of the wearable component. The control unit may include an auto-calibration mode in which a user-specific force profile is determined automatically by moving the first section relative to the second section in a desired direction to achieve a desired range of motion of the first limb segment relative to the second limb segment. The controller may include a force profile override in order to accept manual adjustment of a user-specific force profile. The wearable component may further include a user interface, in communication with the controller, for invoking the override and providing manual adjustment of the user-specific force profile. The controller may include a limb-lock mode in which the first and the second sections are locked into position relative to one another in response to a user command. The user command may be a muscle movement that is detected by the sensor, a verbal command, and/or a tactile command.

In accordance with another embodiment of the invention, an improved electrically powered orthotic device of the type having a brace with first and second sections that can be coupled respectively to first and second limb segments moveable with respect to a joint, so as to apply a force, through the sections, about the joint is disclosed. The improved device includes a wearable component containing all components necessary for normal operation of the device including an electric actuator coupled to the brace to cause application of the force, a controller in communication with the electric actuator, a sensor, and a communication port. The device also includes a control unit including user interface, a processor coupled to the user interface, memory, and a communication port. The control unit can be placed in communication with the component, via the communication port of the control unit and the communication port of the component, in order to modify parameters of the controller.

BRIEF DESCRIPTION OF THE DRAWINGS

The foregoing features of the invention will be more readily understood by reference to the following detailed description, taken with reference to the accompanying drawings, in which:

FIG. 20 shows an illustrative control algorithm according to illustrative embodiments of the present invention;

FIG. 35 shows a chart illustrating how a "one-touch" adjustment to increase flexion assistance might also result in changes to the extension assistance level.

FIG. 36 shows an example of an EMG signal trace that might be observed during calibration and use of the device.

DESCRIPTION OF ILLUSTRATIVE EMBODIMENTS

Figure 1:
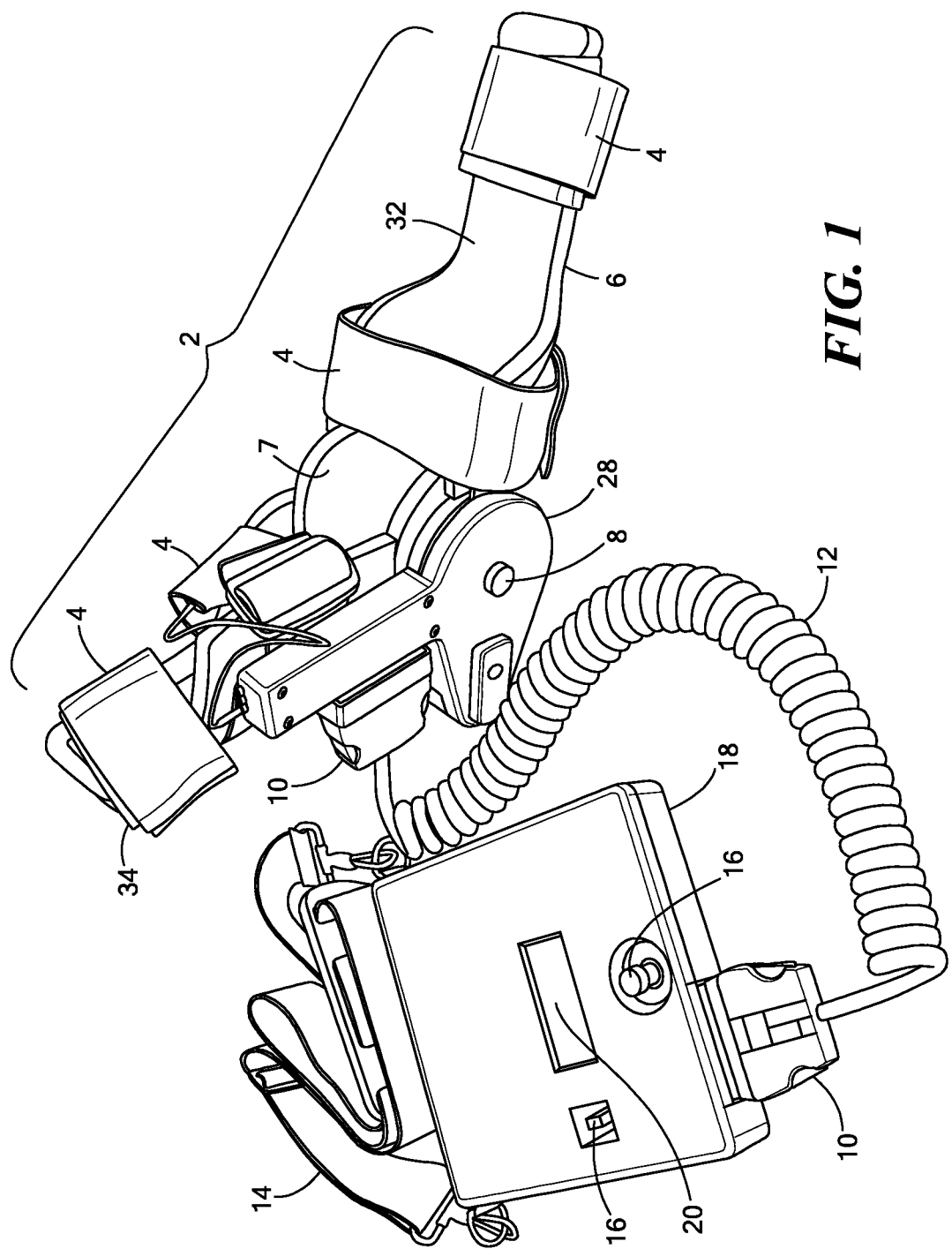
FIG. 1 shows a powered orthotic device according to illustrative embodiments of the present invention.

Definitions. As used in this description and the accompanying claims, the following terms shall have the meanings indicated, unless the context otherwise requires:

An "orthotic device" is a support or brace for weak or ineffective joints or muscles. An orthotic device is worn over existing body parts.

An "EMG-controlled" orthotic device is an orthotic device that is designed to cause the application of force to a body part with respect to a joint, at least under some conditions in response to a sensed EMG signal, so as to assist in causing motion of the body part relative to the joint. An "EMG-controlled" orthotic device includes, but is not limited to, a device (called herein an "asymmetric EMG-controlled device") that provides (i) in response to a first sensed EMG signal, a first force in a first direction and (ii) in response to one or more conditions selected from the group consisting of (a) absence of any sensed EMG signal, (b) the first sensed EMG signal, and (c) a second sensed EMG signal, a second force in a second direction that is opposed to the first direction, wherein the first force as a function of the first sensed EMG signal is asymmetric in relation to the second force in the second direction.

A "prosthesis" is an artificial device to replace a missing part of the body.

A "rehabilitation aid" is a device or treatment whose purpose is to restore function in a weak, damaged, or unhealthy body part. The purpose of a rehabilitation aid is to assist in the return of function to the body part itself, rather than compensating for or replacing that body part.

A "functional aid" is a device that serves to enhance a user's functional capacity. A functional aid does not necessarily provide rehabilitative benefit to the user, rather it serves as an assistive tool whose benefits are only realized while the tool is being used.

"User" is defined by context and refers to anyone who is interacting with the device at the moment. For example, user includes the patient or wearer of the device while the device is functioning, and a clinician, trained professional, or anyone else who is interacting with the device at the moment via the user interface.

A "plane" defined "by motion of limb segments relative to one another" is one that runs through the joint with respect to which the limb segments move and is swept through by the central axes of the limb segments as they move in flexion and extension directions. Although the motion of the limb segments may not define an exact plane, the plane is that plane which most closely approximates the surface swept by the limb segments.

"Normal operation" is a mode of operation of the device in which it is providing functional, rehabilitative, or therapeutic assistance to the wearer. "Normal operation" of a device need not inherently preclude (but could be arranged by the designer to preclude) the possibility that the wearer or another person may be able to adjust system parameters or other device settings that control operation of the device. Other modes of operation include set-up, calibration, diagnostic, and, for fine-tuning of parameters, feedback sessions.

Embodiments of the present invention provide a portable, wearable powered orthotic device and method of using same which enhances the wearer's functional capacity while it is being worn. Embodiments of the device may be used as a rehabilitation aid or a functional aid to enhance the user's functional capacity so that he or she may be able to perform the tasks and exercises that will promote further motor pattern re-learning and rehabilitation. The device is worn by the user and may apply assistive torques and forces to the user's body according to the intended motion of the user, as measured and processed by the device. As such, the device assists the user in achieving the motion patterns that he or she initiates and controls.

Often in certain neuromuscular conditions, such as stroke, a person is capable of only asymmetric control of a particular joint. For example, the person may have the ability to flex or extend the joint, but may not be able to perform both functions. In this case, the muscle group that controls flexion about the joint may be controllable by the user and its activity may be readable with the appropriate sensors, while the user's ability to control the muscle group responsible for extension about the joint may be impaired. Similarly, the opposite may be true, e.g., the user has control in the extension direction, but not the flexion direction.

Cases of asymmetric control, such as the one described above, may necessitate a device with a corresponding asymmetric control algorithm that may be controlled by the user, offering enhanced functional performance and motor pattern reinforcement to help with rehabilitation and retraining. For the purposes of rehabilitation and motor pattern re-learning, the motion of the device should accurately represent the user's intent, so that the device can re-teach and reinforce naturally learned motor patterns. For example, part of a reaching task involves relaxing the flexors (biceps, brachioradialis) and learning to let the tension in the extensors (triceps) dominate and extend the arm. Such a task would clearly be difficult for a person with an inability to apply tension with his or her triceps. The proposed control algorithm achieves and reinforces a natural reaching pattern for such a person by applying a torque that mimics the torque applied by the extensors, based solely on the relaxation state of the flexors, and in some cases other non-muscular sensory inputs.

Embodiments of the present invention may use an asymmetric control algorithm that mimics, in real time, the natural patterns of motion and force about a joint, even in the absence of the user's ability to control one of the major muscle groups (flexors or extensors) that control force and motion about the joint. Without measuring, interpreting, or processing a signal as an indicator of user intent in the second direction (the compromised direction—either flexion or extension), the device may apply torque in real-time that is directly based on the EMG signals of only the muscle group that controls motion in the first direction (the uncompromised direction). The details of this asymmetric control algorithm are described in more detail below.

FIG. 1 shows a powered orthotic device according to an embodiment of the present invention. The device includes a wearable component 2 secured to a limb or body part, the wearable component 2 in communication with a control system 18 which may be used to set or control some of the parameters of the device. Connection to the control system 18 may be via a flexible, compliant cable 12, as shown, so as to minimize impact on the mobility of the user. The cable 12 may have quick disconnect cable connectors 10 at its ends, so that it may be quickly and easily connected or disconnected from the wearable component 2 or the control system 18. This facilitates donning and doffing of the device, as the wearable component 2 may be secured to a limb of the user first, and then the cable 12 may be subsequently connected. Although a cable 12 is shown, the wearable component 2 may be in communication with the control system 18 via other interface devices. For example, the wearable component 2 may be capable of wireless communication (implemented with wireless techniques, e.g., microwave, infrared, radio frequency or other transmission techniques) with the control system 18. The wearable component 2 may also be in communication with other external power supplies, electronics, controllers, actuators, etc., whether located on or in the control system or elsewhere. The control system 18 may be worn or carried by the user or may be remotely located, such as sitting stationary on a table.

Referring also to FIGS. 2-13, the wearable component 2 includes a brace 7 which may have a first section 32 and a second section 34 operatively coupled at a pivot 8. The brace 7 may include more than two sections, and the two or more sections may be disposed parallel to each other or in series with one another. For example, one or more sections may be placed on the fingers and/or along one finger. The wearable component 2 also includes at least one set of straps 4 that removably attach each section 32, 34 to a corresponding limb segment (e.g., the first section 32 to a first limb segment and the second section 34 to a second limb segment) such that the pivot 8 is placed near to a joint between each limb segment and is aligned with the axis of rotation of the joint. For example, with an elbow brace, the first section 32 may be removably attached to the upper arm and the second section 34 may be removably attached to the lower arm. The sections 32, 34 provide coupling to the portions of the limb both above and below the joint, and the straps 4 hold the brace 7 in place around the limb and joint. The straps 4 may be soft, pliable elastic straps or stiffer inelastic straps. Preferably, the straps 4 near the joint or pivot 8 are soft and elastic to protect the skin from abrasion since these straps tend to bunch up when the device is in operation. Similarly, the stiffer, more inelastic straps are preferably used at positions away from the joint to provide rigid coupling and reliable torque application to the limb sections. The straps 4 may be made of a metal, a fabric, a plastic or a combination thereof. In one embodiment, the straps 4 may include one or more webs of material, one or more laces, an adhesive and/or a coupling mechanism that may secure the brace 7 to the user's limb or body part instead of, or in addition to, the straps 4 as shown. For example, the brace 7 may be secured in place with clamps, suction or an enclosure that encircles the user's limb and then is tightened or ratcheted in to place.

Figure 4:
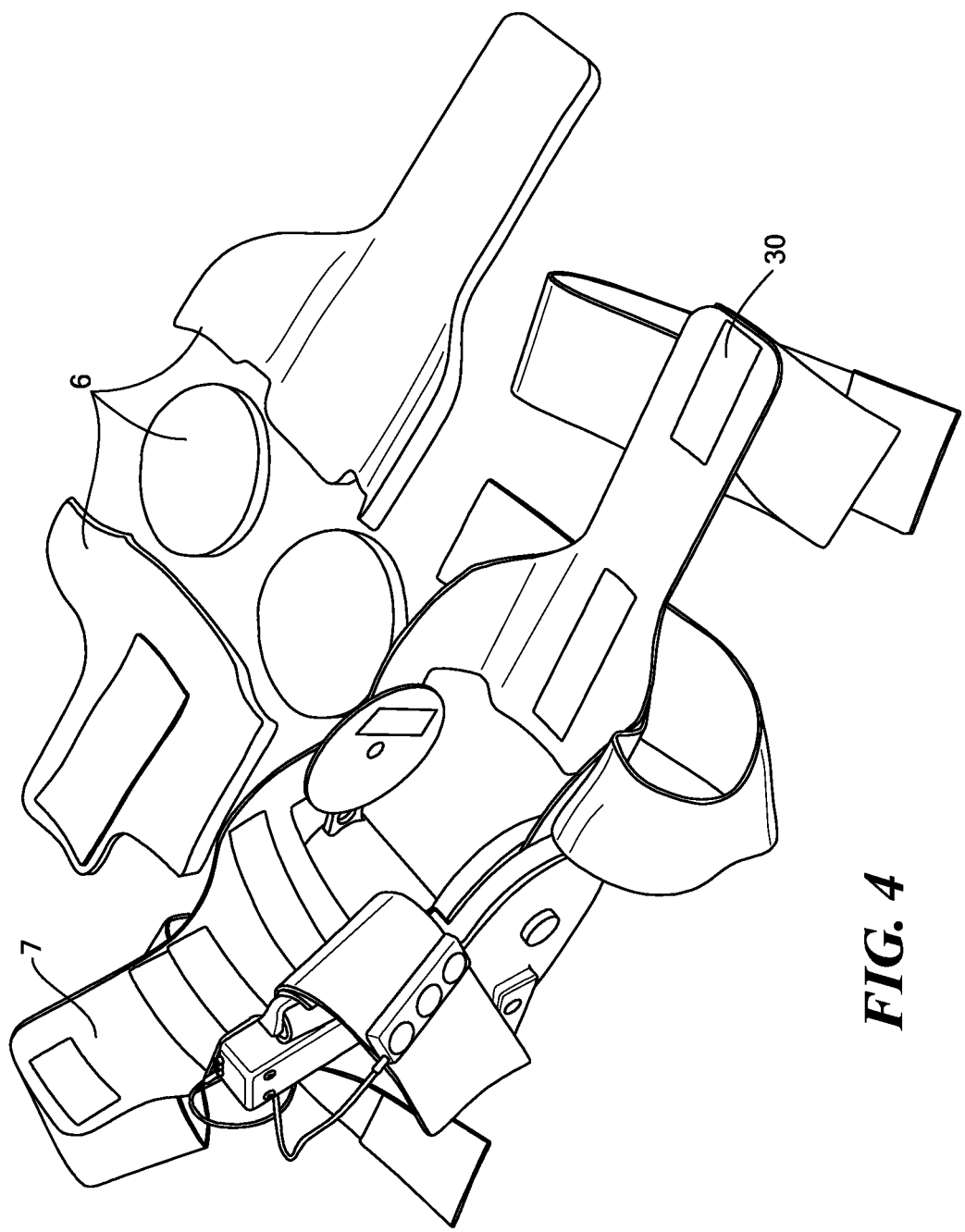
FIG. 4 shows the wearable component with padding removed according to illustrative embodiments of the present invention.
Figure 5:
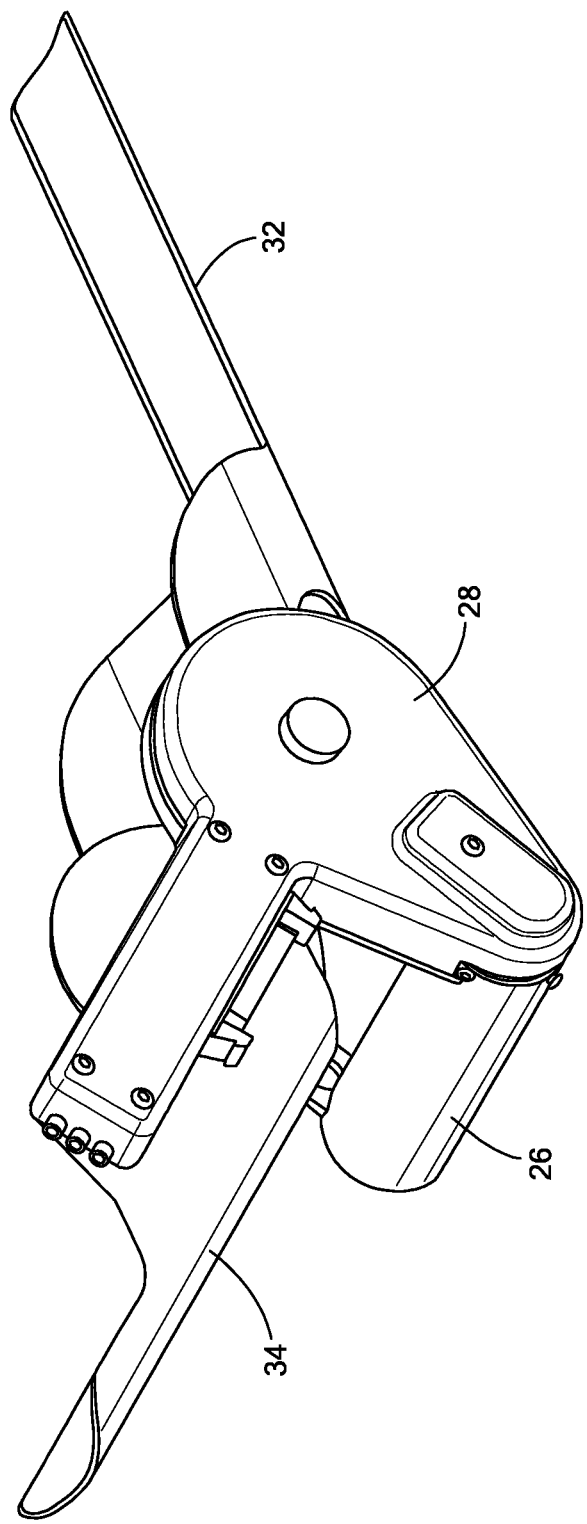
FIG. 5 shows a schematic view of the wearable component according to illustrative embodiments of the present invention.
Figure 6:
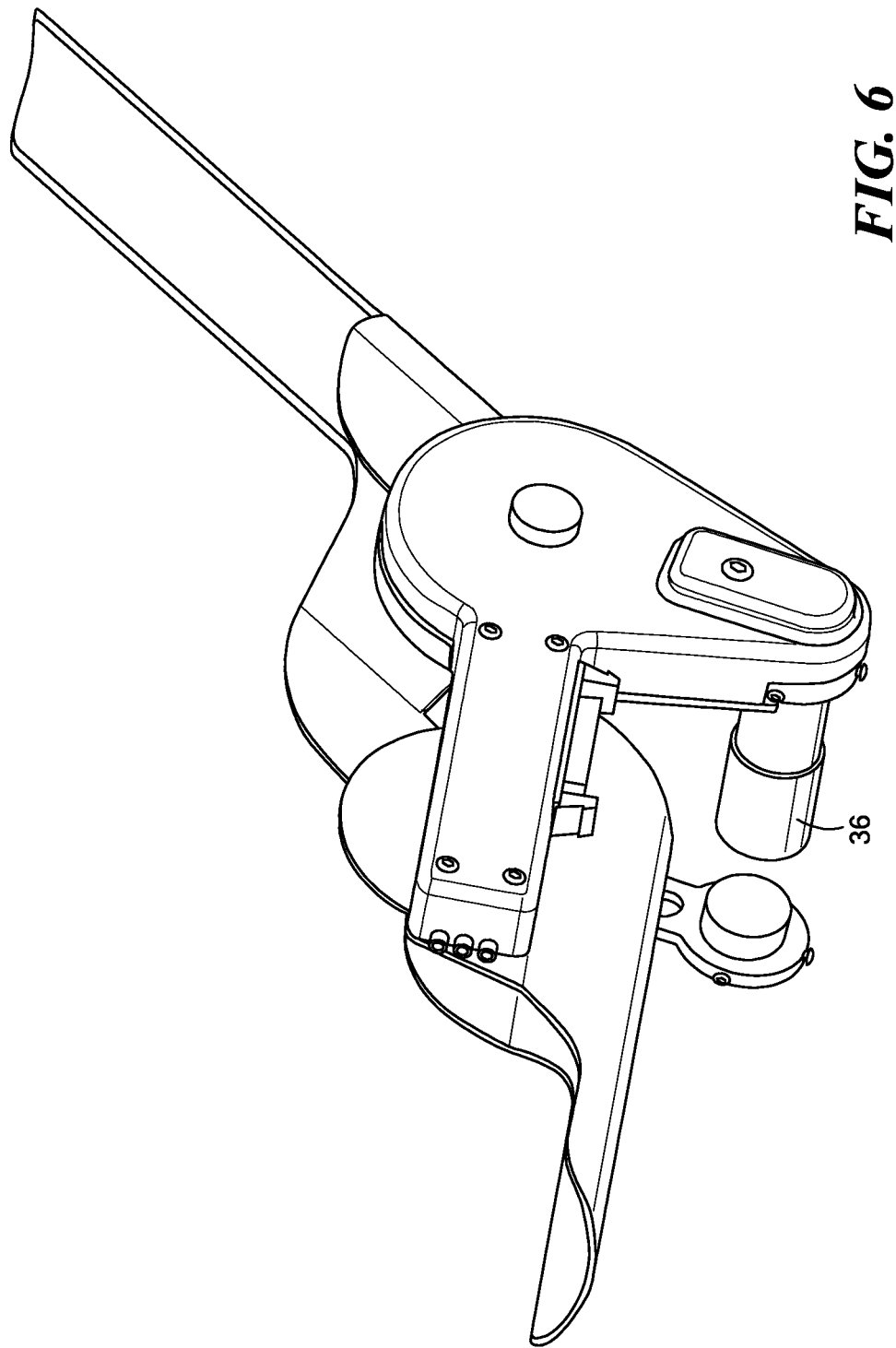
FIG. 6 shows a schematic view of the wearable component with motor housing removed according to illustrative embodiments of the present invention.

The brace 7 may also include padding 6, which may be removably coupled to the two sections 32, 34 and the pivot 8, as shown in FIG. 4. For example, the padding 6 may be coupled to the sections 32, 34 or the pivot 8 using hook and loop fasteners 30. The padding 6 may be interchangeable and have various thicknesses in order to adjust the size of the brace, e.g., thicker pads may be used to accommodate smaller arms or limbs. The padding 6 may also be removed in order to clean the padding 6 after use of the device.

Figure 2:
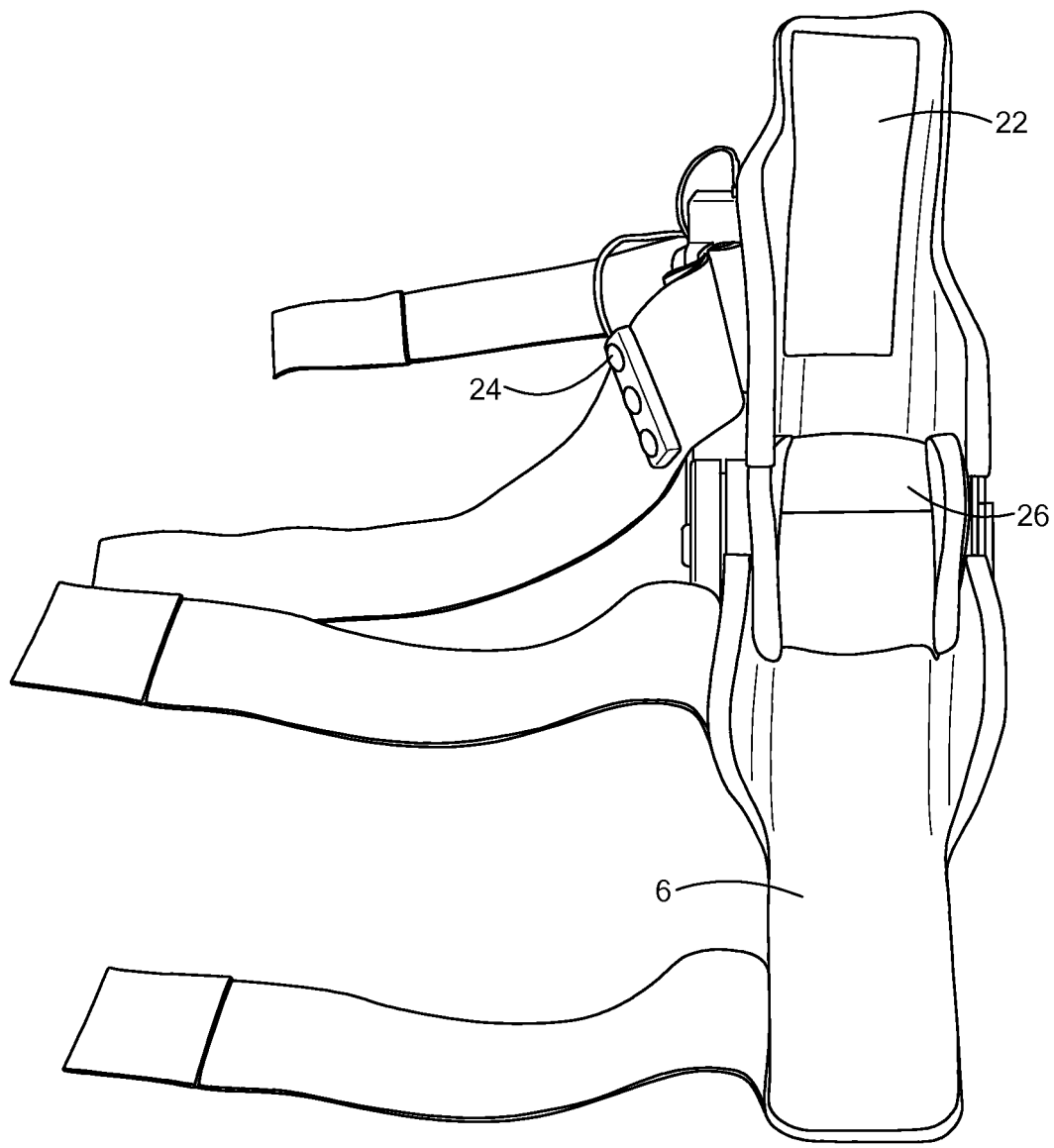
FIG. 2 shows a wearable component of the powered orthotic device for an arm according to illustrative embodiments of the present invention.

The wearable component 2 also includes a sensing system having sensors 24 that measure electromyographic (EMG) signals from a user's muscles. For example, the EMG sensors 24 may be placed in contact with the user's skin and/or may be embedded under the user's skin near to the muscles of interest. The sensing system may also contain sensors in or on both the wearable component 2 and the control system 18. Thus, the sensing system may sense other signals from a user. For example, the sensing system may sense EMG signals from a least one muscle group, and may sense other signals, such as position, velocity, force, torque, time, temperature, current, pulse, blood pressure, etc. In order to assure reliable sensor coupling to the skin, the sensors 24 may be held against the skin in a compliant way. Thus, the electromyographic sensors 24 may be coupled to one or more of the straps 4, as shown in FIG. 2, or may be coupled to one or both of the sections 32, 34. Although EMG sensors are mentioned throughout the application, sensors sensing EEG signals may be used instead of, or in addition to, the EMG sensors 24.

Figure 3:
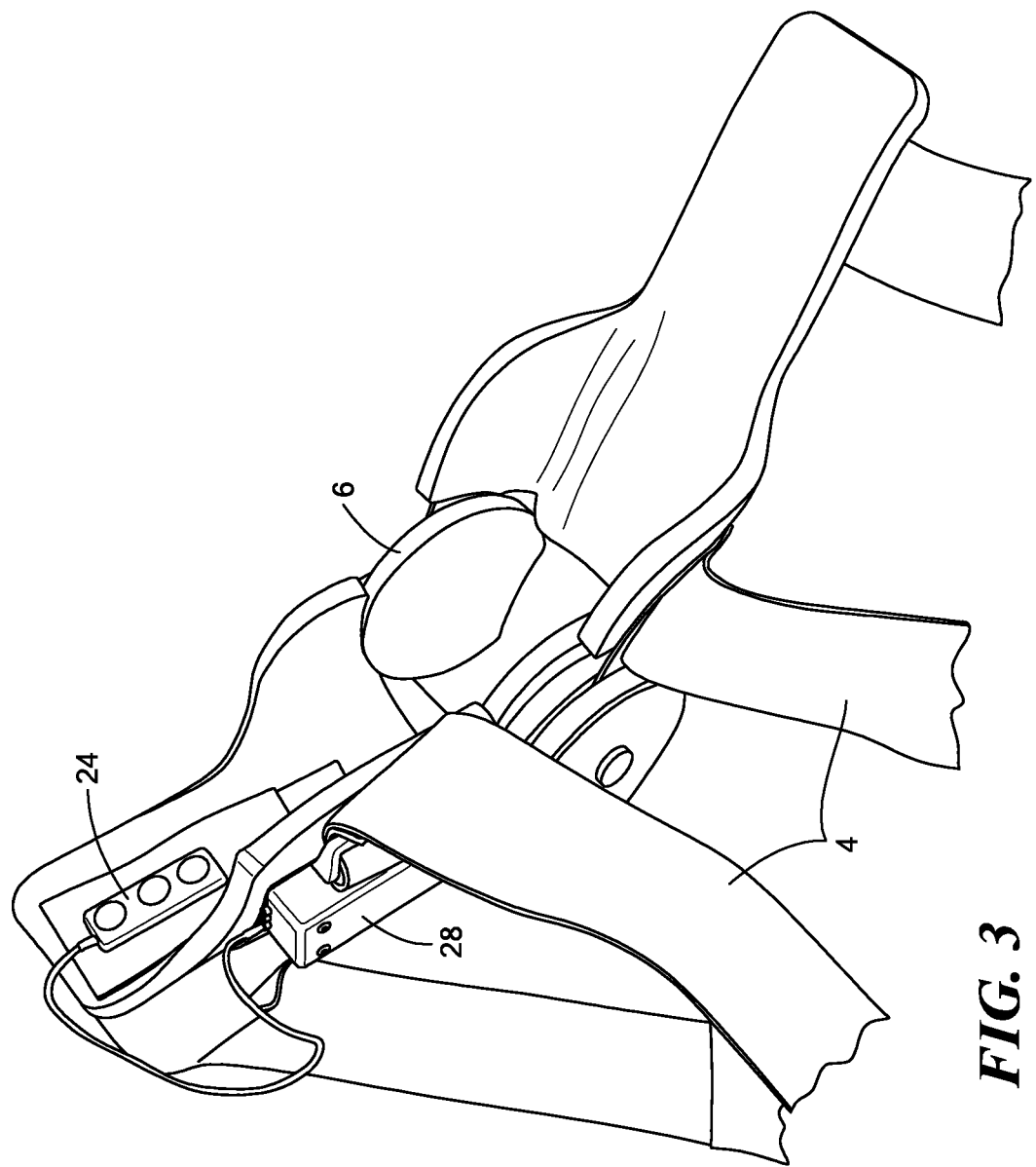
FIG. 3 shows the wearable component with sensors in position according to illustrative embodiments of the present invention.

If the padding 6 is used, then the sensors 24 may be coupled to a compliant padding element 22 coupled to the sections 32, 34, as shown in FIG. 3. Flexible EMG sensors or electrodes 24 may be used to ensure constant contact of the sensors 24 against the user's skin. Compliance, flexibility, and elasticity may be designed into the sensors 24, which may include a sensor housing, such that the sensors 24 may move as the skin moves and not lose contact with the skin's surface. For example, an elastic, compliant spring-like material or structure, e.g., made of metal, plastic, foam, fabric, rubber or any combination thereof, may be applied to the back of the sensors 24. The compliant structure may allow the sensor to be held in place with an inelastic strap, while the inherent compliance and elasticity in the sensor mount enable the sensor to maintain pressure against the skin's surface despite motion and distortion of the surface of the skin, the strap, and/or the brace. Alternatively, or in addition, the sensors 24 may be placed in recessed pockets in the strap 4. The recessions in the strap may enable reliable, repeatable sensor placement, while keeping sensor pressure low but consistent. The sensor strap may be worn under the brace 7, or may be integrated into the brace 7.

As shown in more detail in FIGS. 5-13, the wearable component 2 may further include an actuator assembly for applying torques and forces to the brace 7. The actuator assembly may include a motor and a gearhead 36 in a housing 26, the housing 26 disposed near to the pivot 8 and coupled to the first and second sections 32, 34 of the brace 7. As shown, the housing 26 may be located beneath the user's elbow, providing a protective shell to the motor and gearhead and allowing the wearable component 2 to be place on a table top or hard surface without the elbow contacting the table, thus reducing the risk of pain or injury to the user. The motor may be parallel to and co-axial with an axis of rotation of the joint or may be parallel to, but not co-axial with the axis. Alternatively, the motor may be perpendicular to the axis of rotation of the joint.

Figure 7:
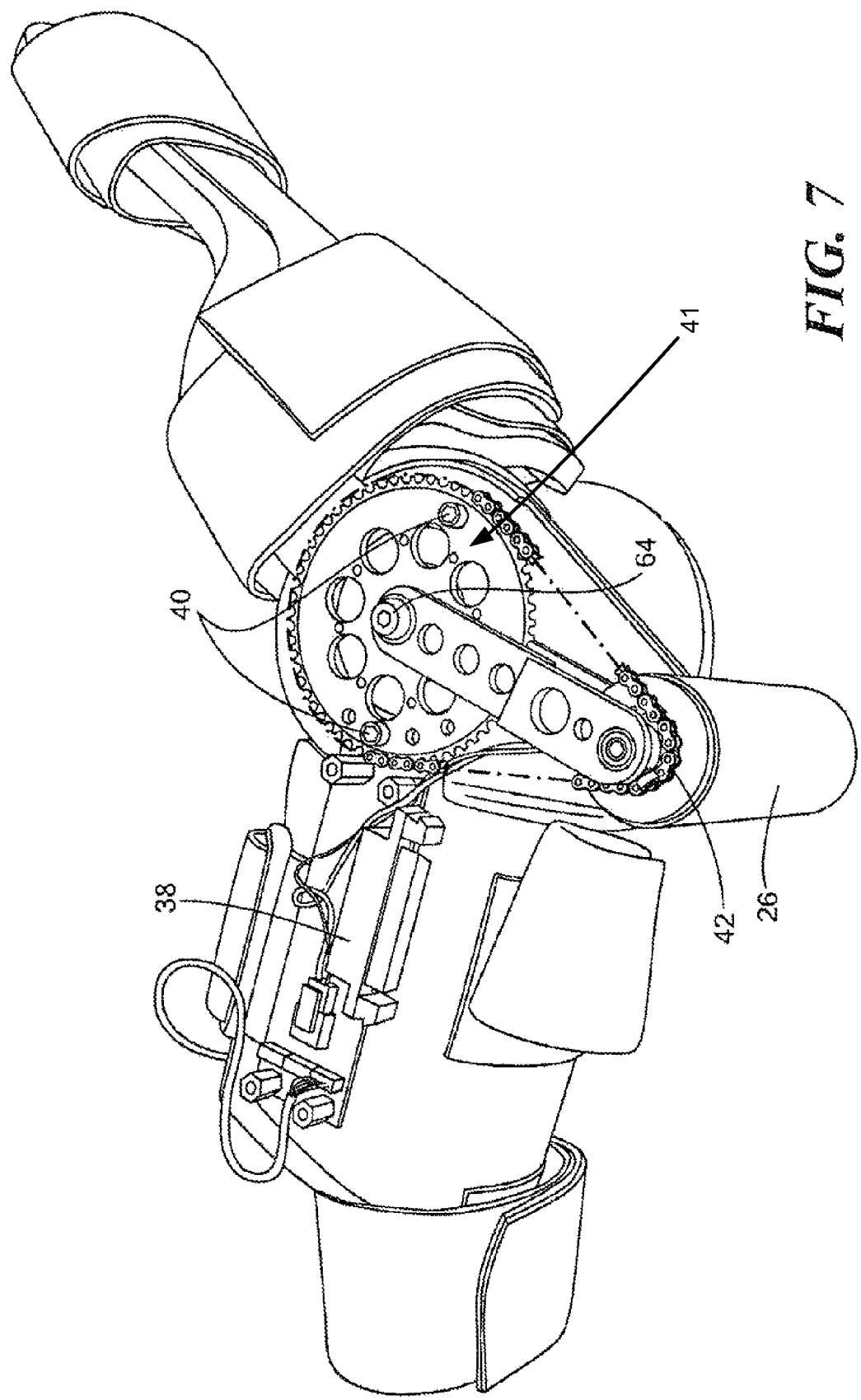
FIG. 7 shows the wearable component with plastic cover removed according to illustrative embodiments of the present invention.
Figure 8:
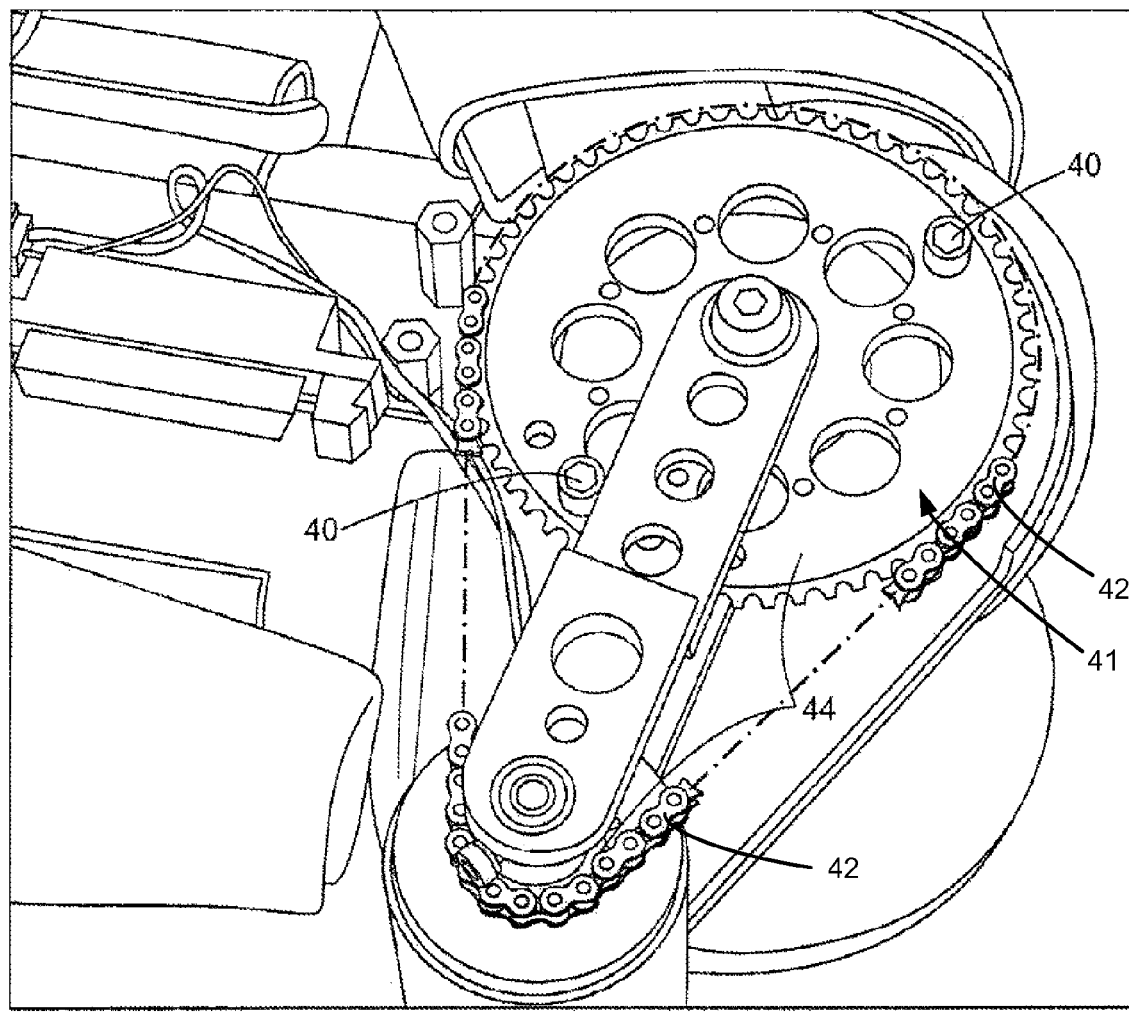
FIG. 8 shows the wearable component with drive train exposed according to illustrative embodiments of the present invention.
Figure 9:
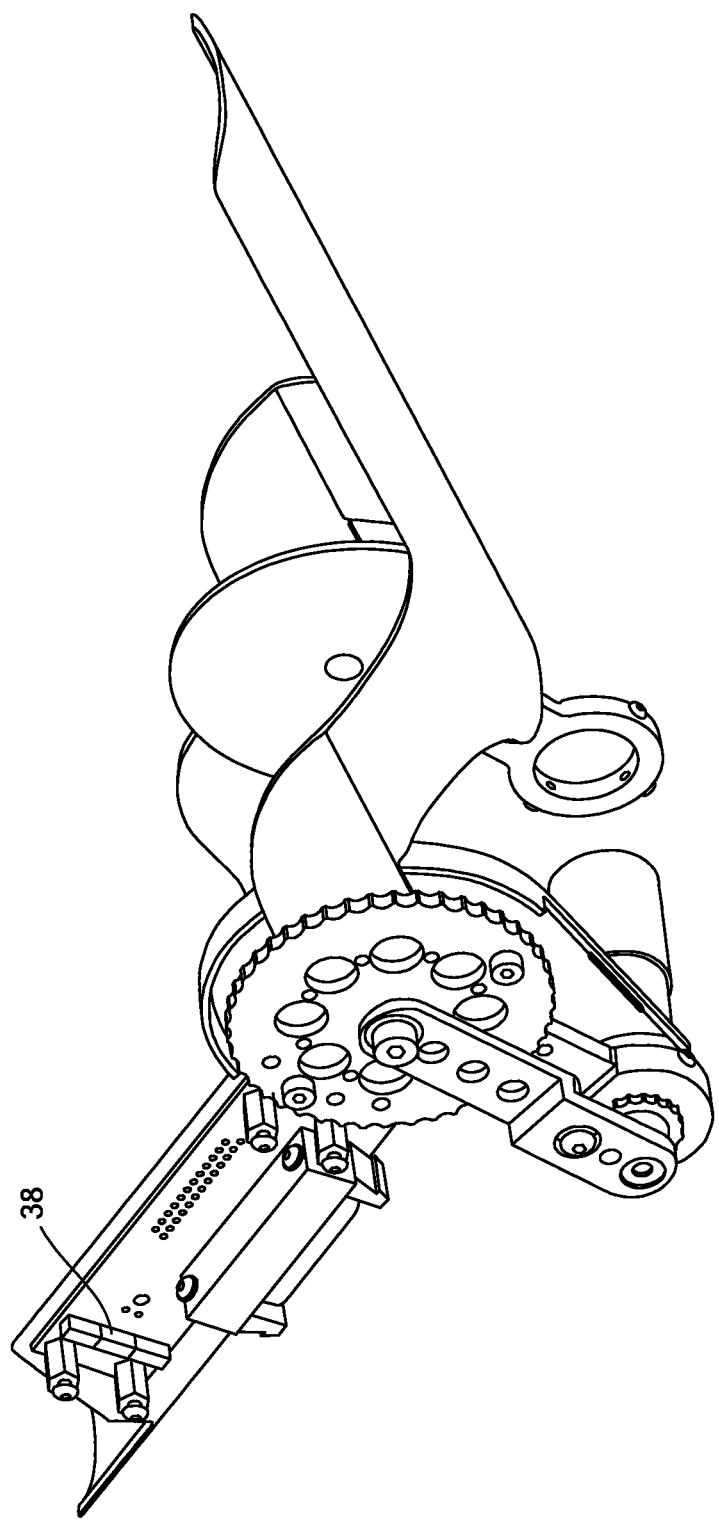
FIG. 9 shows a schematic view of the wearable component with the motor housing and the plastic cover removed according to illustrative embodiments of the present invention.
Figure 10:
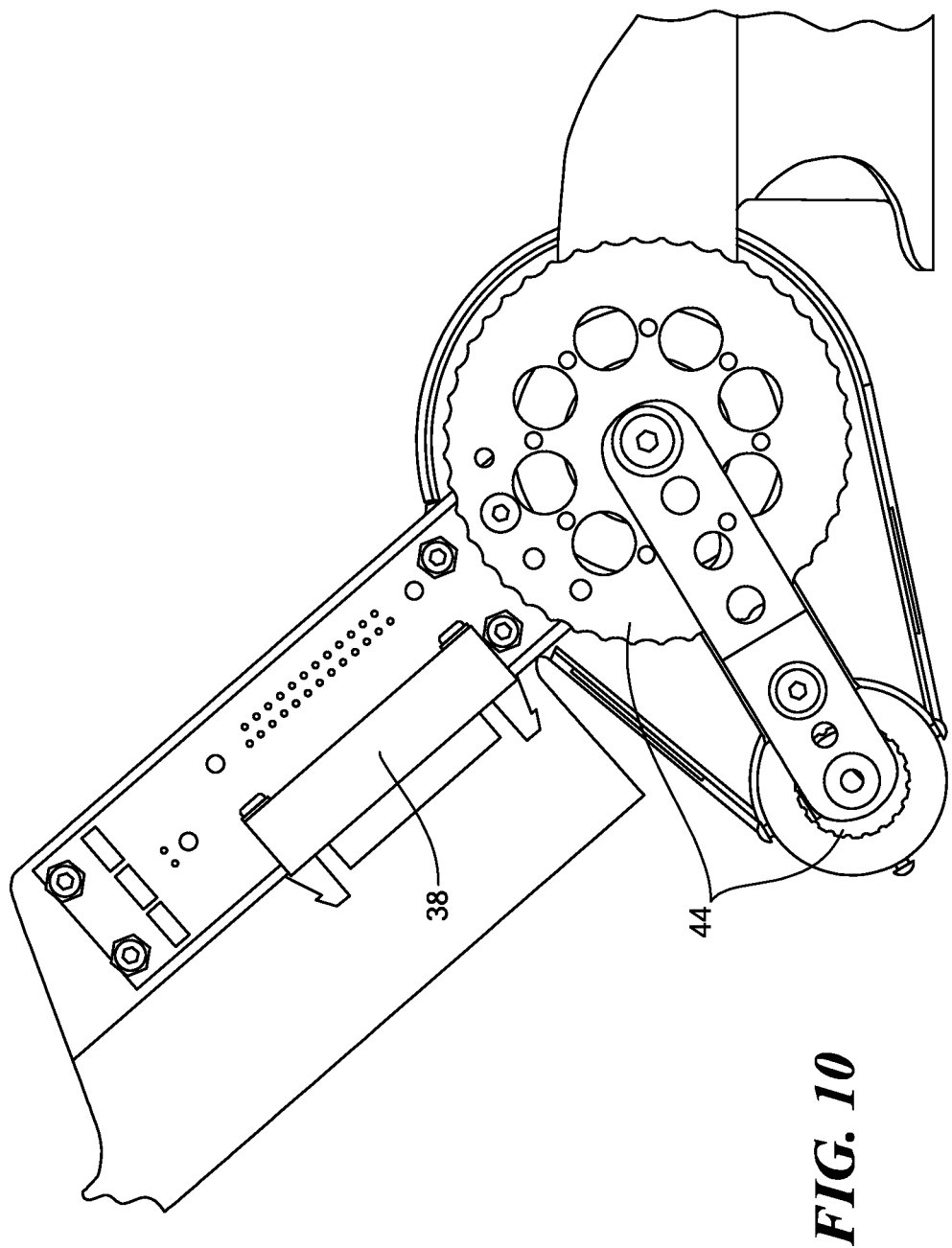
FIG. 10 shows a schematic view of the wearable component with the plastic cover removed according to illustrative embodiments of the present invention.
Figure 11:
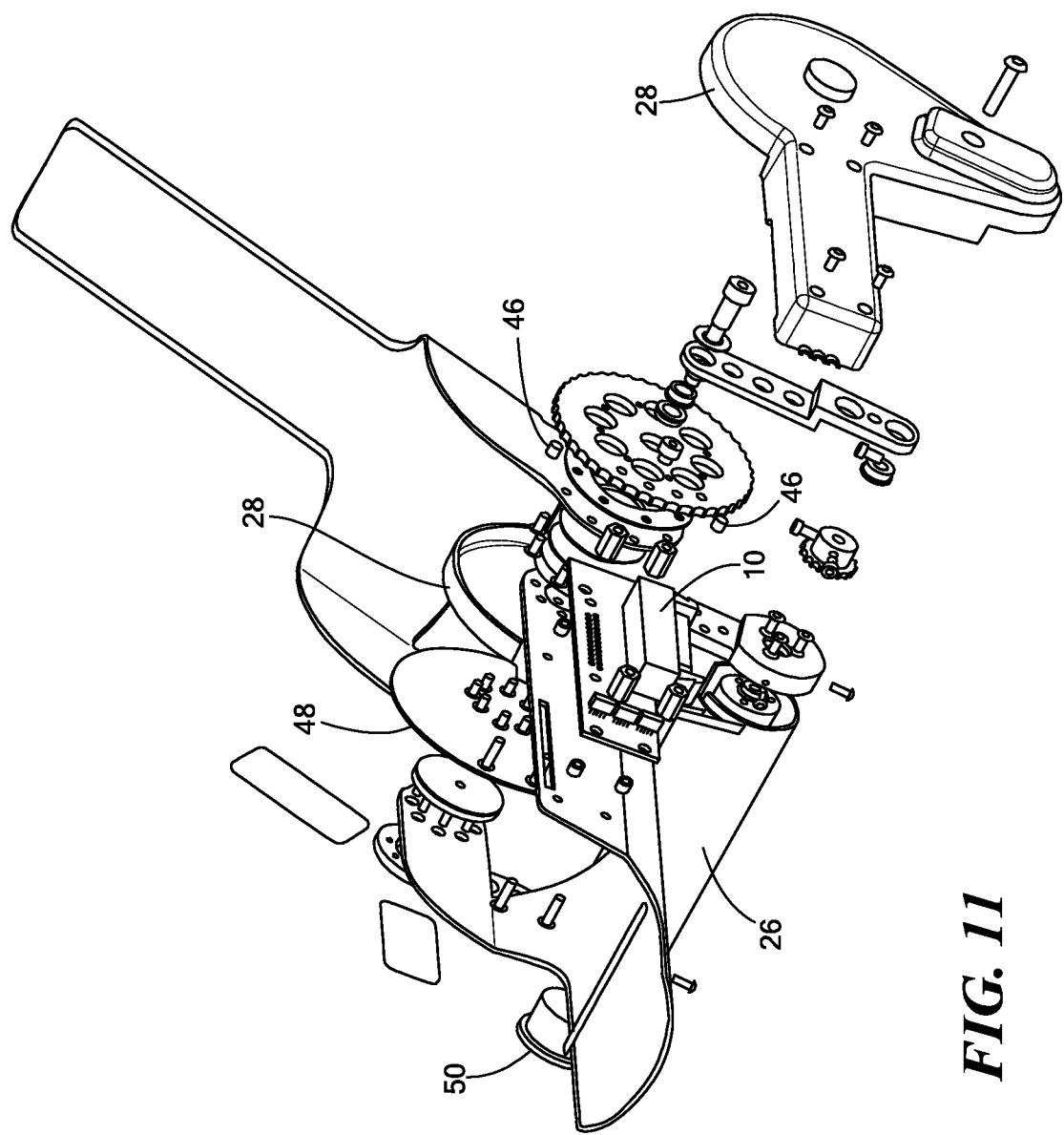
FIG. 11 shows an exploded view of the wearable component according to illustrative embodiments of the present invention.

The actuator assembly also may include a drive assembly, identified generally as item 41 in FIGS. 7 and 8, which here is implemented by tensile member 42 and corresponding tensile member drive mechanisms 44 of FIGS. 8 and 10. The tensile member 42 may be a structure such as a chain, cable, cord, or belt, and each tensile member drive mechanism 44 may be a sprocket, gear, pulley, or similar rotating mechanism.

The drive assembly 41 is coupled to the motor and gearhead 36 and coupled to the sections 32, 34 of the brace 7 at locations proximate to the pivot 8 so as to apply a force for driving the sections 32, 34 about the pivot 8. The force may be based on the EMG signals from the sensors 24, on preset values or parameters stored in the control system 18, on other inputs, or a combination thereof. Plastic covers 28 may be used to surround the components of the drive assembly 42, 44 to protect the user and others, and also to protect the drive assembly 41 components from foreign objects. Similarly, water proof or resistant, dirt, dust and/or electromagnetic radiation enclosures may be used to surround the electrical and/or mechanical components of the device to protect the device from the environment. The actuator assembly is preferably located in an unobtrusive location to increase wearer comfort and mobility, e.g., on the side of the brace away from the user's body so that it will not abrade the user's body when the device is in use.

Figure 12:
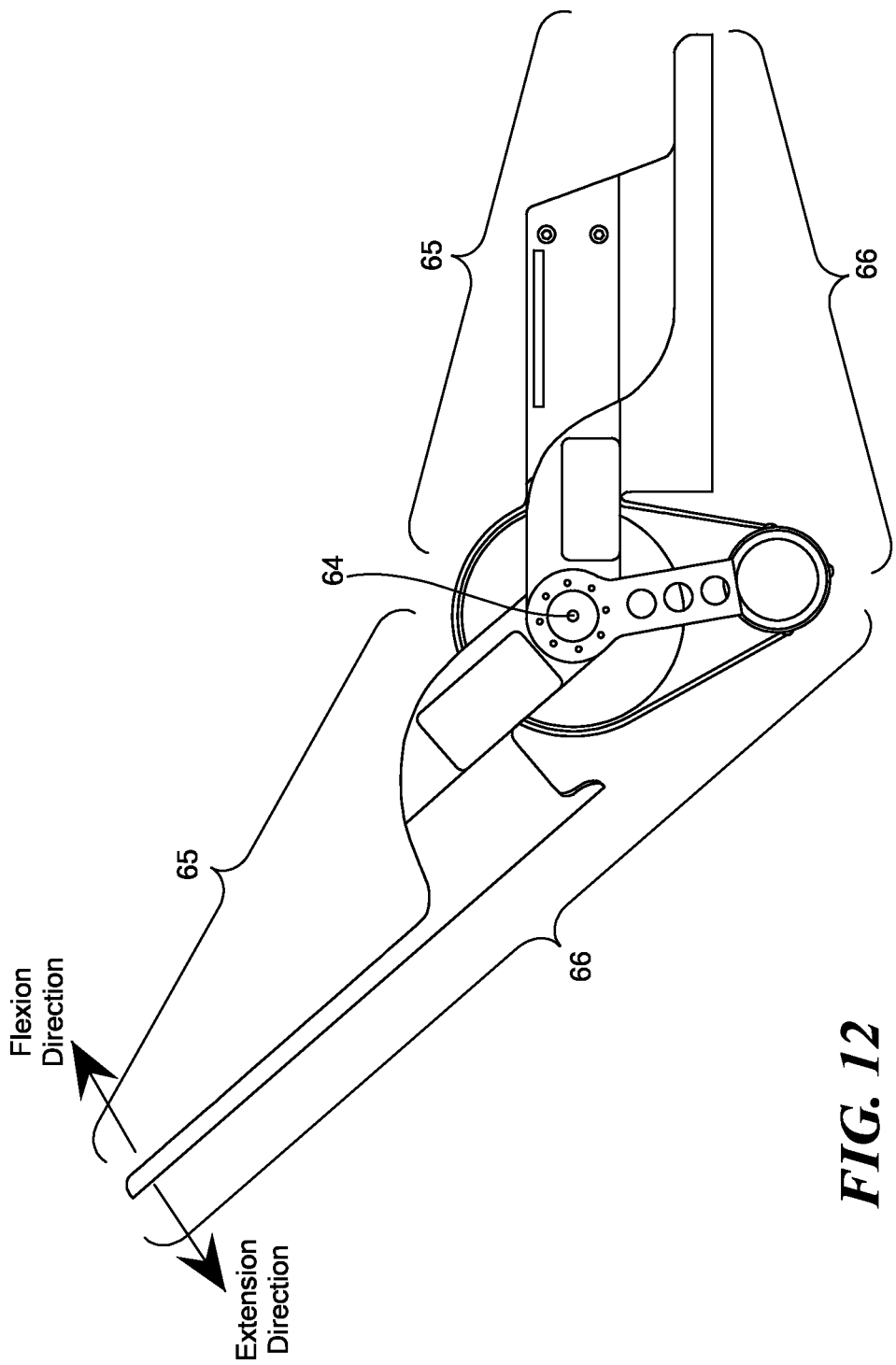
FIG. 12 shows a schematic view of the wearable component with the plastic cover removed according to illustrative embodiments of the present invention.
Figure 13:
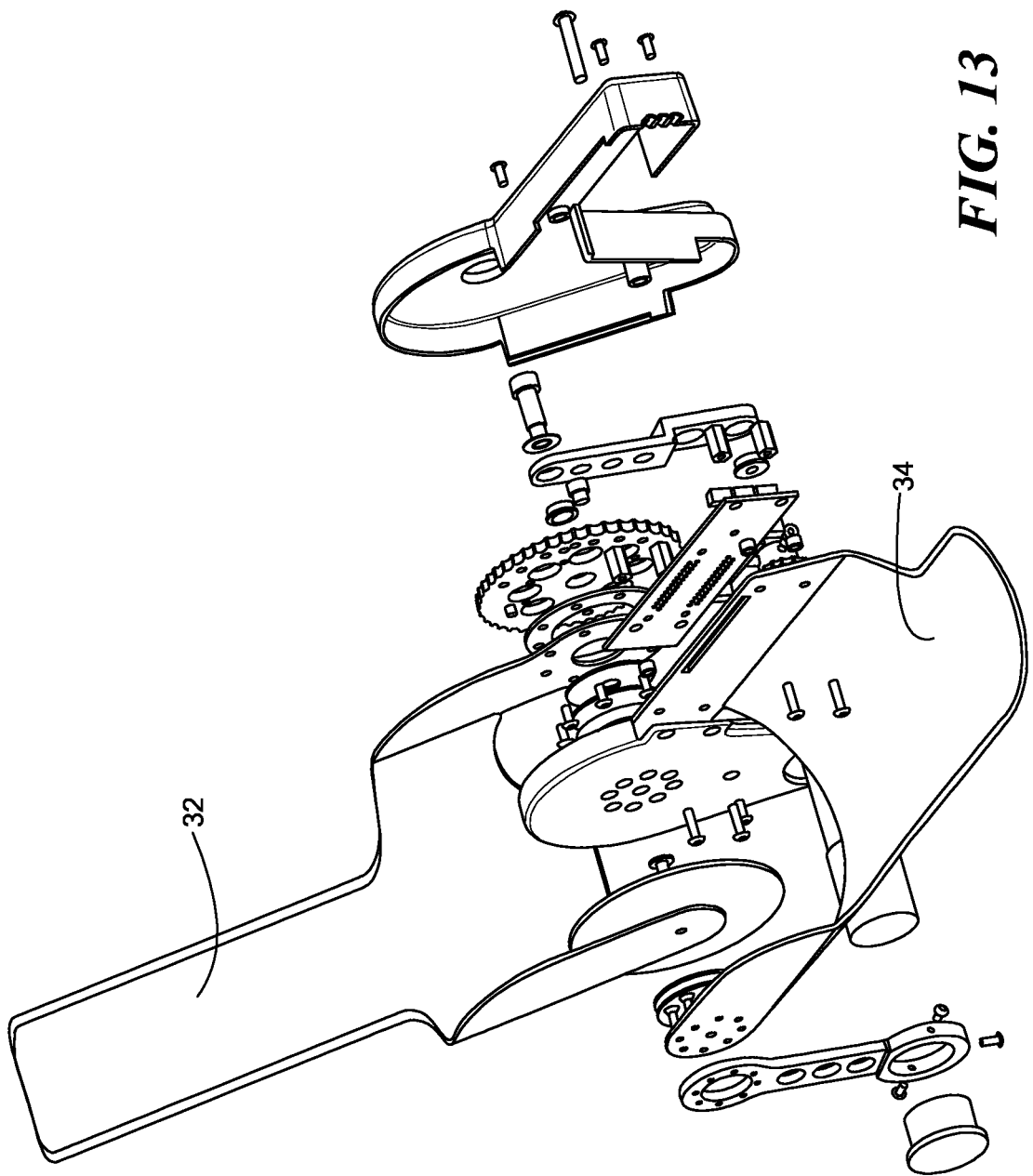
FIG. 13 shows an exploded view of the wearable component according to illustrative embodiments of the present invention.

As shown in FIG. 12, the brace 7 may move in a flexion direction and an extension direction, which define an inside region 65 and an outside region 66 of the brace 7, respectively. For example, when using an elbow brace, the motion of the brace that corresponds to the flexion direction is when the forearm approaches the upper arm (e.g., when the arm bends and the bicep muscle is contracting). Similarly, the motion of the brace that corresponds to the extension direction is when the forearm moves away from the upper arm (e.g., the arm straightens and the tricep muscle is contracting). Accordingly, the inside region 65 of the brace 7 includes the region where portions of the brace 7 are facing one another during flexion, and approach one another during flexion. Similarly, the outside region 66 of the brace 7 includes the region where portions of the brace 7 are facing one another during extension, and approach one another during extension (or are moving away from one another during flexion).

Figure 16:
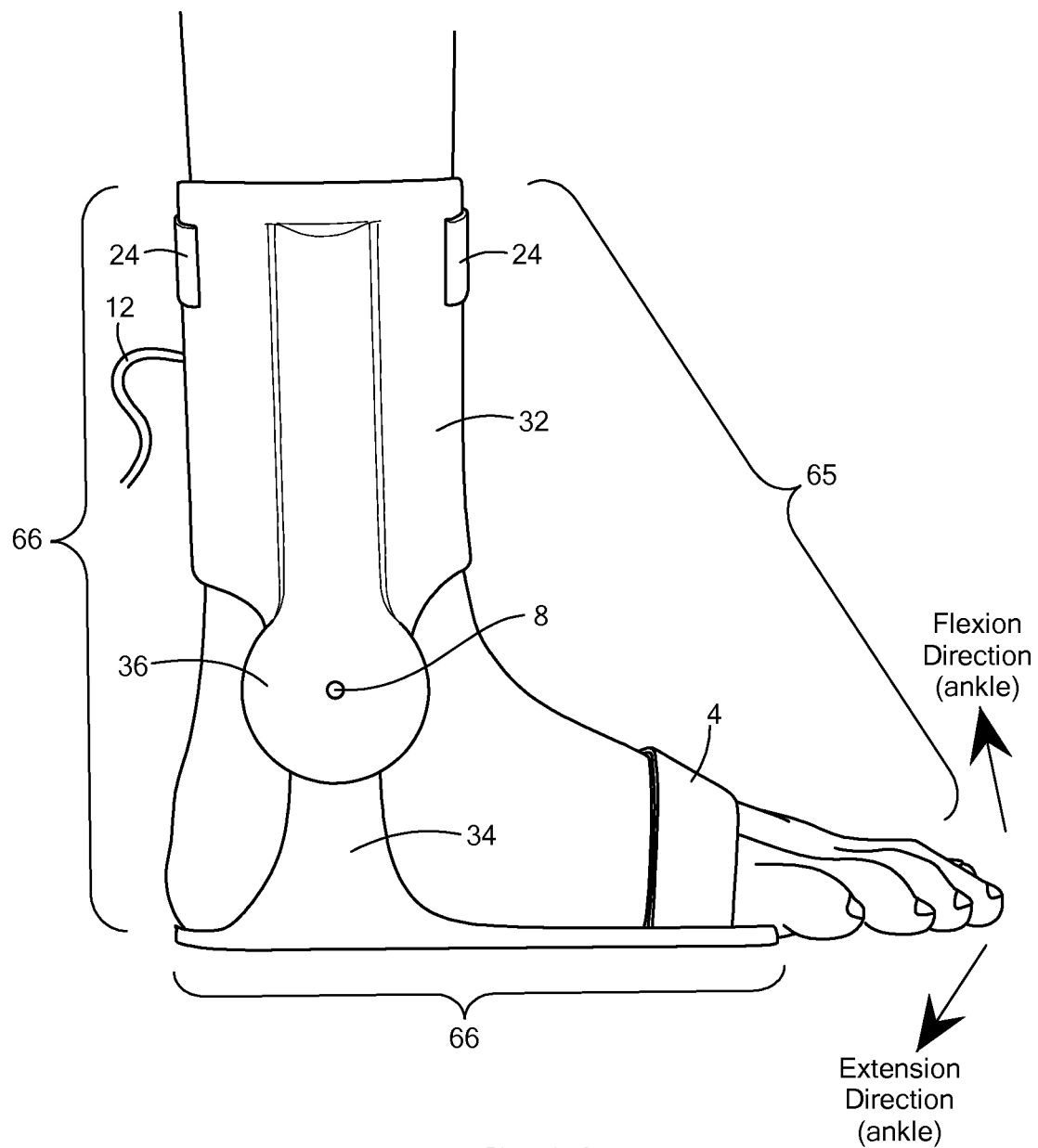
FIG. 16 shows a sketch of a wearable component around an ankle according to illustrative embodiments of the present invention.
Figure 17:
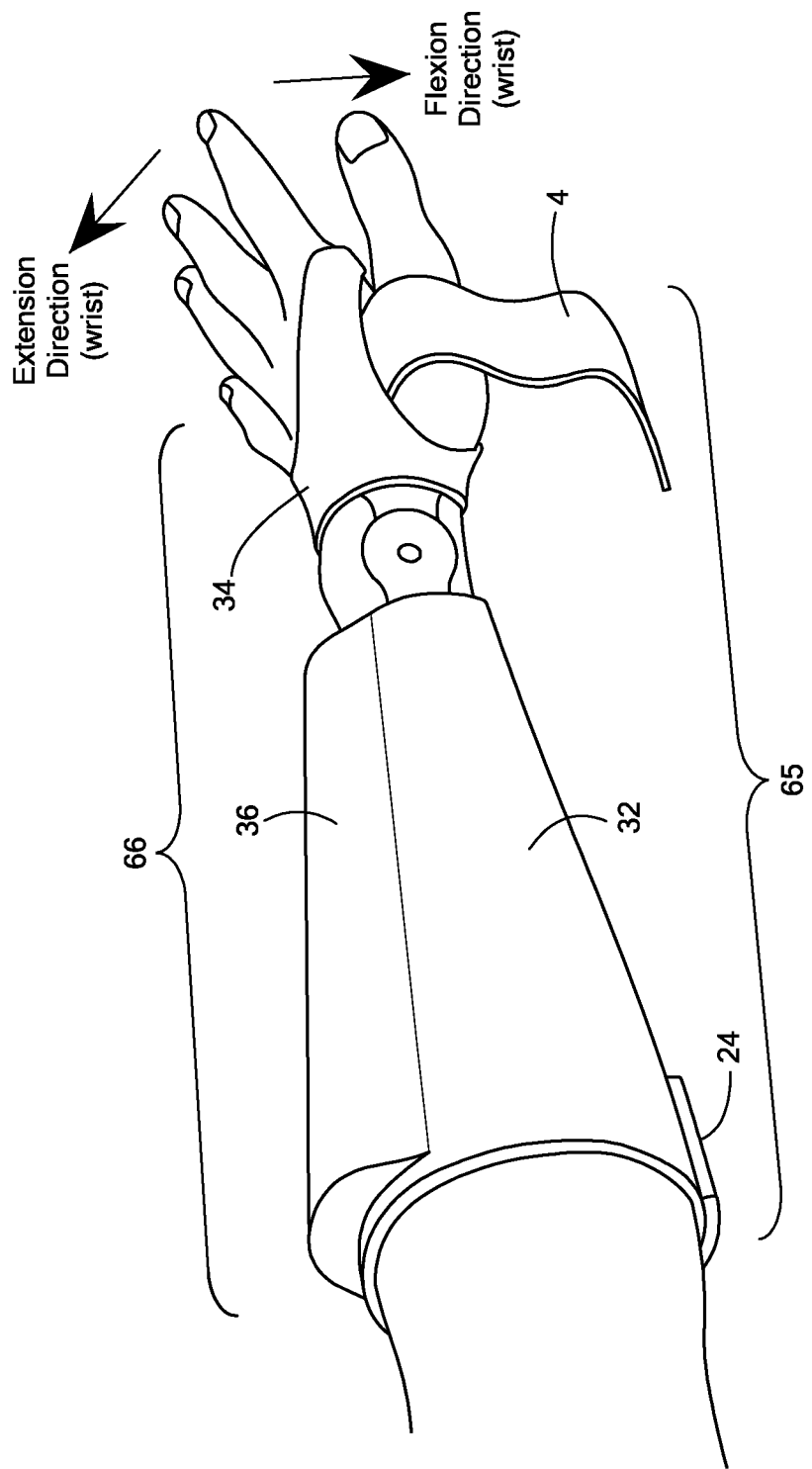
FIG. 17 shows a sketch of a wearable component around a wrist according to illustrative embodiments of the present invention.
Figure 18:
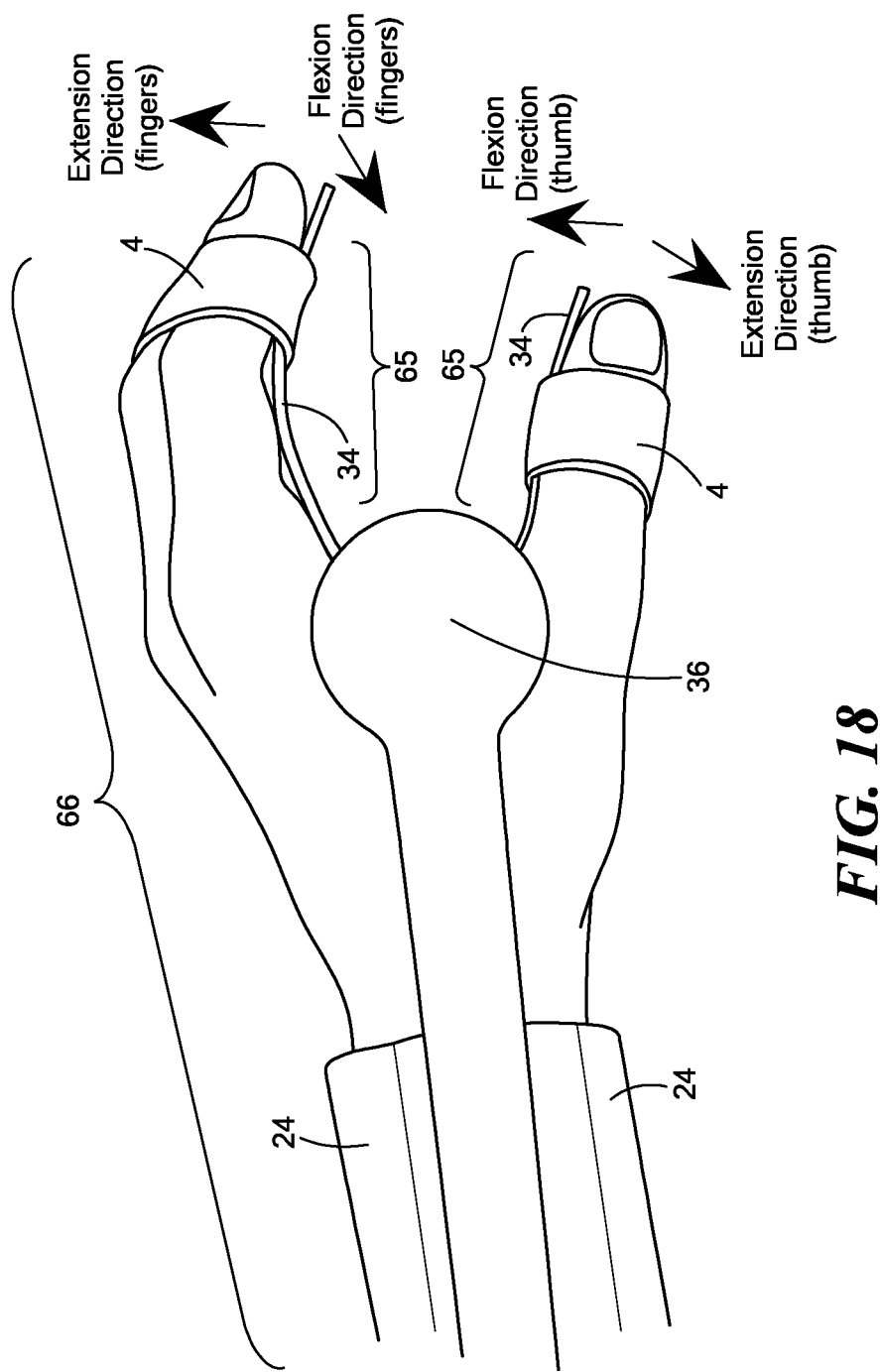
FIG. 18 shows a sketch of a wearable component around a hand according to illustrative embodiments of the present invention.

For example, in the case of the arm, the outside region 66 is the region proximate to the tricep, the olecranon (the point of the back of the elbow), and the underside of the forearm (with hand and arm in handshake position). In the case of the ankle (as shown in FIG. 16), the outside region 66 is the region proximate to the calf (back of the lower leg), the achilles tendon, the back of the heel, and the bottom of the foot. In the case of the wrist (as shown in FIG. 17), the outside region 66 is the region proximate to the top of the forearm (with arm held straight out in front, parallel to the floor, palm facing the floor), the back of the hand, and the back of the fingers. In the case of the hand (as shown in FIG. 18), the outside region 66 is the region proximate to the top of the forearm (with arm held straight out in front, parallel to the floor, palm facing the floor), the back of the hand, the back of the thumb, and the back of the fingers.

Similarly, the inside region for a knee brace (not shown) is the region proximate to the hamstrings, the back of the knee, and the calf (the back of the leg). The outside region for a knee brace is the region proximate to the quadriceps, the front of the knee (kneecap), and the front of the shin (the front of the leg). In this case, the motion of the brace that corresponds to the flexion direction is when the foot moves closer to the hamstrings (back of the leg) and the extension direction is when the foot moves away from the hamstrings (or the leg straightens).

Embodiments of the present invention may dispose the majority of the actuator assembly volume (e.g., the motor, gearhead, one sprocket and most of the chain) in the outside region 66 of the brace 7, although some portion of the actuator assembly volume (e.g., one sprocket) may be located coaxially with the brace 7. Previously, this geometry was difficult to achieve in wearable robotic devices since few actuation systems were designed that allow non-coaxial actuators, while remaining small and light enough for wearable applications. Embodiments of the present invention make this possible through novel geometries, high-strength materials, torque limiting characteristics, component configurations, attachment locations, in combination with a lightweight wearable system.

Figure 14:
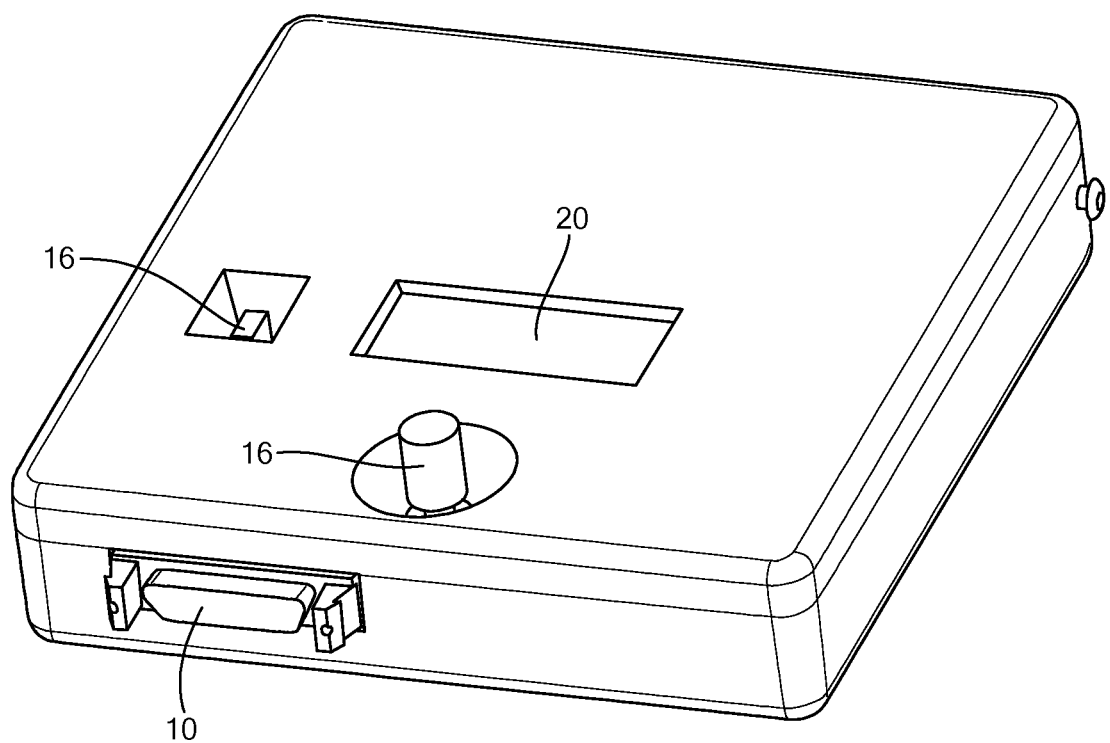
FIG. 14 shows a schematic view of a control system according to illustrative embodiments of the present invention.
Figure 15:
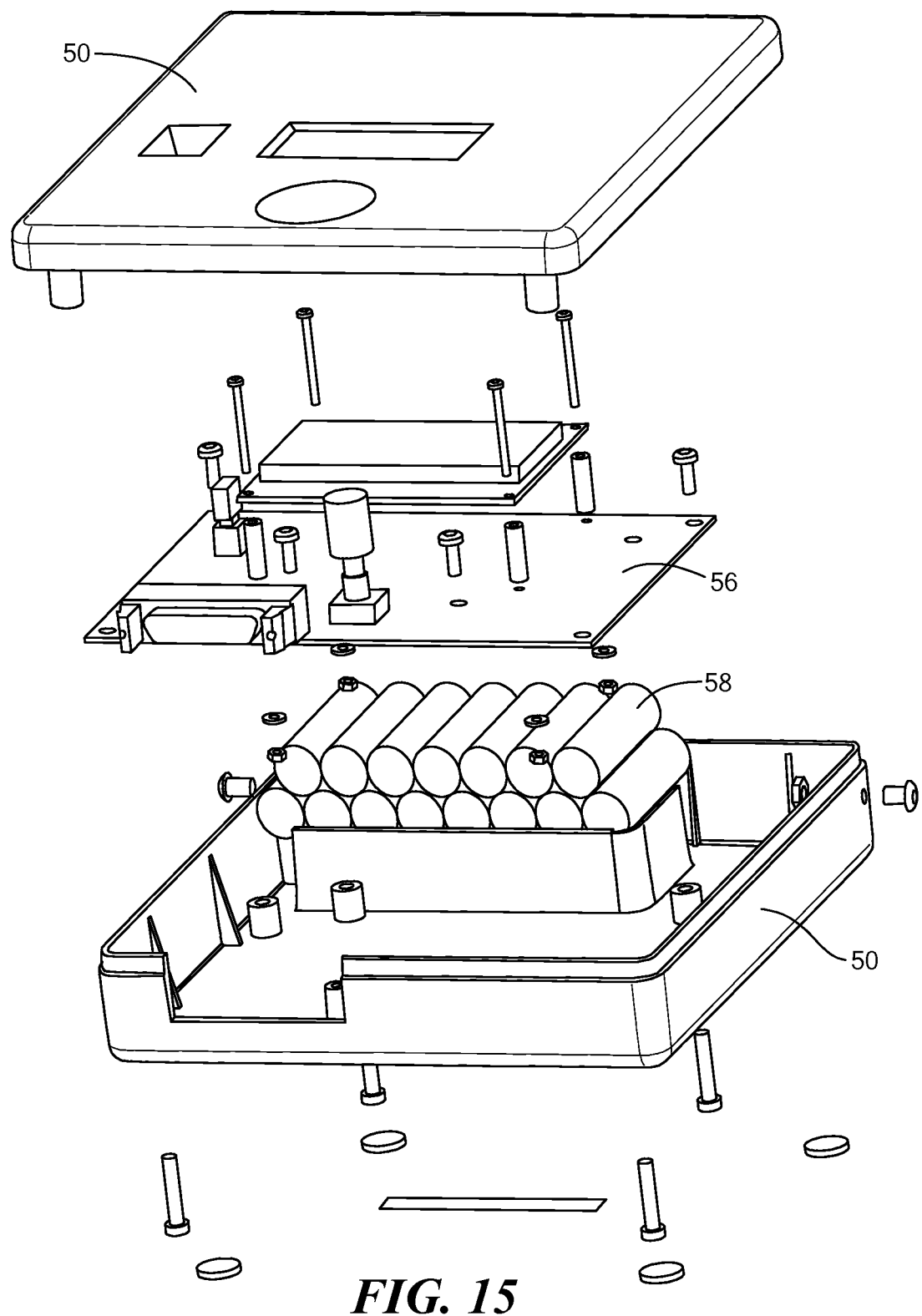
FIG. 15 shows an exploded view of the control system according to illustrative embodiments of the present invention.

As shown in FIGS. 14 and 15, the control system 18 includes a user interface through which a user interacts with the device. The user interface may include inputs 16, such as single or multiple knobs, buttons, switches, touch sensors, touch screens, or combinations thereof, for user input and feedback, and may include outputs 20, such as audio and/or visual devices, e.g., speakers, lights, LEDs, tactile sensors or transmitters, visual displays, such as LCD screens. The control system 18 may also include a processor 56 which processes the signals from the sensors 24, communicates with the user interface 16, 20, applies control algorithms and sends output commands to the actuator assembly 36. The control system 18 may also include a power source 58 and a data storage and management system (not shown) which may interact with the processor 56.

Although embodiments of the device are described and shown with various components in the control system 18, some components, such as the power supply 58, user interface, processor 56, may be located on the wearable component 2, on the control system 18, or both. As previously mentioned, electrical and mechanical cables 12 may connect the control system 18 to the wearable component. Mechanical cables may be part of the actuator assembly, e.g., pull-pull throttle cables. Electrical cables may carry sensor signals, motor power, ground, shielding, or sensor power. Various ports and/or connectors may be used on the control system 18 for connection and communication to external devices, additional wearable components or systems, charging systems, and/or additional sensors. Further, an additional control unit, containing a user interface and feedback mechanisms, may be connected to the main control system 18 using such connectors. The control system 18 may include an enclosure 50 to house the various electrical and mechanical components. The control system 18 may allow the user or trained person to change settings on the device, observe the device and/or user status, manage stored information, turn the device on or off, or make other technical or clinical changes. The control system 18 may also provide the user and/or caregiver with information regarding range of motion, safety concerns, number of repetitions, clinical updates, rehabilitation progress or other technical or diagnostic information.

The beneficial attributes of embodiments of this device configuration enable a practical implementation of the technology as a functional and rehabilitation aid. For example, placement of the motor 36 in a position near the axis of rotation 64 of the joint allows for a minimal drive assembly 41 enabling a light weight, compact system. Placement of the motor 36 in a metallic tube housing 26, shields the motor 36 and the user as well as other sensitive electronic components from electromagnetic radiation, while providing protection for the system against impacts and foreign objects. The housing 26 also acts as a support structure for the brace 7, simplifying the process of donning and doffing of the wearable component 2. Further, the housing 26 acts as a handle, to facilitate clinician assistance, and to help in carrying the brace 7. The clinician assistance may include supporting or carrying some of the weight of the device when the subject is wearing the device, e.g., to relieve weight or stress from a subject's shoulder during the execution of physical tasks. In addition, the drive assembly 41 components 42, 44 are placed on the outside of the limb, such as an arm, to minimize the risk of abrasion of components against the user's body. For example, the drive assembly 41 may be located on one side of the device for a right arm version and on the other side of the device for a left arm version. Placing the actuator assembly in an area where collisions are highly unlikely between the actuator assembly and the limb segments potentially decreases the likelihood of injuries to the limb segments. For example, collisions may be more likely if parts of the actuator assembly were in the inside region of the brace or located within the flexion direction since limb segments often move through that region.

Figure 33:
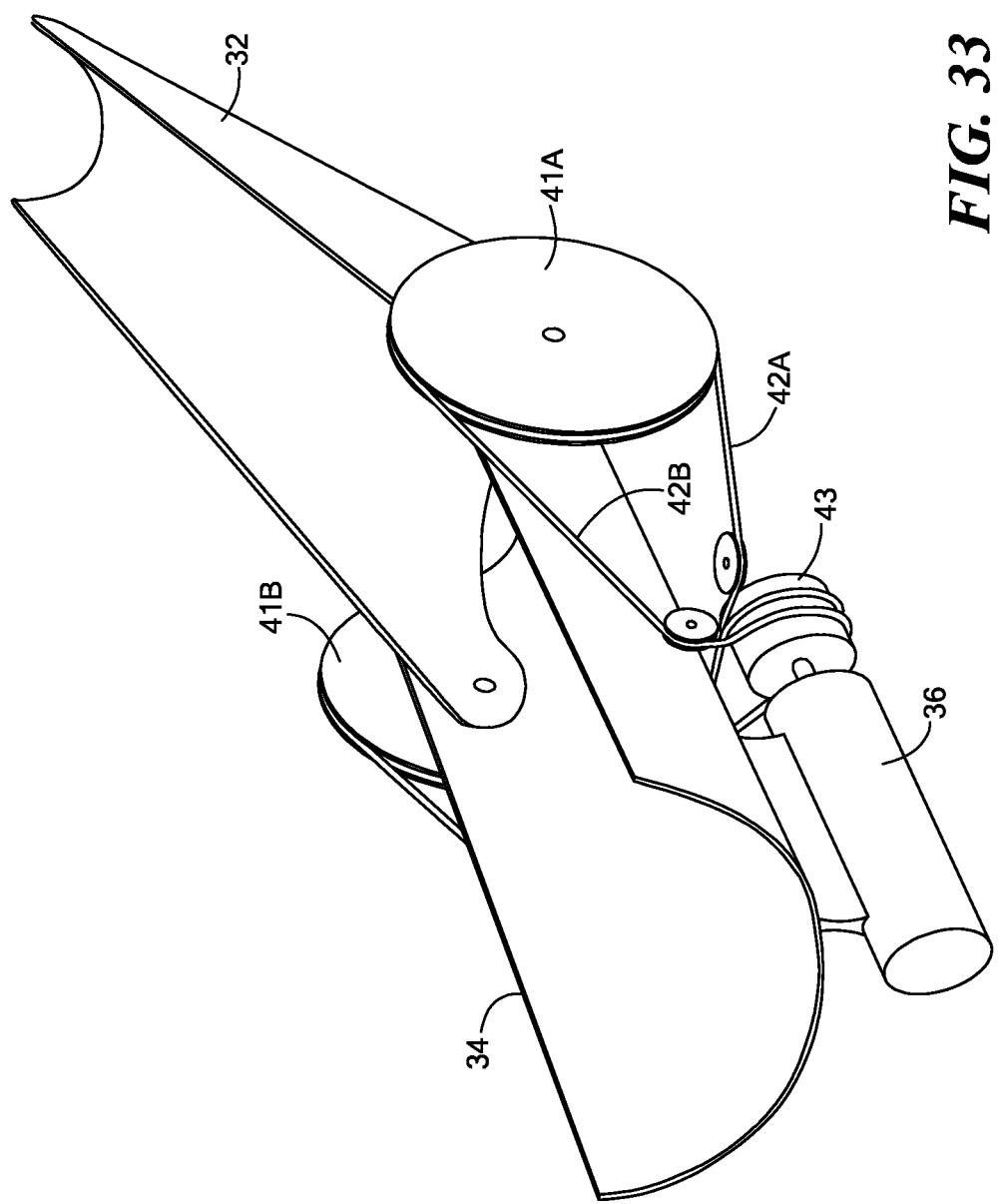
FIG. 33 shows an illustrative embodiment of the invention in which a single actuator is connected to drive assemblies on both sides of the joint.
Figure 34:
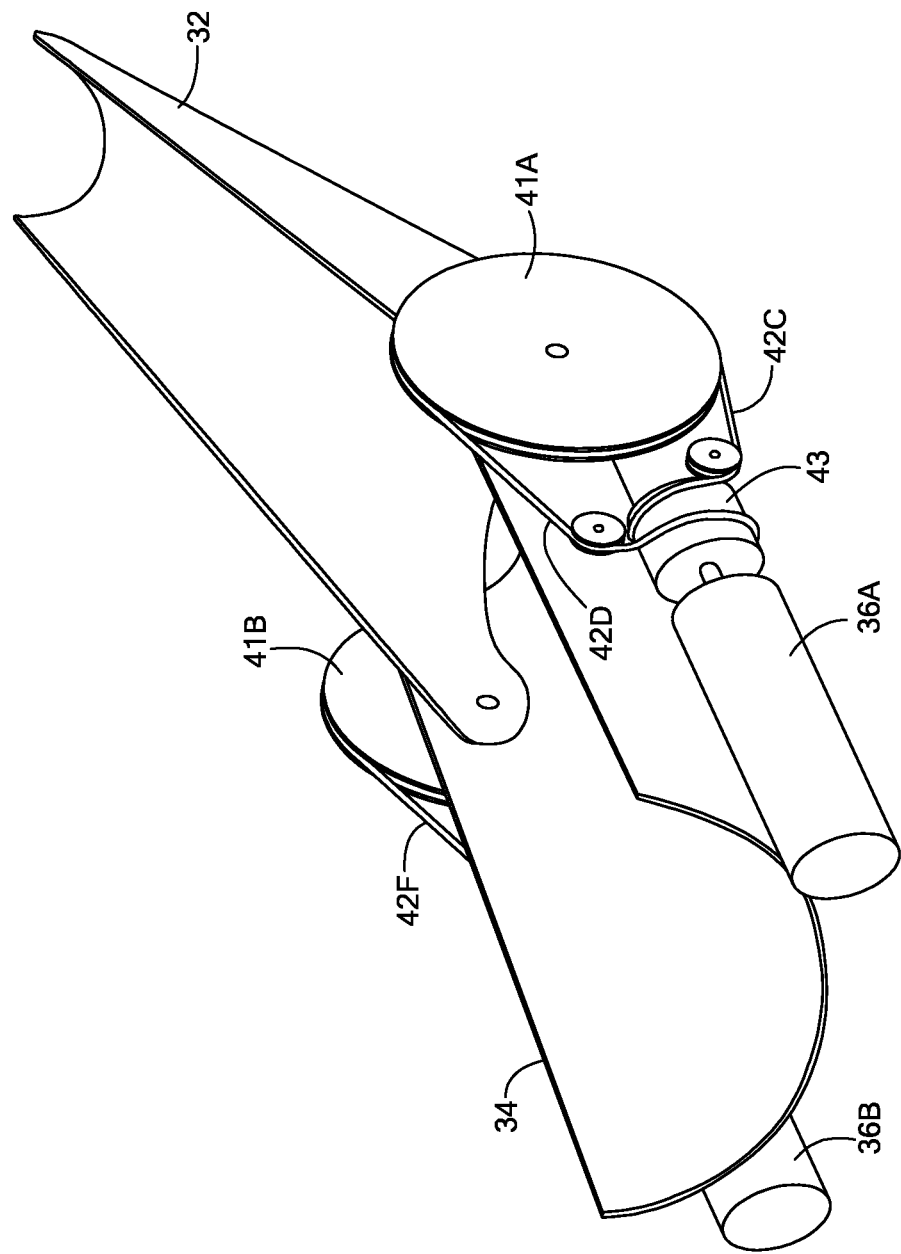
FIG. 34 shows an illustrative embodiment of the invention in which two actuators, each located on opposite sides of the joint, are each connected to a drive assembly on a corresponding side of the joint.

FIGS. 33 and 34 show other embodiments in which torque is applied to both sides of the joint, e.g., medial and lateral sides. In certain embodiments, it may be advantageous for the actuation mechanism to provide torque to the brace on both sides of the joint in the same direction—flexion or extension—so as to minimize twisting and off-axis torques on the brace material or on the limb. In other embodiments, two electrical actuators may be used. In such embodiments, both actuators may provide torque in the same direction simultaneously (in which case one actuator may apply torque on one side of the joint, while the other actuator applies torque to the other side of the joint), or one actuator may provide torque in the flexion direction and another actuator may provide torque in the extension direction. In another embodiment, the actuation mechanism may consist of one electrical actuator that applies torque in one direction (e.g., flexion) on one side (e.g., medial) of the brace/joint, while the same actuator, when actuated in a different direction, applies torque in the other direction (e.g., extension) on the other side (e.g., lateral) of the brace/joint.

FIG. 33 shows an embodiment in which a single actuator motor 36 is connected to a drive assembly 41A on one side of the joint, and a drive assembly 41B on the other side of the joint via drive assembly component 43. In this embodiment, lower extension cable 42A, and upper flexion cable 42B are used to deliver torque created by actuator motor 36 to the drive assembly components 44A, 44B.

FIG. 34 shows an embodiment with two actuator motors 36A and 36B, each being located on opposite sides of the joint. In this embodiment, each actuator motor drives a separate drive assembly 41 via separate cables 42C—medial lower cable: extension, 42D—medial upper cable: flexion, and 42E—lateral lower cable: extension (not shown), 42F—lateral upper cable: flexion. With this arrangement, the two actuator and drive assemblies can operate to provide torque simultaneously, or one actuator and drive assembly can provide torque for movement in the flexion direction, and the other for movement in the extension direction.

Embodiments of the present invention also provide a well balanced brace, which improves ergonomics. For example, the actuator assembly may be centered on the back of a limb or in the outer region, rather than coaxial with the limb where the assembly would stick out to the side. In addition, the configuration may be less likely to collide with other body parts during motion since a majority of the volume of the actuator assembly may be positioned in what we have termed the outside region of the brace rather than to the side of the joint. Collisions with other objects (e.g., door frames, arms of chairs, walls, vehicles, other people, etc.) may be less likely when a majority of the volume of the actuator assembly (including, for example, its motor) is in an outside region rather than in the coaxial configuration. Also, for certain joints, the configuration may be more aesthetically pleasing.

In order to achieve high torques, the actuator assembly may include a planetary gear head directly coupled with the output of the motor 36, and the final stage of reduction in the drivetrain is achieved where drive assembly 41 components 42, 44 are part of a belt, cable, or chain drive system, which have higher torque capacities than the planetary gear head. For example, the actuator assembly may be comprised of an electric motor, and the gear reduction that is coupled to apply torque about the joint may use a tensile member 42, (described previously in connection with FIGS. 7 and 8 as implementable by a chain, cable, cord, or belt) and tensile member drive mechanism 44 (also described previously as implementable by a sprocket, gear, pulley, or similar rotating mechanism). For example, a grooved gear or drum mechanism may be used to drive the tensile member. The actuator mechanism may include a self-equalizing tensioner, such as a drum drive with a diametrical groove and with a continuous cable, that maintains approximately equal tension over the tensile member, or on several tensile members.

The EMG sensors 24 may be located on the user's muscle, e.g., bicep or tricep, for use in flexion or extension modes. For example, the bicep configuration may be achieved by attaching (e.g., using hook and loop fasteners) the sensors 24 to the inside of the elastic strap 4 that couples the brace 7 to the bicep. Similarly, the tricep configuration may be achieved by attaching (e.g., using hook and loop fasteners) the sensors 24 to a hook-sensitive pad 22 (e.g., with compliant, compressive elastic material under it to ensure continuous pressure against the skin) inside the second section 34 of the brace 7, so that the sensors 24 are contacting the tricep.

The control algorithm used may apply a torque in a first direction that is proportional to a magnitude of the EMG signal, and may provide a constant force in a second direction. Some of the electronic hardware 38 (for example, EMG processing hardware) may be located on the wearable component 2 of the device, to avoid electromagnetic noise problems associated with sending signals over the long cable 12 between the control system 18 and the brace 7. In another embodiment, a control algorithm may be used that provides a constant force to the first and second sections 32, 34 in a first and/or second direction. The control algorithm may then switch to providing a force in the first and/or second direction that is based on the sensed EMG signal from the sensing system 24.

In addition, the larger, heavier components of the device may be located in the external control system 18, to minimize the size and weight of the wearable component 2. The control system 18 may be equipped with a shoulder strap 14 to improve portability of the device.

Although embodiments have been described and shown with regard to an arm and motion about the elbow, the device may be adapted for use with other body parts and joints. For example, FIG. 16 shows the wearable component around an ankle, FIG. 17 shows the wearable component around a wrist, and FIG. 18 shows the wearable component around a hand. For example, when the device is adapted for use about the ankle, the straps 4 provide coupling of the brace 7 to the leg and the foot, allowing the sensing system sensors 24 to obtain and measure signals from the user's muscles on the leg and/or the foot. The actuator assembly then applies a torque or force to the sections 32, 34 of the brace 7 about the ankle joint.

Similarly, when embodiments of the device are adapted for use about the wrist, the straps 4 provide coupling of the brace 7 to the forearm and the hand, allowing the sensing system sensors 24 to obtain and measure signals from the user's muscles on the forearm and/or the hand. The actuator assembly then applies a torque or force to the sections 32, 34 of the brace 7 about the wrist joint. When embodiments of the device are adapted for use on the hand, the straps 4 provide coupling to the fingers and the hand, allowing the sensing system sensors 24 to obtain and measure signals from the user's muscles on the hand and/or the fingers. The actuator assembly then applies a torque or force to the sections 32, 34 of the brace 7 about the finger joints. In other embodiments, the device may couple only to one side of a joint.

In one embodiment, torque is applied to induce motion about the joint via the motor 36 and the gearhead, and a chain and sprocket reduction 42, 44. Screw heads 40 may be used as the hard stops or limits, which collide with the structure of the brace 7 to limit its range of motion. The drivetrain and potentially dangerous moving parts are covered by the protective covers 28, which may be made of plastic shells.

There may be multiple modes of interfacing with various embodiments of the device. Parameters, such as control, brace strength, system gains and sensitivities, virtual spring parameters and strengths, EMG threshold values, maximum and minimum torques, operational range of motion, damping parameters, user feedback modes, data logging parameters, may be varied and adjusted by the user and/or a trained individual via the user interface 16, 20. Any of these parameters may be adjusted independently of one another or in conjunction with one another. For example, the user and/or trained individual may adjust the force parameters, such as the assistance level in the flexion direction and the extension direction, independently of one another. The control system 18 may also provide for "one-touch" adjustment of several related parameters that together control an operational aspect of the device. For example, changing the assistance level may require changes to several parameters. Control system 18 may provide for a simple "up" or "down" assistance level adjustment via user interface 16, 20, that automatically makes the required changes to all the parameters that affect assistance level. This automatic parameter adjustment based on a simple user input may also take into account other system states, parameter values, sensor values, etc, when deciding which adjustments to make, or how to interpret the "one-touch" user input. The user interface may be used to make adjustments to the aforementioned parameters, and to give feedback to the operator of the device. The parameters may be adjusted by the user and/or trained individual at any time, e.g., before, during (including while the brace is moving and/or stationary) and/or after the time the brace is in use.

FIG. 35 shows a chart illustrating how a "one-touch" adjustment to increase flexion assistance might also result in changes to the extension assistance level. Here, it is assumed that the user interface is allowing the user to increase flexion assistance by pressing a button. The chart shows an example of a look-up table that may be programmed into the device, so that the user may affect multiple parameters with a single button push. In this example, the user pushes the button, but the table shows how the device will change two parameters, depending on two factors—the current states of those two parameters. For example, if the user pushes the button while flexion assistance is low (1) and extension assistance is low (1), the device responds by incrementing the flexion assistance level. If the user pushes the FLEX button while flexion assistance is high (3) and extension assistance is high (3), the device responds instead by decrementing the extension assistance level.

During operation, there may be continued real-time interaction between the user and the device in some embodiments of the present invention. For example, sensors detecting the range of motion of the joint may give the user feedback (audio, visual or both) regarding the range of motion of his or her exercises. Counters may keep track of the number of repetitions and number of exercises completed and provide the user with that feedback (audio, visual or both). Timers may keep track of the elapsed time and provide the user with that feedback. The system may provide the user or caretaker with useful information that could be used to track progress, e.g., EMG amplitude or profile, velocity/torque/force/position information. Audio or visual cues may also be used to inform the user of the system status, e.g., battery charge level, errors, damage to the device or sensors, maintenance requirements.

Embodiments of the device may employ various control algorithms for controlling the force applied in one direction and the force applied in the other direction. The control algorithms may provide an asymmetric control of the device. For example, the output (command to actuator system) may be a function of the EMG signal measured (e.g., flexor or extensor muscle) and may also include parameters related to time, position, velocity, acceleration, forces measured, torques measured, temperature, user inputs (e.g., push buttons), signals from other medical or electronic devices (e.g., other orthotic devices, pacemakers, palm pilots, computer system, etc). The force in one direction may be based on the EMG signals from a first muscle, and the force in the second direction may be based on the EMG signals from the first muscle, may be related to the EMG signals from a second muscle, and/or may be based on an absence of any sensed EMG signals. The force in the second direction, however, does not use the same relationship as the first direction, thus the two forces are asymmetrical. In addition to the EMG signal relationship, the forces in either or both directions may additionally be based on other inputs.

For example, embodiments of the device may have a mode of operation in which the device passively moves the limb through a range of motion at a predetermined speed or through a pre-determined trajectory, until the EMG sensors detect user activity or user-generated signals. Upon detection of such activity or signals, the device may change its mode of operation so as to behave in a more responsive manner to the user's activity or signals, (e.g., as discussed above where the force in one direction may be based on the EMG signals from a first muscle, and the force in the second direction may be based on the EMG signals from the first muscle, may be related to the EMG signals from a second muscle, and/or may be based on an absence of any sensed EMG signals).

The user interface 16, 20 may be used in any number of ways. For example, in operation, a clinician or user may select any number of modes for operation of the device, such as a bicep mode or tricep mode, from the user interface. In a bicep mode, the device may provide EMG-proportional assistance in the bicep direction and a return force in the extension direction. In tricep mode, the device provides EMG-proportional assistance in the tricep direction and a return force in the flexion direction. The device may also have a bicep and tricep mode allowing for multiple inputs. The return force may be a constant force, a spring, a nonlinear force, etc. Various control algorithms are discussed in more detail below.

Embodiments of the device may also have a facilitation mode. Stroke patients often have difficulty extending their limbs, due to a lack of ability to flex specific muscles, e.g., tricep muscles. Often if the patient has something to push against, e.g., a therapist's hand, the patient can activate the appropriate muscles to extend the limb. This process is called facilitation, and is often accompanied with verbal encouragement, and/or tapping/pushing/shaking of the appropriate limb segment or muscle group.

Embodiments of the device may also have functional modes of operation that include a "limb-lock" mode where the device may lock the limb at a fixed angle based on a user command, such as a quick muscle twitch or other muscle signal profile, that may be detected as an EMG signal. The limb-lock mode may alternatively also be commanded by another form of command, for example, tactile through the user interface or another interface device, such as via a switch or touch screen; alternatively, the command may be verbal. Locking the limb may last for a certain amount of time or until another user command is received. The angle at which the limb locks may also be adjustable via the user interface or other interface device.

Embodiments of the present invention may apply torque against the user's limb (with or without feedback) as a means of providing the user with a force to push against or resist. This application of force or torque may be accompanied by other feedback means (for example a light which changes color indicating it's time to start pushing, or a voice from a speaker saying "Now don't let me move your arm," as the brace begins to push the user's arm in a particular direction). To further accompany the brace motion and to further encourage motion of the user's limb, the device may stimulate the user by having actuators which tap, squeeze, vibrate or apply pressure to various parts on the limb in conjunction with, or in lieu of, the application of torque. For example, the device may stimulate nerves associated with the stretch reflex in the appropriate (e.g., impaired) muscle to assist in providing motion. The device may assist the user in drawing attention to or focusing on the muscle group that should be used. Other stimuli (e.g., actuators, electrical stimulation, vibro-tactile actuators, sounds, sights, etc.) may be used during facilitation or during general use of the device. For example, a vibrator on the tricep muscle may vibrate when the user is asked to extend the arm—to remind the user that this is the muscle to activate.

In use, embodiments of the device should be calibrated for each session to take into account the muscle's normal electrical signal at rest (in order to distinguish rest conditions from intentional EMG muscle activity). An individual's EMG signal for a particular muscle will have some non-zero value even when that muscle is at rest. This value should be subtracted from all incoming EMG signals during use of the device. This parameter value may be changed manually through the user interface to change the sensitivity, or perceived sensitivity of the device. For example, if the device is to provide arm flexion or extension assistance, the device may determine calibration parameters for the bicep and/or triceps automatically by holding the user's arm, or having the user rest his or her arm, at a neutral position (e.g., arm resting on a table with the elbow bent at. 90 degrees) with the brace in its calibration mode. Because the resting EMG signal of a muscle changes with muscle length, a mid-motion-range calibration offset is desired to attain consistent operation through the muscle's full range of motion. The method of calibrating the device by having the user limb in a mid-range of motion relaxed pose allows a "baseline" resting EMG signal DC offset to be determined that corresponds to a mid-range electrical offset. The device may calibrate in a designated time with the limb held at a predetermined rest position, such as in 10 seconds with the arm at rest and the elbow at 90 degrees.

FIG. 36 shows an example of an EMG signal trace that might be observed during calibration and use of the device. Up until Time equals A, the trace reflects an EMG signal value of about X volts while the muscle is at rest during the calibration period. After Time equals A, the trace reflects an EMG signal for intentional muscle movement of the patient. This resting EMG voltage value is used to calculate a resting EMG offset so that the device can distinguish between the EMG signal of muscle at rest, and EMG signals indicating intentional muscle movement.

For certain users, it may be necessary to determine additional calibration parameters related to an assistive force profile in one or both directions. For example, a user may have difficulty extending his or her arm beyond a certain angle or through a certain range of motion due to stroke, spasticity, or other causes. In this situation, the device might auto-calibrate by applying torque to the user's limb in one or both directions with the device in a calibration mode, while the user may not be intentionally applying any muscle force, and determining the appropriate force profile required in one direction to achieve the desired range of motion. The desired range of motion may be determined by a clinician, therapist, doctor, patient, or by the device, based on sensory data, system parameters, and user input. This assistive force profile would then be used by the device, during normal operation, in conjunction with the EMG-based control and force profiles. This assistive force profile would be saved as a calibration parameter, which could be later adjusted manually through the user interface. Table 1 illustrates an example of the steps the device might take to determine an assistive force profile.

TABLE 1

Example of Auto-Calibration of Assistive Force in One Direction

Device in bicep mode
During calibration, the user interface prompts the user
to relax his arm and to let it extend under gravity
The device automatically determines an assistive force
profile by adjusting an assistive elbow extension
torque that allows the elbow to achieve the desired
extension range of motion
The device sets this profile as the default assistive
extension torque profile
This profile may be edited manually by using the user interface Embodiments of the system may also dynamically adjust the calibration values during operation, if changes in the user's electrical offsets are detected. For example, the calibration may be dynamically adjusted if the device detects changes in tone, sweating, temperature, stress, fatigue, excessive sensor movement (or frequent disconnect), pulse rate, blood oxygen levels, excessively high or low gain settings by the user, etc. If the system automatically detects user muscle fatigue and changes the calibration values, the system parameters may be changed to reflect that. In addition, the system may dynamically adjust certain system parameters such as signal filtering parameters. If the system detects changes in the signal characteristics, or in environmental or user characteristics, it may dynamically adjust filtering parameters (filter bandwidths, for example).

After calibration of the device, the operation screen may appear on the display 20, in which the user may set the values of one or more parameters, e.g., "gain" and "return." The "gain" sets the level of assistance in the first direction of motion (the scaling factor which scales the EMG reading) to give a proportional output command to the actuator assembly 36, 42, 44. "Return" sets the magnitude of the force in the second direction of motion, which may not be proportional to the EMG signal, e.g., a constant force or another control algorithm. The device may also be capable of further signal processing, such as low-pass filtering or smoothing of EMG signals, as is well known to those skilled in the art, to enable the device to provide a consistent or smooth force to the brace 7.

Embodiments of the present invention may also be combined with other therapeutic, supportive or functional devices which cause motion or stimulation by other means, or provide support to one or more body parts of the user. For example, the device having an elbow brace (as disclosed above) may be used in conjunction with a balanced forearm orthosis, or other body weight support system, to assist with moving the body part by reducing or eliminating the force of gravity on the body part. Alternatively, or in addition to, the device (e.g., having an elbow brace) may be combined with a functional electrical stimulation (FES) device, such as a hand grasp. The two devices may work together to encourage and stimulate natural movement patterns. For example, the devices may interact in a way that causes the hand to close (via electrical stimulation) only when the elbow reaches a preset angle, or only when bicep activity reaches a certain level, or only when the tricep is relaxed to below a certain threshold value. Alternatively, the hand closing may be user-activated (using FES) by a push-button switch, and may be opened (using FES) only when the elbow device measured the bicep relaxation to be below a threshold value. In other embodiments, the device may have programmed trajectories, such as a "reach and grasp" trajectory. In this case, the user initiates a reach, which is recognized as such by the elbow device, and this in turn causes hand FES device to close when the elbow nears full extension. The hand may then release its grasp when the bicep and/or triceps are relaxed to below a threshold value.

Embodiments of the present invention may also be used to provide assistance with recreational movement patterns, e.g., dance, sports, video games, musical performance, art creation activities, etc.

Electrical stimulation and orthotic power assist may also be used in conjunction with the device on the same muscle group or groups. For example, FES electrodes may be placed on the triceps, and a powered orthotic device may be worn on the arm. Electrical stimulation may be used as a means to initiate motion, or to promote user awareness, or to "wake up" the muscle. Once the muscle is slightly active and under the user's control, the amount of FES could be decreased and replaced by less painful assistive torques applied by the orthotic device.

Embodiments of the present invention may also combine EMG sensing (lower level sensing at muscle level) with neural stimulators (higher level sensing at the brain level). For example, the neural stimulators may include cortical stimulation or peripheral stimulation. The stimulators may be mechanical, electrical, chemical, acoustic, electromagnetic, and/or magnetic in nature. Similarly, embodiments may include the combination of mechanical actuation, such as application of torques/forces to the limb itself by the device with neurological stimulation, such as higher level electrical, chemical or mechanical stimulation at the brain level. For example, the device may be used in conjunction with deep brain stimulation, cortical stimulation, or peripheral stimulation, and the EMG sensing may be used in a closed loop control system to control, or be controlled by, the parameters used (e.g., frequency, duration, magnitude) in the brain stimulation or peripheral stimulation.

Embodiments of the device may also share user interface(s) with other devices, e.g., the other device(s) may use the user interface 16, 20 and/or the device uses the other devices' interface. Multiple devices, e.g., some may be powered orthotic devices and some not, may share a common user interface. This shared user interface may be wearable, may be wired or wireless, may be a personal computer, handheld computer, cell phone, etc. For example, systems that may share the user interface with the powered orthotic device may include pace makers, glucose monitors, electrical stimulation devices, heart rate monitors. Also, the user interface may serve as an input and output device, both accepting commands from the user (e.g., changing system setting, etc.) and providing information to the user (e.g., displaying information on a screen).

Embodiments of the present invention, may have all EMG processing, motor control, user interface, actuators and electronic hardware located in a control system 18 that is separate from the device. Preferably, the weight and size of the wearable component 2 is minimized. The control system 18 may be worn over the shoulder, or may be stationary with respect to the user. Mechanical torques and forces may be transmitted to the brace 7 via flexible drivetrains. In other embodiments, all processing, motor control, actuators, sensors and power sources may be located on or in the wearable component 2 to provide a fully portable system that involves no peripherals. In other embodiments, control system 18 may be a relatively small handheld device. This handheld device may have a wired or wireless connection with the wearable component 2. In other embodiments, control system 18 may be on or in wearable component 2, and may be located proximate to the joint.

A battery pack may be connected to the wearable component 2 and/or may be connected via a cable to the control system 18. For example, there could be a small battery pack with limited capacity that could be worn on the wearable component 2 (or is internal to the component 2), maximizing portability and completely eliminating the need for wires. There could be a higher capacity battery available that would allow longer run time, but may be too heavy or large to be worn on the wearable component 2. This battery pack may plug in and be worn on a belt, in a back pack, in a pocket, or elsewhere on the user's body. A larger battery pack may also be stationary with respect to the user, e.g., on a table top.

Embodiments of the device may have a mechanical structure such that the supporting joint about which the device rotates is the user's joint. In other words, the device may couple to the user's body above and below a joint, and may apply force or torque at those points, so as to cause motion about that joint. The device may not have hinges or pivot joints of its own.

Embodiments of the device may be integrated into articles of clothing, such that the donning of a particular piece of clothing (long-sleeved shirt, for example) would constitute donning the device, and the sensors and actuators would be held in place by the clothing itself. In this case, the power source (e.g., batteries) may be integral to the clothing or be removably attachable to the clothing.

Embodiments of the device may also have a system and/or protocol for ensuring proper alignment of the device with the appropriate joint. For example, the protocol may consist of visual markings on the device for alignment with key anatomical features, fixed angles for automatic brace alignment when the limb is pressed firmly in the brace, support structures for holding the device in place while the user pushes the limb into place.

Figure 19:
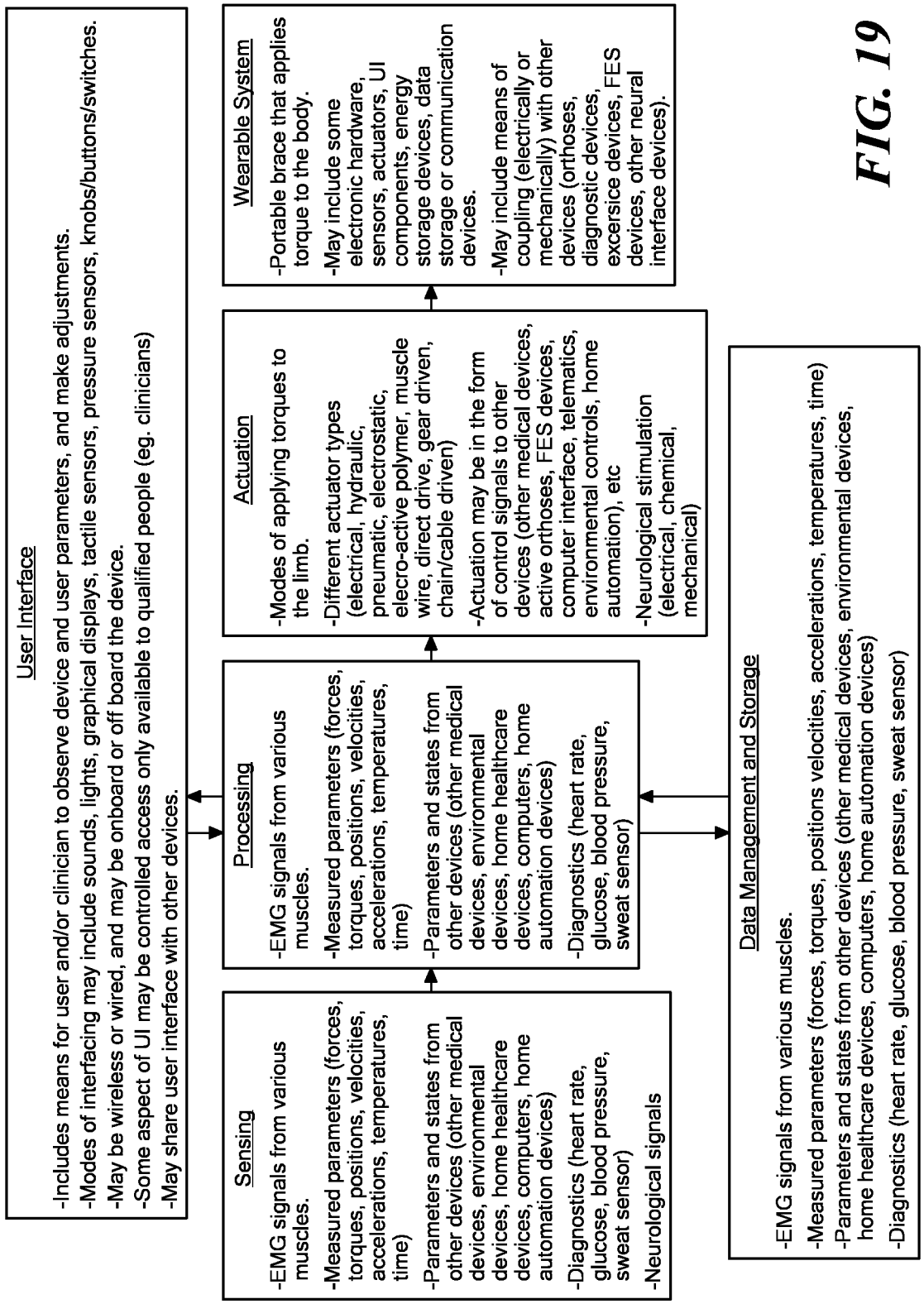
FIG. 19 shows a block diagram of the powered orthotic device system components according to illustrative embodiments of the present invention.

FIG. 19 shows the basic components of the device according to an embodiment of the present invention. In general, the sensing system collects information from a plurality of sensors 24 and sends those signals to a processing system. The information the sensors 24 collects may be from the user, the brace, the actuator assembly, the processing system and/or the environment. The processing system, in turn, processes those signals and generates an output signal to the actuator assembly. The actuator assembly applies torques and forces to the brace 7. Additionally, the user interface may include input and output devices which allow the user to provide input to the processing system and which allow the processing system to present information to the user. The data storage and management system may record and store data received from the device and/or the user.

The user interface may allow multiple levels of access control to the device parameters or usage/user data stored in the device. For example, the user may be allowed to control certain parameters (e.g., assistance levels, spring strengths, operational modes, volume, feedback mode, etc.) that may be adjustable via a compact user interface on the device or its peripherals (control system 18), while other parameters may have a controlled access and may only be adjustable by qualified individuals who either have a key or code, which may be a contact device (e.g., key or fingerprint reader) or non-contact device (e.g., using a barcode or radio frequency identification (RFID) reader) to make those changes, or who have a handheld or desktop device (e.g., computer) which interfaces with the device via a wired or wireless connection. The user interface may permit the changing of system parameters, downloading of usage and user data and diagnostics, uploading of user profiles and use protocols, erasing of system memory, calibrating of the device, or running of user training sessions. For example, the user may be first outfitted with the device at the clinician's facility, wherein the clinician puts the device on the user and connects to a computer. This initial session may involve a device calibration and tuning of parameters, followed by a training session wherein the user uses the device, e.g., plays a game moving cursors and hitting targets on the computer screen to become familiar with the motion of the device. A rehabilitation protocol may be uploaded to the device via the clinician's computer connection as well. The patient may then operate the device for subsequent sessions without the computer connection, performing functional tasks and rehabilitation exercises. Similarly, the user interface may have a secured access level that only qualified individuals or agencies may access in order to protect sensitive data related to the user.

Embodiments of the device may also interact with and/or connect to a computer or other remote user feedback system during operation. This may involve displaying progress information to the user or clinician during use, or may be used to facilitate or encourage motion of the limb, or to make therapy sessions more intuitive, functional, interesting, or entertaining, e.g., by playing a game. For example, the wearable component 2 and control system 18 may interact with a computer system through a gaming interface (e.g., Nintendo's Wii Fit). Embodiments may allow the user to log into a web portal, which may collect information about the user and the device's use, e.g., progress metrics such as amount of sessions, the time of each session, assistance levels or force parameters used, number of repetitions, heart rate, etc. This collected information may be accessed, captured or displayed via the control system 18, a handheld device, computer terminal, web portal, gaming system or electronic medical record. The information may also be sent to the user and/or health care provider, e.g., a clinician, therapist, doctor. Embodiments may also allow the interface to coordinate or assist one or more devices through an interactive session, e.g., multiple patients may be assisted through a therapy session by one health care provider, either in person or remotely, through the gaming interface.

This may also permit a clinician to remotely control or monitor use of the device by the user. For example, the user may connect the control system to the Internet, either through a cable or wirelessly, so that the device may communicate with a clinician or other person remotely located. The clinician may then adjust settings, monitor a session, monitor system values/parameters, or control and drive the device. The clinician may also have a corresponding robotic or haptic device that allows the clinician to feel or visualize the motion/strength/speed/quality of motion, etc. of the user wearing the brace. This enables therapy sessions to take place even when the therapist and patient are remotely located. For example, the patient may be practicing the prescribed therapy in an unsupervised manner, e.g., in the patient's own home, without the therapist present.

Figure 37:
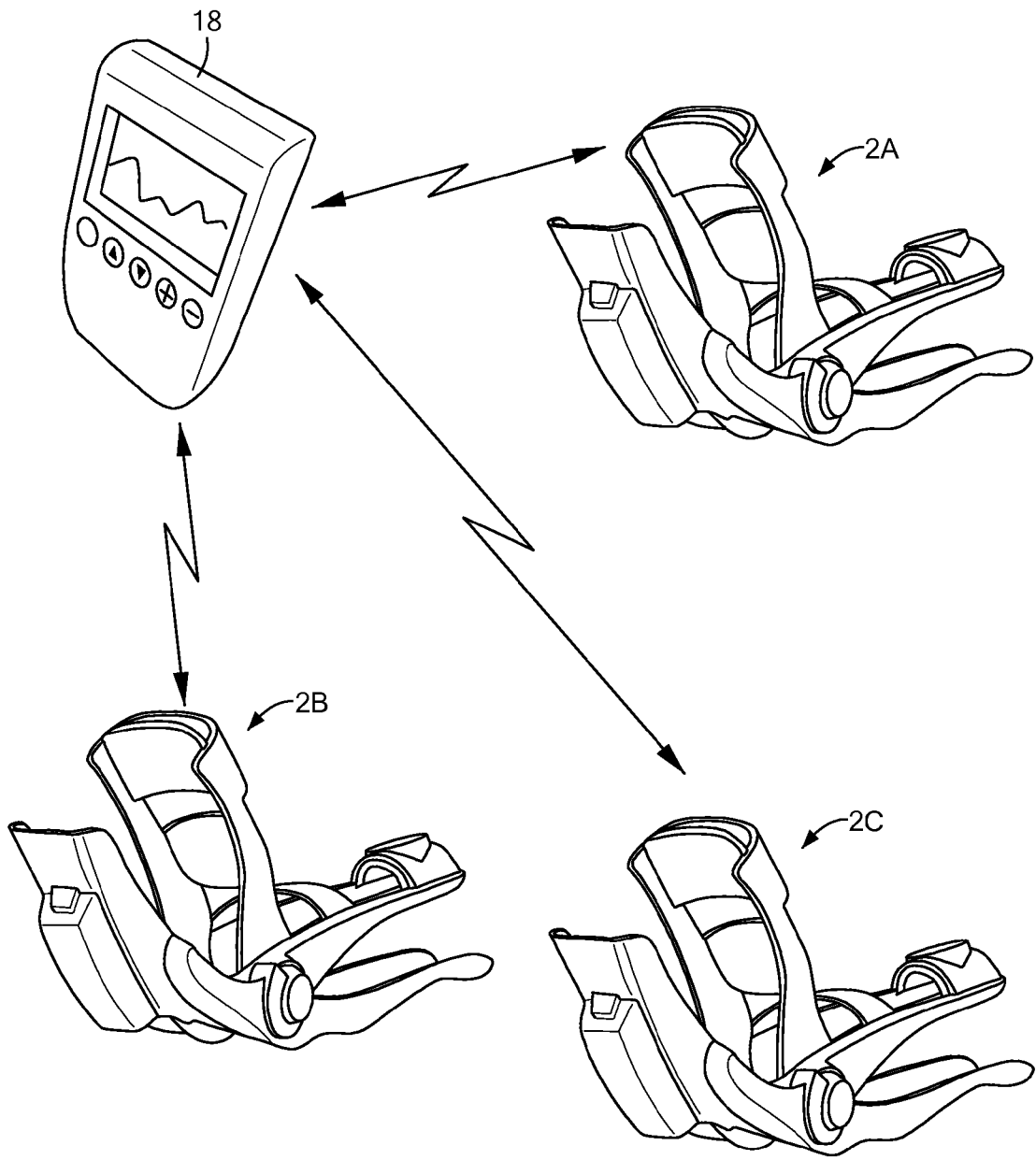
FIG. 37 shows an illustrative embodiment of a "master" control unit in communication with several wearable units.

FIG. 37 illustrates an embodiment of the device in which a "master" peripheral control unit 18A, for use by a clinician, may be used to interface with, provide power to, record data from, update parameters of, or provide actuation to multiple devices 2A, 2B, and 2C. For example, one master control unit may communicate and interact with multiple powered orthotic devices, other medical devices, home automation devices, diagnostic and monitoring systems, environmental controls and sensors. The master control unit 18A might be a standard control system 18 that is switched into a "master" software mode, or the master control unit 18A might include additional hardware, software, and functionality. Similarly, multiple control systems using hardware and/or software may interface with one or more devices. One power supply may also provide power to the device or multiple devices and multiple power supplies may provide power to the device or multiple devices. The master control unit 18A may connect to multiple devices simultaneously (in parallel), or sequentially (in series).

Figure 38:
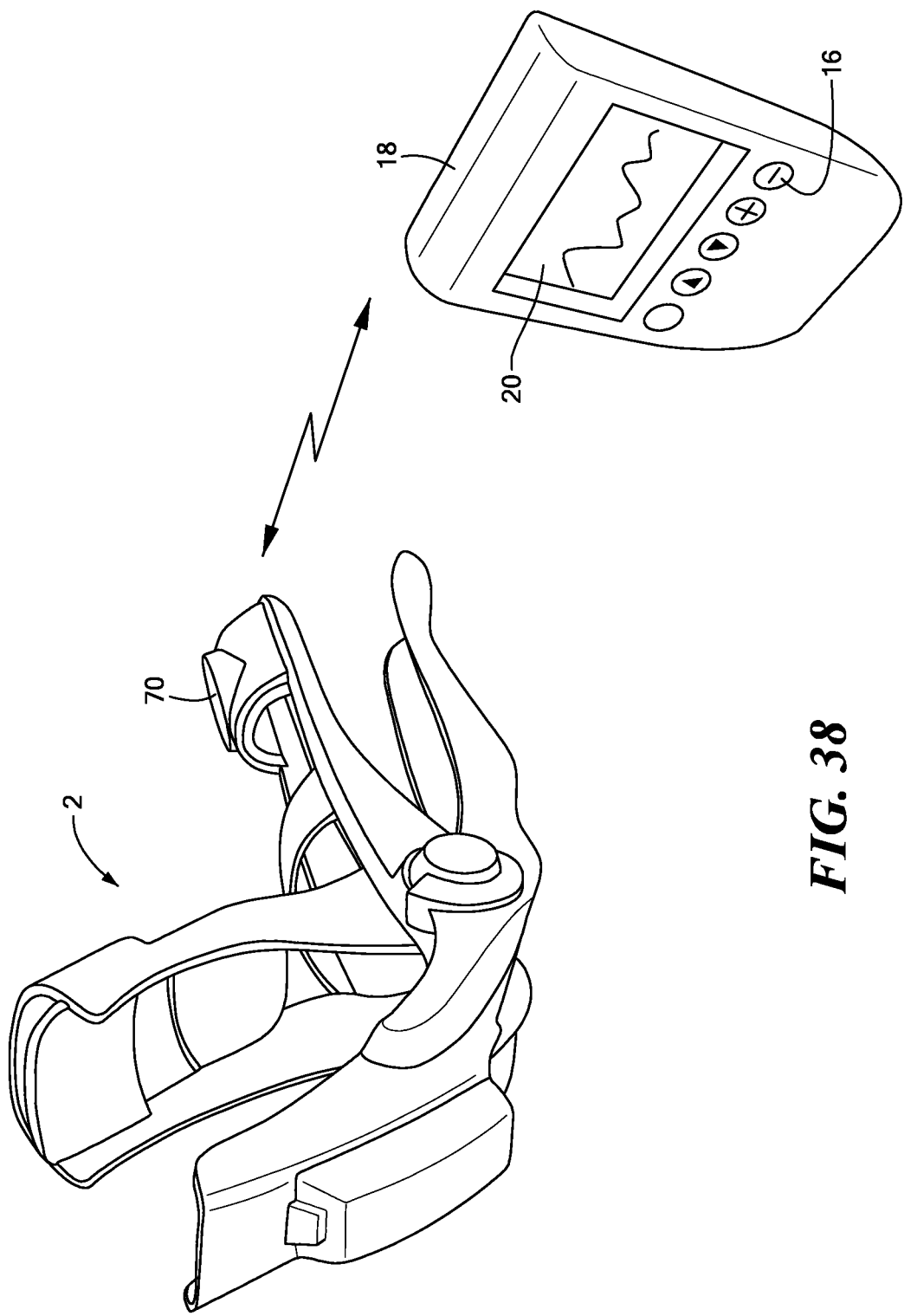
FIG. 38 shows an illustrative embodiment of the device in which a separate control system is used for device setup, and an onboard controller on the wearable unit may be used for normal operation.

FIG. 38 shows an embodiment of the device that has a separate control system 18 with a user interface 16, 20 that is used for setup and display, for adjustment and viewing of parameters and values during use, but is not necessary for normal operation. For example, the user takes the wearable component 2 and the separate control system 18 out of its case and turns on the control system 18. The user follows prompts by the control system 18, which could be verbal, on-screen, etc. The control system 18 prompts the user to put the brace on (with optional instructions provided by control system 18 on how to do this), align the sensor(s), and make the proper connections. The control system 18 then establishes communications, either by wire or wirelessly, with various components of the device, such as the sensor(s), the actuator assembly, etc. The control system 18 then instructs the user on how to calibrate the device. During calibration the controller sets and stores certain parameters important to safe and effective operation of the device. When calibration is complete, the parameters are stored in control system 18 and in onboard controller 70, which includes memory, located on the wearable component 2. During normal operation, the device will operate based on the parameters stored in the control system 18, the onboard controller 70, or both. If the user unplugs, powers off, or walks away from the control system 18, the wearable component 2 may continue to operate based on the parameter values stored in the onboard controller 70. If the user wishes to make changes to certain parameters, such as assistance levels in either direction, EMG sensitivity, volume, exercise program, operational mode, etc., he or she may do so by re-engaging the control system 18, e.g., turning it back on, plugging it back in or re-establishing a wireless connection to the wearable component 2, walking back into range, etc., and making adjustment via the user interface 16, 20, on the control system 18. Onboard controller 70 may also include an onboard user interface that allows the user to adjust a subset of parameters, such as assistance level, and perform certain functions, such as restore defaults, system reset, and connect with a remote device. When control system 18 is reconnected to the device, a parameter synchronization operation may resolve any discrepancies between the parameter values stored (and possibly changed) onboard the wearable component 2, and the parameters displayed and/or stored via the control system 18. The onboard user interface may also have a display that shows power on/off, battery status, wireless connectivity, error state, EMG signal, and real-time user feedback information.

Figure 39:
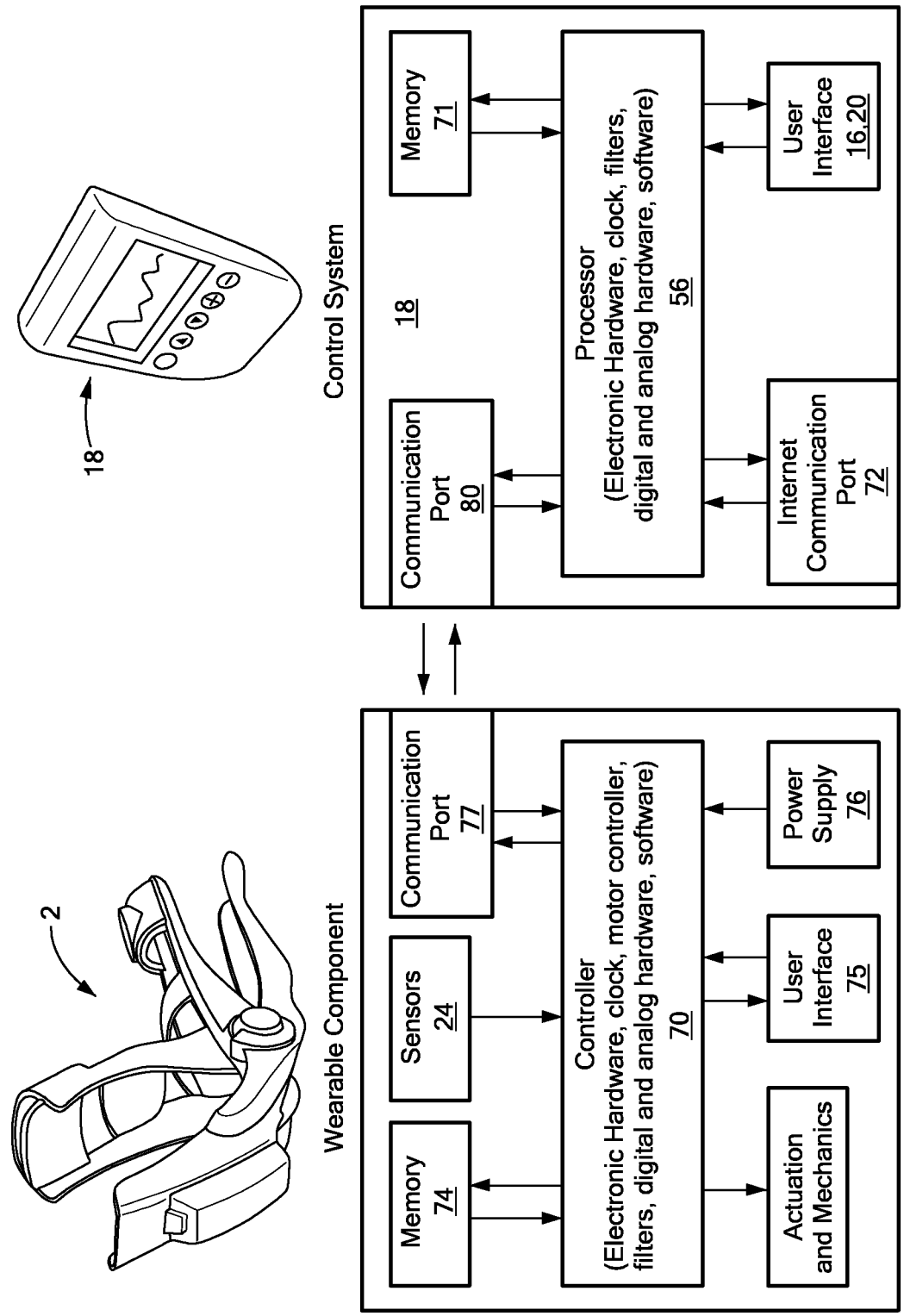
FIG. 39 shows an illustrative embodiment of a functional block diagram of the control functionality of wearable unit 2 and separate control system 18 for an embodiment where wearable unit 2 includes an onboard controller 70.

FIG. 39 shows a block diagram view of the control functionality of the wearable component 2 and the control system 18 for an embodiment in which the wearable component 2 includes an onboard controller 70. In this embodiment, the control system 18 includes a processor 56, user interface with inputs 16 and a display 20, memory 71, communication port 80, which may be wired or wireless, and Internet communication port 72. Sensor(s) 24 on wearable component 2 communicate with processor 56 via a wired or wireless connection. Wearable component 2 includes an onboard controller 70, which may include a user interface 75 with a display, memory 74, and communication port 77. Sensor(s) 24 communicate with the controller 70 via a wired or wireless connection. Onboard controller 70 is connected to, and controls the operation of, the actuation and mechanics functions of wearable component 2. The actuation and mechanics functions include actuator assembly 36, 38, 42, 44, which is coupled to brace sections 32, 34. The wearable component 2 may also include a power supply 76 that may be connected to the controller 70, the sensor(s) 24, the user interface 75 and/or the actuator assembly to power the various elements of the wearable component 2. The power supply 76 may be one battery (e.g., rechargeable battery or one time use battery), connected to all the desired elements, or may be more than one battery separately connected to each of the desired elements.

Table 2 shows an example of the control functionality that may be accessible through a user interface located on the wearable component 2. In this example, the wearable component 2 control functionality is a subset of the device control functionality that is available through the control system 18. Table 3 shows an example of device functionality that may be available through the control system 18. Table 4 shows an example of a device setup and use scenario for a device having a control system 18 and a wearable component 2 with onboard memory, and an onboard user interface. Table 5 shows an example of a control system 18 user interface menu structure. In this example, the menus relate to user login and device calibration prior to entering normal operation mode.

TABLE 2

Brace Control Functionality

Turn Power on/off via UI switch/button/lever/touchscreen
Provide feedback to user:
    EMG signal display
    Battery state information
    Error state information TABLE 2-continued Brace Control Functionality EMG signal connectivity/quality/strength
    Provide range of motion feedback
    Provide quality or speed of motion feedback
    Provide cues for when or how to move
    Provide information regarding operational mode, progress, time, etc.
    Feedback may be audio, visual, tactile
Receive input from user:
    Recalibrate
    Adjust assistance levels
    Self diagnose
    Change operational mode
    Change force parameters
    Change force profiles

TABLE 3

Control System Functionality

Turn Power on/off via UI switch/button/lever/touchscreen
Device setup and help:
    Donning/doffing instructions
    Sensor positioning guidelines
    Calibration instructions
Calibration (Automatic):
    Set EMG offset(s)
    Set default assistance force parameters
    Set filter parameters
Calibration (Manual):
    User adjustment of EMG offsets
    User adjustment of default assistance force parameters
    User adjustment of filter parameters
Display (real time and historical):
    EMG signal activity
    Error states and troubleshooting status and/or instructions
    Battery state information
    Use instructions, Frequently asked questions, context-specific directions
    Data upload/download screens (for connecting to, and exchanging data with the brace unit, the internet, other braces or user interfaces, or other devices
    Games, targets, exercises for guiding movement and/or therapy during use
    Progress measures, progress metrics, outcomes, results of physical tests
    Graphs or other displays of user-specific data: Range of motion, game scores over time, frequency of use, common outcomes measures, quality of motion metrics, etc.
Provide links for exchanging stored data with the brace, other devices, other braces, other user interfaces, computers, and the internet.
Provide a mechanism for remote connection to a therapist via the internet or other remote connection
Provide a means for managing user account (logging in patients and therapists, changing user profiles and default parameters, creating new user accounts, etc)
Provide a link for uploading and downloading data
Receive input from user:
    Touch Screen
    Buttons, switches, levers, capacitive sensors, verbal commands
User adjustments of:
    Device force parameters
    Exercise programs
    Operational mode
    Assistance levels
    Accessibility settings (login capability of different users, passwords set, lockouts)
    Range of motion parameters (e.g., limits)

TABLE 4

Example of a Device Setup and Use Scenario

User (a therapist) turns on user interface (UI)
UI prompts user for login information
Therapist swipes RFID tag, or enters code or name
UI acknowledges therapist and prompts patient for login information
Patient swipes RFID tag, or enters code or name
UI confirms patient's identity
UI provides instruction for patient to put the device on (sensor placement, straps, setup, calibration, etc)

TABLE 4-continued

Example of a Device Setup and Use Scenario

User turns power on brace (as instructed by UI)
UI provides instruction (on screen, or verbal) on how to go through the calibration procedure
UI sets EMG offset value(s), default force parameters, and/or other values during calibration procedure
UI then provides the user with an opportunity to adjust the auto-set values onscreen using the user input device(s) and/or display
User then makes some adjustments onscreen using the input device(s): Assistance levels, operational mode, exercise programs, etc.
UI then begins applying torque to the device according to the user-set and auto-set parameters
During operation, UI display shows real-time EMG data (and past 10 seconds strip chart style display); UI also displays some options/buttons onscreen: "Help", "Restore default settings/parameters", "Recalibrate", "Adjust assistance level(s)", etc.
During use, the user observes EMG values onscreen, and makes adjustments to assistance levels, calibration values as needed, and uses the help menu and restore default features as needed
The brace receives and stores all settings and information regarding parameters from the user interface in real time
At any time, the user can turn off the UI
The brace continues to operate with default (auto-set, or last-saved, for example) parameter values and settings, independently of the UI
User turns brace power off (finished session for the day)
User turns brace power back on (next day) without turning the UI on
When powered on without the UI, the brace operates with default (auto-set, or last-saved, for example parameter values and settings, independently of the UI
User turns UI power back on
Brace continues to operate as it did before the UI was turned on, until parameters are changed via the UI or brace
The UI, on power up, goes back to operational screen showing EMG signal and buttons as described above

TABLE 5

User Interface Sample Menu Screen Walkthrough

"Screen 1: ""Welcome User XXX."""
Option 1: Run device (enter)
"Scenario 1: Patient's first session. Screen says: ""This is your first session"". "
    "Takes user to ""place sensors on bicep and tricep"" screen."
"Scenario 2: Not first session. Place the sensors on the Bicep and tricep. Would you like assistance placing the sensors?"" (click yes or no)"
    Option 1: Yes
        "Next screen: Display of Bicep AND tricep EMG activity. (may have zoom feature). Text ""Watch EMG to see if you got good signal"". 1 option: Click ""Done"" (enter) then go to option2: ""No"" screen (below)."
        "Option 2: No - Screen says ""Put the device on the arm, and turn the power on the brace then click done"". 2 options: ""Back"", and ""Done""."
            "Option 1: ""Back""-takes user back to screen ""Place the sensors on the Bicep and tricep. Would you like assistance placing the sensors?"""
            "Option 2: ""Done"" - (enter)"
        "Next Screen: ""Choose mode of operation: bicep or tricep"". 2 options: ""Bicep"" and ""Tricep"""
Option 1: Bicep (enter)
"Scenario 1: If patient code is recognized, then defaults are set to last values used in the clinic (f/e/c), and device ramps up to those values immediately."
        "Screen during operation: Adjustment assist leve (current value and up/down arrows); AND display EMG activity; AND ""Defaults"" button AND help button."
    "Scenario 2: If patient code is not recognized, then go through auto calibration:"
        "Next screen: hold arm at 90 degrees, relax, and hit OK. (enter) (maybe have a ""skip"" button that takes you straight to man. cal)."
        "Next screen: Manual cal screen: shows EMG activity: ""Relax the arm and move the slider until the resting EMG is between these 2 bars, then hit OK"". (enter)"
        "Next screen: Manual spring setting: ""Hold arm at side and relax. Brace will move your arm slightly. Therapist dial up/down until correct spring value is reached"". (Done)"
        Next screen: Operation screen. Gain is set to FACTORY default (5?) and can be adjusted later. Spring is set to value just set. Brace ramps up to these values.
        "Screen during operation: Gain (current value displayed and up/down arrows); AND display EMG activity; AND "" Defaults"" button AND help button."
            Help button pushed:
                option 1: recalibrate
                    "Next screen: ""Are you sure you want to recalibrate the device?"""
                        Option 1: No
                            Go back to operation screen
                        Option 2: Yes
                            "Next Screen: Back to the auto-cal screen, brace torque ramps off, go through auto-cal, manual cal, manual spring, then ramp on to operation screen."
                option 2: Self-diagnose?
                option 3: Contact info (either clinic phone number? Myomo support?)
                    "Next screen: Display phone numbers/names, etc."
                option 4: Back/Close

TABLE 5-continued

User Interface Sample Menu Screen Walkthrough

```
      Go back to operation screen
    Defaults Button pushed:"
      "Next screen: Big button: ""Restore defaults""; small button ""Set Defaults"".."
        "Option 1: ""Restore defaults"" pushed:"
    "Scenario 1: Recognized user with preset defaults: Displays preset defaults for
    this user and says: ""Are you sure you want to set to these values?"" 2 options:
    ""No"", ""Yes""."
      "Option 1: ""No"" - takes user back to operation screen."
      "Option 2: ""yes"" - sets defaults and goes back to operation (power stays
      on the whole time, RAMP to new values) (3 second pop up that confirms
      new settings)."
    "Scenario 2: Unrecognized user, or user with no preset defaults: Displays
    FACTORY defaults and says: ""Are you sure you want to reset?"". 2 Options:
    ""No"", ""Yes""."
      "Option 1: ""No"" - takes user back to main help menu"
      "Option 2: ""yes"" - sets defaults and goes back to operation screen, and
      ramps to new values (power stays on the whole time)."
      "Option 2: ""Set Defaults"" pushed:"
    "Next screen: Display current value of f/e/c and ask: ""Are you sure you want
    to set these values as the defaults for this user?"". ""Yes"" or ""No""."
      Option 1: Yes - Defaults are set internally.
        "Next screen: ""Defaults have been set to f=x, e=y, c=z for user XX"".
        (this screen lasts for 4 seconds, then returns to operation screen)."
      Option 2: No - Returns to operation screen.
      Option 3: Back/Close
    Next screen: Back to operation screen
  Assist adjustment arrows pushed:
    Up arrow pushed: Value displayed onscreen goes up in real time.
    Down arrow pushed: Value displayed onscreen goes up in real time.
Option 2: Tricep
  "Same as Bicep, but with different training for therapists around how to set spring."
```

Embodiments of the device may also have a data storage and management system which may record and store data from the device. The data storage may be attached to, or inside of, the wearable component 2, or a separate user interface unit, or both. The data storage system may integrate with other standard of care data formats and provide tracking, data-logging and/or synchronizing with other applications and devices e.g., in home automation. In use, the device may measure and store user data during operation. Data may include progress metrics (e.g., range of motion, speed of motion), medical diagnostics (e.g., vital signs, blood pressure, body temperature, sweating, pulse), general data logging (e.g., hours of use) and usage patterns (e.g., when and for how long, device settings). Data may also include power output or consumption of the device, as measured, for example, by current and voltage at the actuator, and estimated power consumption by the user in, for example, calories, as measured by, for example, torque and velocity of the brace about the joint. This information may then be presented to the user and/or clinician to help shape the therapy protocols, dosage, assistance levels, device parameters, sizing, etc. For example, the information may be used to calculate a ratio between the quantitative measurement of device assistance (e.g., measured by the EMG levels going in, Gain, spring, etc.), and a quantitative measurement of patient performance (e.g., elbow range of motion, amount of use of arm based on accelerometer data, average speed of motion, frequency of motion, smoothness of motion, etc.). The information may include a qualitative measurement, e.g., user indicates amount of assistance they are contributing to moving the device. The information may include a combinations of items, such as the amount of external help (e.g., other person assisting), the amount of device help (e.g., gain level of the device, measure torque, or force of the device, etc), and/or the measure of success (e.g., amount of use, range of motion, acceleration, speed, frequency, smoothness, etc.). The system may have the capacity to store (via permanent or temporary memory) many pieces of information (including all those mentioned above) pertaining to the user's progress, frequency and duration of use, parameters of use (e.g., range of motion, velocity/force/torque profiles, selected gains, damping coefficients and system settings), and EMG signal history. This information may be accessed later by the user, caretaker, therapist, physician or other individual who may use the information to track the user's progress, or to adjust system parameters accordingly. Multidimensional measurements may be measured and/or stored, with one or more of the dimensions measured by the device. The information may be recorded manually, or by other means (other devices, add-on components, etc). The information may be used to automatically modify treatment with the Brazilian device, e.g., based on the multidimensional measurements, combinations thereof, and/or relationships therebetween. The information may also include data useful for device diagnostics, such as battery charge and time to charge, and number of on/off cycles.

Embodiments of the device may also include a number of safety mechanisms. The device may be equipped with sensor disconnect sensing. For example, the device may detect when a sensor 24 has lost contact with the skin, based on characteristics of the sensor signal. This algorithm may cause automatic cessation of torque generation if EMG sensor disconnect (decoupling from skin) is detected. The system may then respond in a safe manner, (e.g., by turning off power to the actuator assembly) until sensor contact has been restored. If reconnection is detected, then the cessation is itself discontinued, and the device returns to normal operation, after a time delay.

Embodiments of the device may also be equipped with safe range of motion limits to prevent the possibility of injury by pushing a limb past the body's natural limits. For example, the device may have mechanical limits on the range of motion that may be adjustable by removing and re-inserting a physical stop, such as a screw 40, as shown in FIG. 8. Further, electro-mechanical or opto-electrical sensors (e.g., Hall sensor, optical sensor, potentiometer, laser range finder, switch, button) may be employed to provide feedback to the device regarding the position of the brace in its range of motion. This may enable the device to provide feedback to the user regarding his/her proximity to the end of the range of motion, and may also limit the output signal to the actuator assembly to prevent collisions with the mechanical limits. Certain sensors may provide some gradation of accuracy regarding proximity to the end of the range of motion (e.g., Hall effect sensor), while others may be simply on or off (e.g., switch). The device may also have range of motion limits that are supplied via software. Any combination of these physical or software motion limits may be employed.

Embodiments of the device may also limit the torque provided by the actuator assembly (e.g., for reasons of safety, protecting the user, as a means of protecting the system components from overloading due to excessive torque), by providing a control system that limits the current provided to the actuator assembly (e.g., consequently limiting the torque applied by the actuator assembly). There may be a "soft" limit that does not allow sustained high currents, although it may allow brief high-current spikes. There may also be an accompanying "hard" limit that provides an absolute current limit, which may be a current value above which the actuator assembly will not receive a current input. This allows the system to handle brief periods of high torque, but limits the maximum permissible torque at all times, as well as decreasing the allowable torque at any given time based on a recent history of applied torque.

Embodiments of the device may also protect against having the motor push continually against the limits of the device or the user's physical range of motion limits by providing a system that has sensors near the ends of the physical range of motion which command the control system to stop sending current to the motor (e.g., consequently stopping the motor from applying torque) when the brace is near the ends of its physical range of motion.

The processing system applies various control algorithms to the actuator assembly, and is responsible for the appropriate application, timing, and combination of the different control algorithms. Some of these control algorithms are described in more detail below. The actuator assembly receives its commands from the processing system, and applies torques, forces, velocities, and/or positions to the sections 32, 34 of the brace 7.

FIG. 20 shows an illustrative control algorithm and the variables upon which the algorithm is based that may be used in an asymmetric EMG-controlled device in accordance with embodiments of the present invention. The control output signal is the command that is sent to the actuator assembly. FIG. 20 depicts ways in which the various control output signal relationships may be combined to provide one command signal which commands the actuator assembly. As shown, a simple arithmetic combination may be used (1'), in which the output signals from the various relationships (some of which are shown in FIGS. 21-27 below) are added, subtracted, multiplied, divided, or any combination (linear or non-linear (2')) thereof, to generate the command signal to the actuator assembly. A conditional relationship may be used (3', 4'), in which the algorithm for combining the various output signals is dependent on certain conditions being met. Boolean combinations of such conditional relationships (4') may also be used. Also, any combination of the above mentioned techniques may also be used to combine the various output signals to generate one command signal.

Figure 21:
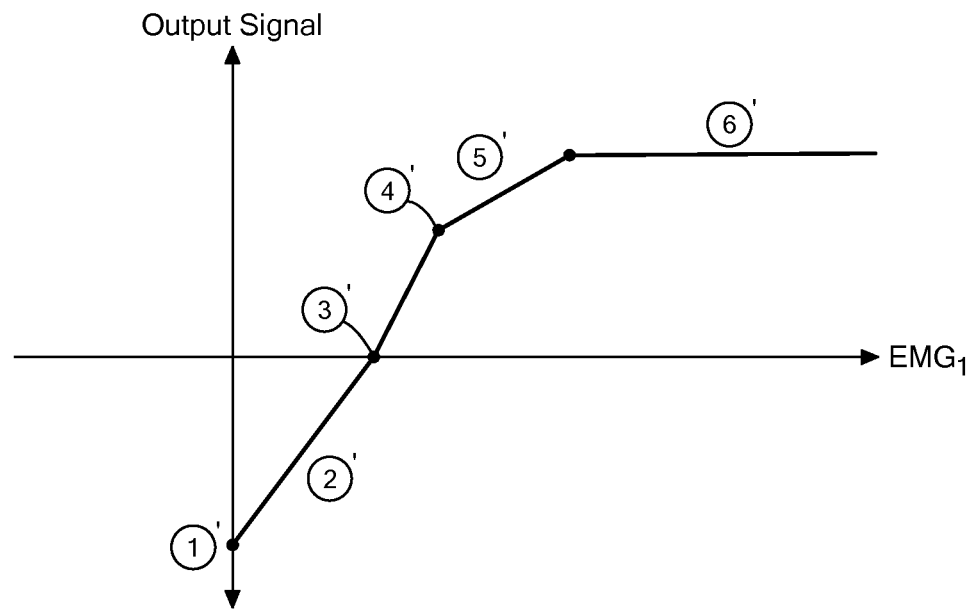
FIG. 21 shows a graph of EMG signal vs. output signal according to illustrative embodiments of the present invention.

FIG. 21 shows a graph depicting features of a control algorithm, namely the relationship between the control output signal and the measured EMG signal from a user's muscle (EMG1). In FIGS. 21-25, the axes have the following meaning: positive output signal correlates to actuator torque, velocity or motion in a first direction about the joint; negative output signal correlates to actuator torque, velocity or motion in a second direction about the joint; and EMG1 is the filtered absolute value of the EMG signal in the first direction. In FIG. 21, the y-intercept (1') is the maximum output signal in the second direction. This is the output signal that the system will give when the value of EMG1 is zero. The correlation between the output signal and EMG1 may be linear or non-linear, and may be considered in two separate regions: the first direction (4', 5', 6'), and the second direction (2'). The zero-crossing point (3') is the value of EMG1 at which the output signal changes direction. There may be break points (4') in any region, at which the slope of the relationship changes, or at which the relationship may change from linear to non-linear. There may be saturation limits (6') where the slope of the relationship goes to zero, meaning the output signal reaches a minimum or maximum "floor" or "ceiling" which it will not surpass, regardless of the value of EMG1. This may serve as a safety mechanism to prevent excessive torques in the case of abnormally high spikes in muscle activity.

Figure 22:
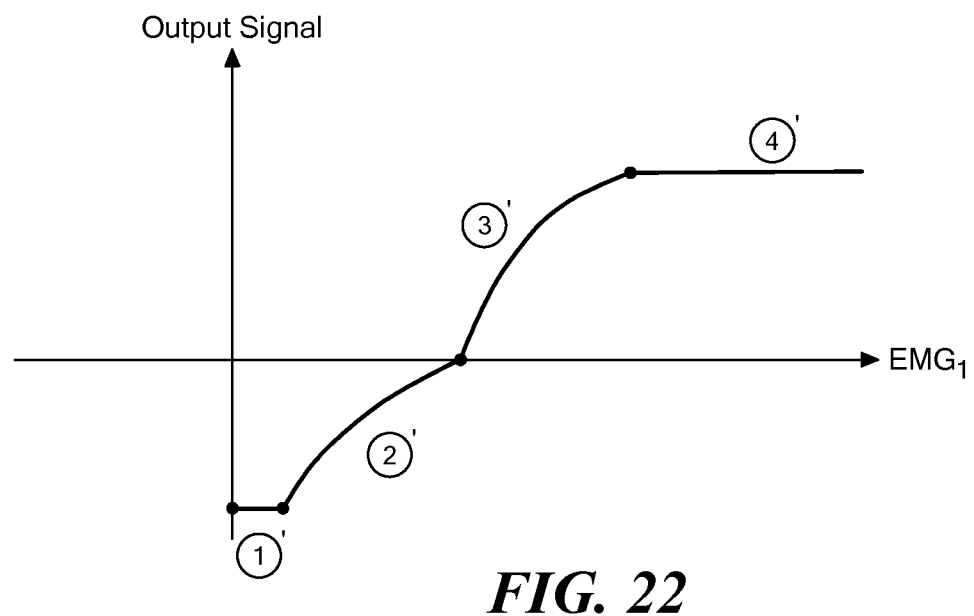
FIG. 22 shows a graph of EMG signal vs. output signal according to illustrative embodiments of the present invention.

FIG. 22 shows a graph depicting features of another control algorithm. In this scenario, there may be output signal saturation in the second direction (1'), as well as in the first direction (4'). FIG. 22 also depicts a non-linear relationship between EMG1 and output signal in both the first (2') and second (3') directions, with a break point coinciding with the zero-crossing.

Figure 23:
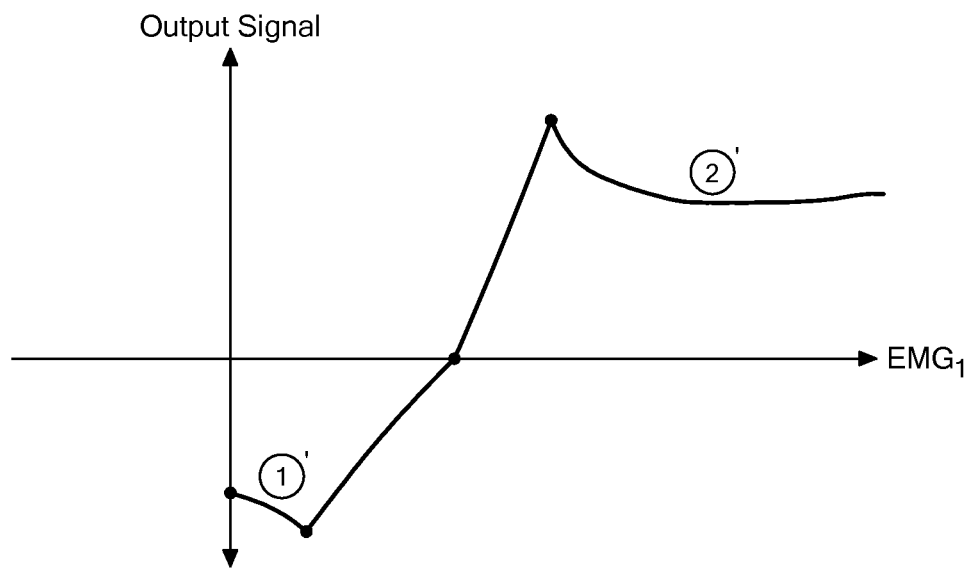
FIG. 23 shows a graph of EMG signal vs. output signal according to illustrative embodiments of the present invention.

FIG. 23 shows a graph depicting features of another control algorithm. As shown, the relationship between output signal and EMG1 is not necessarily monotonic, but may have inflection points, where the slope changes from decreasing to increasing (1'), or vice versa (2'). For example, the maximum absolute output signal value for each direction may be reached before the output signal saturates, or before EMG1 reaches zero.

Figure 24:
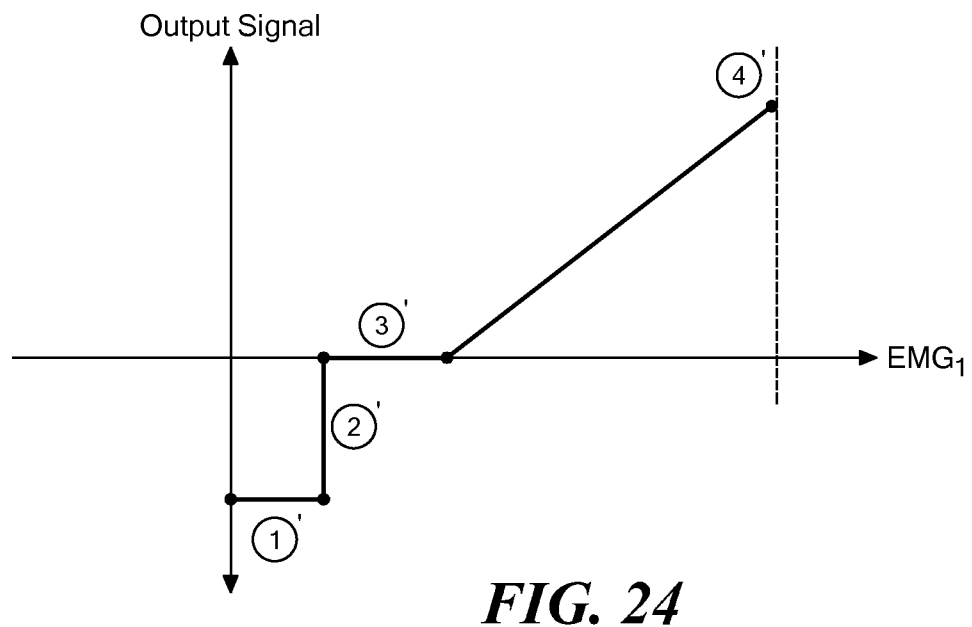
FIG. 24 shows a graph of EMG signal vs. output signal according to illustrative embodiments of the present invention.

FIG. 24 shows a graph depicting features of another control algorithm. As shown, there may be regions of zero slope (1'), regions of infinite slope (2'), or discontinuities (3') in the relationship between output signal and EMG1. For example, the output signal may be constant for low values of EMG1 and then the value may jump to zero at a certain value of EMG1. Also, the output signal may not change direction (and cause torque in the first direction) until the value of EMG1 reaches yet another, higher value. This may be thought of as a "dead band" (3'), which may act to minimize the sensitivity of the output signal to small perturbations in EMG1 about some nominal value.

Figure 25:
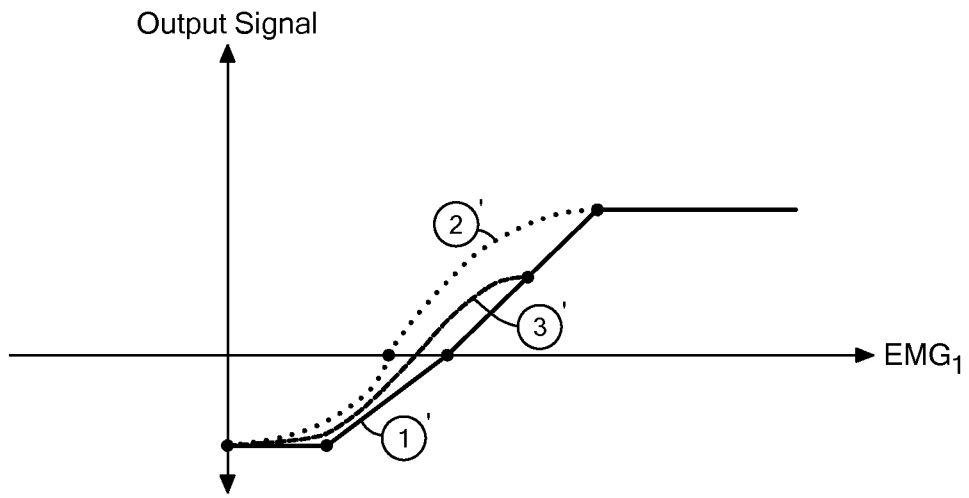
FIG. 25 shows a graph of EMG signal vs. output signal according to illustrative embodiments of the present invention.

FIG. 25 shows a graph depicting features of another control algorithm. As shown, there may be hysteresis in the relationship between output signal and EMG1. The relationship may follow a certain path if EMG1 is increasing, and may follow a different path if EMG1 is decreasing. For example, the output signal may follow curve (1') if EMG1 is increasing, and the output signal may follow curve (2') if EMG1 is decreasing. Alternatively, the output signal may follow a hysteretic path (3') which departs directly from the "EMG1 increasing" or "EMG1 decreasing" curve, when EMG1 changes direction (rather than making a discontinuous jump from one curve to another, as in (2')).

Figure 26:
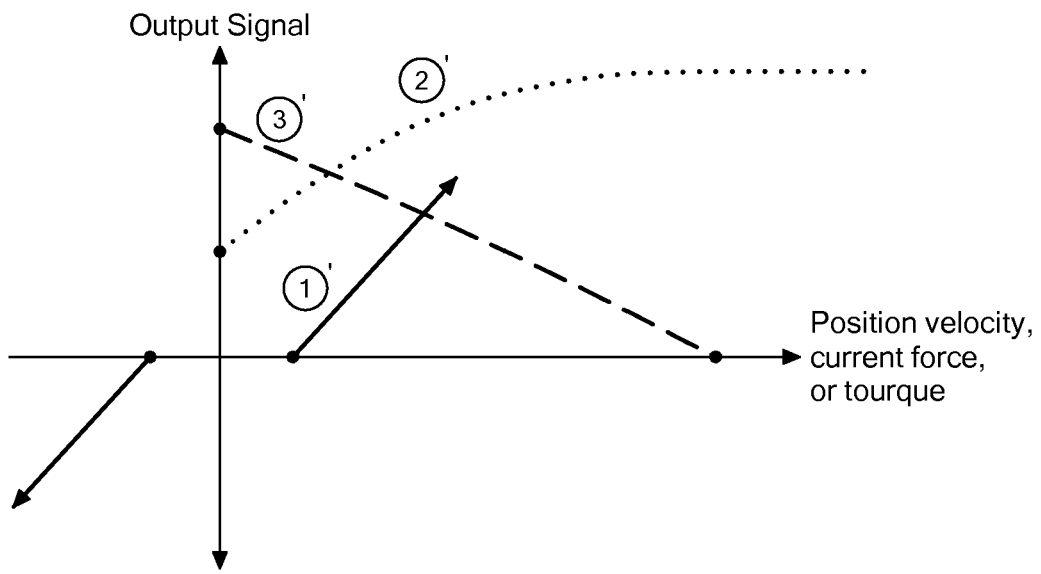
FIG. 26 shows a graph of other parameters vs. output signal according to illustrative embodiments of the present invention.

FIG. 26 shows a graph depicting features of another control algorithm, showing the potential relationship between a control output signal and other measured parameters such as joint position, joint velocity, current and various measured forces or torques. As shown, the relationships may be linear (1') or non-linear (2', 3'), increasing or decreasing (3') or both. The relationship may be continuous or discontinuous (1'), and may have positive and negative components. The relationship may also be asymptotic, and may have saturation limits (2').

Figure 27:
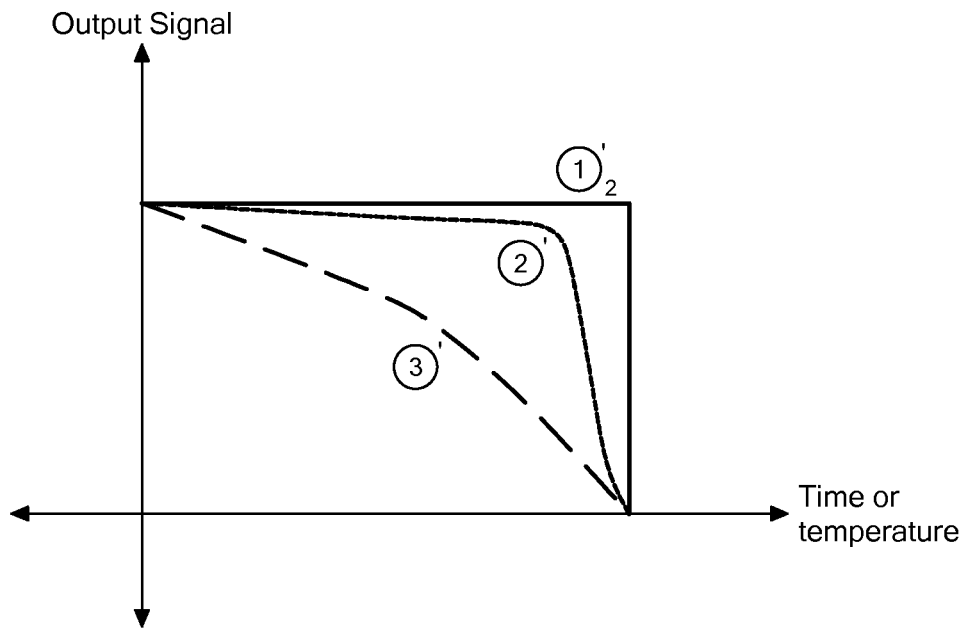
FIG. 27 shows a graph of time or temperature parameters vs. output signal according to illustrative embodiments of the present invention.

FIG. 27 shows a graph depicting features of another control algorithm, showing the potential relationship between a control output signal and other measured or unmeasured parameters such as temperature or time. As shown, the relationship may be linear or non-linear (1', 2', 3'), increasing or decreasing (3') or both. The relationship may be continuous or discontinuous (1'), and may have positive and negative components. The relationship may also be asymptotic, and may have saturation limits (2'). They may have regions of zero slope, and regions of infinite slope (1').

Figure 28:
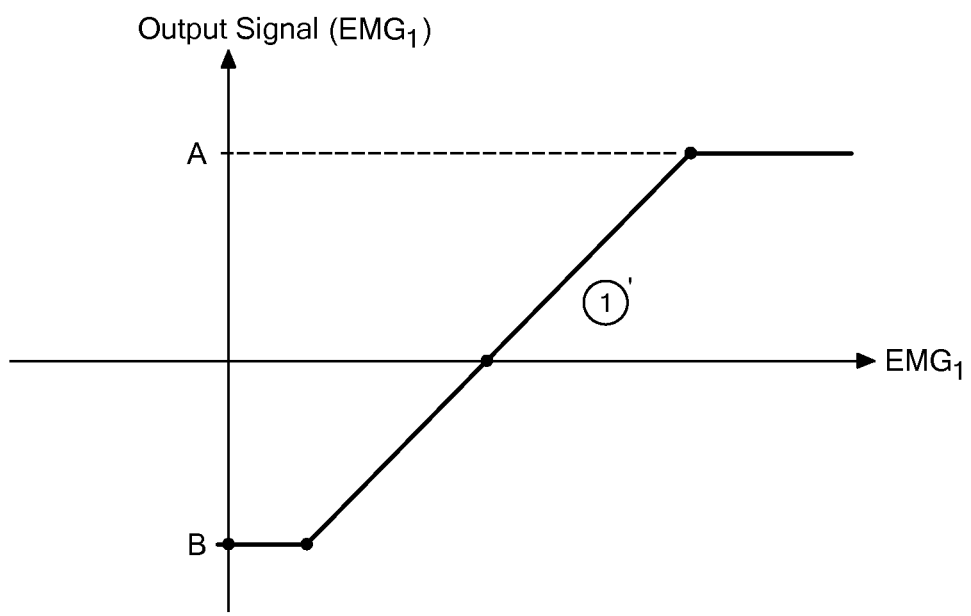
FIG. 28 shows a graph of EMG signal vs. output signal according to illustrative embodiments of the present invention.
Figure 29:
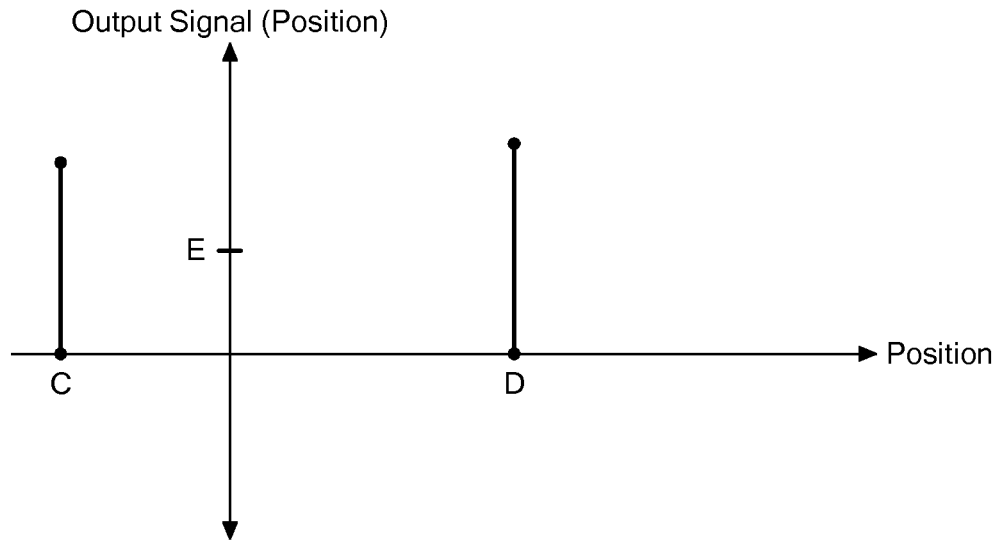
FIG. 29 shows a graph of position vs. output signal according to illustrative embodiments of the present invention.
Figure 30:
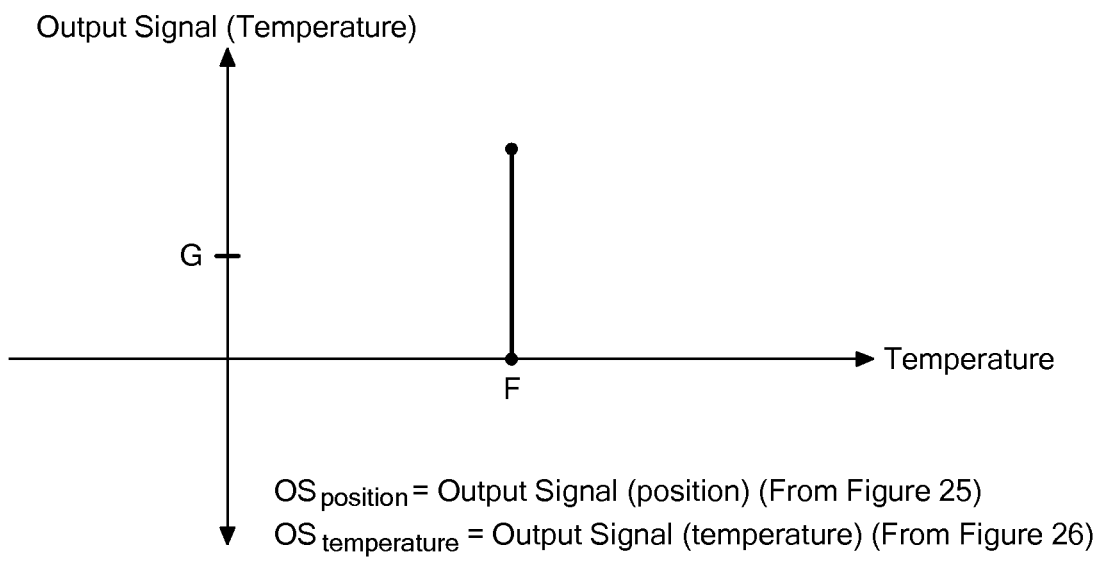
FIG. 30 shows a graph of temperature vs. output signal and a control algorithm according to illustrative embodiments of the present invention.

FIGS. 28-30 show graphs depicting features of an asymmetric control algorithm. The equation for the command output to the actuator assembly is shown in FIG. 30. As shown, the slope of the line (1'), and the values of the constants (A,B,C,D,E,F,G) are adjustable via the user interface.

EXAMPLES

Figure 31:
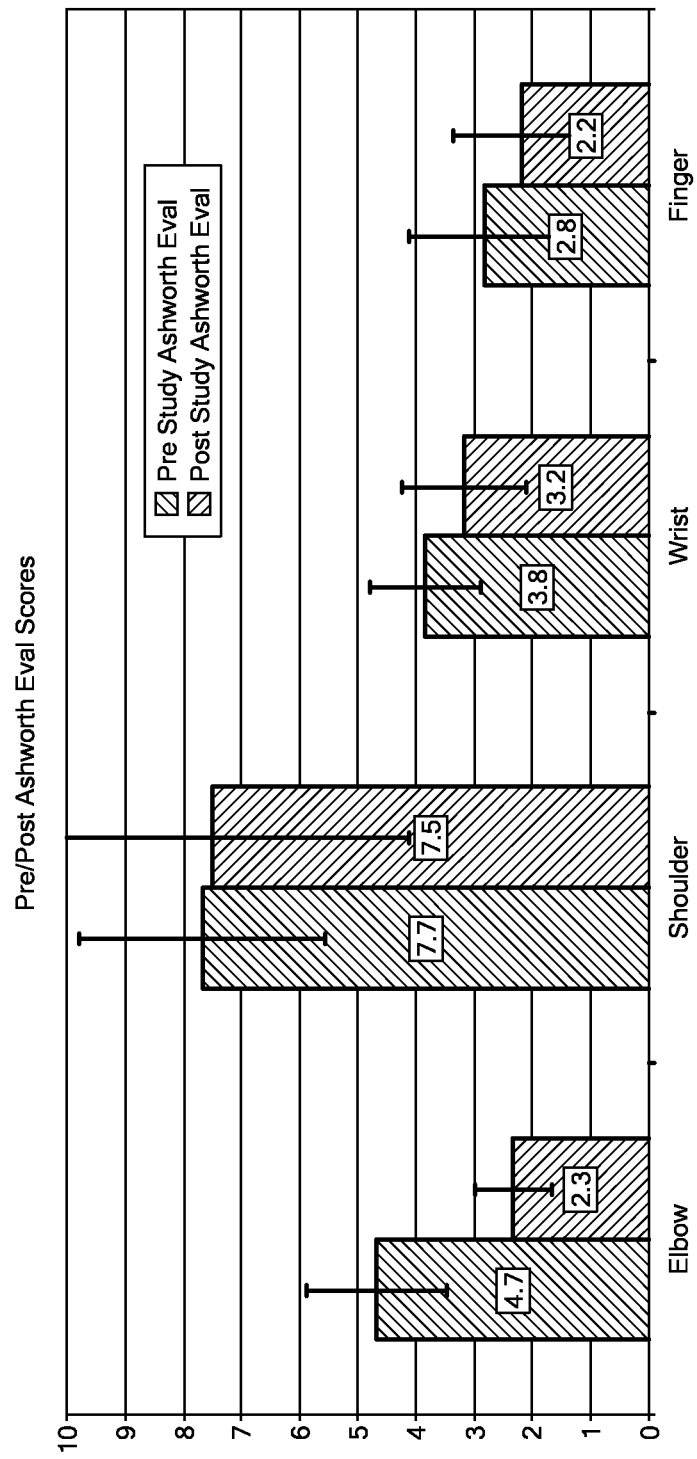
FIG. 31 shows pre and post Ashworth evaluation scores for users of an orthotic device according to illustrative embodiments of the present invention.
Figure 32:
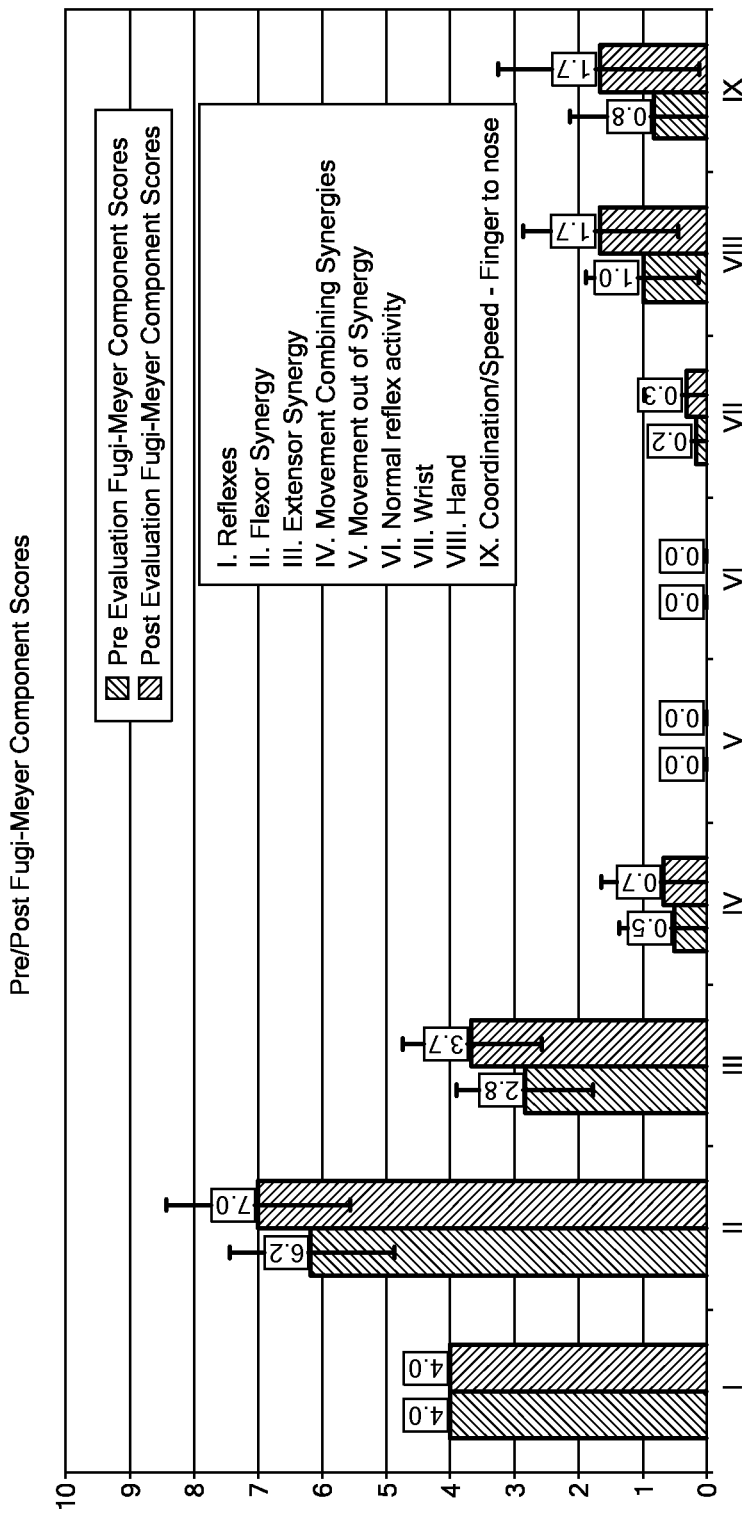
FIG. 32 shows pre-evaluation and post-evaluation Fugl-Meyer Component scores for users of an orthotic device according to illustrative embodiments of the present invention.

An asymmetric EMG-controlled orthotic device in accordance with embodiments described herein was built and used in clinical trials on healthy individuals and on stroke survivors. The control algorithms proved effective in both enabling stroke survivors to control the device, and in promoting rehabilitation of the afflicted joint(s). FIGS. 31 and 32 are graphs showing rehabilitation progress of the subjects in the clinical trial, according to industry-standard rehabilitation scales (Fugl-Meyer and Ashworth).

Embodiments of an EMG-controlled orthotic device may be used in a variety of ways and with various protocols as a rehabilitation or functional aid. For example, rehabilitative exercise regimes may include the execution of familiar and/or functional tasks, or components thereof, to enhance the user's functional capacity. To this end, a subject's functional capabilities may be first assessed and classified into various levels without the device on. For example, three levels of classification that may be used are listed below, although any number of levels having various characteristics may be employed. In addition, although the levels of classification are related to arm motion and related therapies, levels with other characteristics may be used for other parts of the body, e.g., leg, hand/wrist, or foot/ankle. The examples below are thus exemplary.

Level III: Skilled Movement
Goal: use arm to successfully perform functional tasks, integrating all components
Characteristics:
volitional motion of arm, out of synergies
no extra proprioceptive input required to perform motion
able to consistently have volitional alternating flex/extension to perform functional activity
verbal cues to minimal assistance to block abnormal shoulder motions
none or verbal cues for posture required
can perform tasks with better speed, smoothness of alternating from flexion to extension
increased frequency and endurance in therapy
low assistance required during therapy
can perform tasks in multiple planes and diagonals, with functional mobility, and increased challenges to task
Level II: Increased Controlled Motion Relative to Level I
Goal: move joints in available range of flexion and extension to perform functional task components
Characteristics:
consistent volitional motion of bicep and tricep
requires some extra proprioceptive input to perform motion
mixed use of synergies
minimal to moderate assistance required to block abnormal shoulder motion
moderate verbal cues required for posture
can perform tasks slowly, may be 'jerky'
moderate endurance in therapy, can tolerate some increased frequency and repetition of tasks
moderate assistance required during therapy
can perform tasks best in straight planes, seated or standing
Level I: Stability and Mobility
Goals: achieving maximal active range of motion and providing a stable base for movement
Characteristics:
some EMG reading of the bicep and/or tricep
requires extra proprioceptive input to perform motion, may require manual pronation/supination by therapist
little volitional motion of arm out of synergies
unable to consistently fire muscles to perform functional activity
requires moderate to maximal assistance to block abnormal shoulder motion
requires maximal verbal cues for posture
high level of assistance required during therapy
most tasks performed seated or as easiest For example, a subject with very limited capability may have one or more characteristics falling within Level I, a subject with limited capability may have one or more characteristics falling within Level II, and a subject with a more moderate capability may have one or more characteristics falling within Level III. Of course, a subject may have one or more characteristics falling within two levels when the subject's capability is transitioning from one level to the next, e.g., between Level I and Level II or between Level II and Level III.

After assessing the subject's capability without a device in accordance with embodiments herein, various physical tasks may be performed while using or wearing the device. While using the device, the subject typically has characteristics falling within the subject's assessed capability level and may have some characteristics falling within a higher level. For example, if a subject is assessed at Level I without using the device, then the subject may have characteristics falling within Level I and Level II when using the device. The physical tasks may include different categories or types of movements that utilize various aspects of the affected muscles. For example, the physical tasks may include the following categories for a subject with impaired arm functionality:

A. utilize gross bilateral grip to manipulate an object in a functional setting

B. utilize the affected arm to increase volitional unilateral extension for a functional task C. utilize the affected arm to stabilize an object in order to perform a functional task with the unaffected arm D. increase volitional unilateral flexion and release for a functional task Some of the physical tasks that may be utilized for each category and level are listed below. Under some of the physical tasks, the a and b subheadings may include different adaptations of the same task or ways to modify the task to increase/decrease the difficulty of the task.

Category A, Level 3. Bilateral reach, lift, and carry laundry basket/box/crate
 a. add functional mobility
 b. increase weight or size of object used in task
Category A, Level 3. Bilateral reach, manipulate and stack boxes on table
 a. utilize different planes, diagonals, or surface heights
Category A, Level 2. Lift box straight up on table at mid line, bilateral grip
 a. increase repetitions and speed performed
 b. increase weight or size of object used
Category A, Level 2. Push and pull crate or box on table
 a. increase weight or size of object used
Category A, Level 2. Push-pull task with wooden staff or using rolling pin
 a. increase speed in which exercise is performed
 b. standing, leaning back on wall
Category A, Level 2. Modified push up on wall/rhythmic stabilization
 a. increase repetitions and speed performed
Category A, Level 2. Bilateral rowing task with wooden staff (repetitive-bilateral exercise)
 a. increase speed
 b. increase use of shoulder flexion
Category A, Level 2. Bilateral use of arm for towel or clothing folding task
Category A, Level 2. Copy similar motions performed simultaneously by the contralateral arm.
Category A, Level 2. Hold ball with bilateral grip at mid line, flex and extend
 a. focus task on motions outside of synergistic patterns
 b. increase repetitions performed
Category A, Level 1. Hold ball with bilateral grip at mid line
 a. increase amount of time spent to hold static position
Category A, Level 1. Weight bearing through affected arm
 a. increase amount of time spent to hold static position
 b. use EMG reading to assess muscle firing
Category B, Level 3. Unilateral reach to open doorknob with affected arm (same sequence for light switch or drawer)
 a. utilize different planes, diagonals,
 b. increase speed
Category B, Level 3. Unilateral reach to moving target such as balloon
 a. utilize different planes, diagonals, or surface heights
 b. arm resting on large physioball on table to assist with gravity
Category B, Level 2. Unilateral reach to a static target on table
 a. utilize different planes, diagonals, or surface heights
 b. focus task on motions outside of synergistic patterns
Category B, Level 2. Tricep facilitated sit to stand
Category B, Level 1. Unilateral seated bicep curls or tricep extension
 a. focus on partial ranges
 b. closed chain into ball
Category B, Level 1. Volitional firing of tricep muscle
Category B, Level 1. Weight bearing through affected arm
 a. increase amount of time spent to hold static position
 b. use EMG reading to assess muscle firing
Category C, Level 3. Carrying household items with affected arm
 a. utilize different planes, diagonals, or surface heights
 b. reach to pick up jar then stabilize to open
 c. increase weight or size of object Category C, Level 3. Stabilize jar with affected arm to open
 a. add functional mobility
 b. increase weight or size of object
Category C, Level 2. Stabilize household item with affected arm flexed 90 degrees
 a. increase weight or size of object
Category C, Level 1. Hold jar or ball with affected arm, hold for longer periods of time
 a. increase weight or size of object used
Category C, Level 1. Hold paper on table with affected arm in order to write
 a. increase amount of time spent to hold static position
 b. use EMG reading to assess muscle firing
Category D, Level 3. Drinking from a cup (adapted as needed)
Category D, Level 3. Reach to face to shave or reach with hairbrush
Category D, Level 2. Wipe mouth with napkin
Category D, Level 2. Flex arm towards mouth from lap
 a. use EMG reading to assess muscle firing
Category D, Level 1. Unilateral seated bicep curls or tricep extension
 a. focus on partial ranges
Category D, Level 1. Volitional firing of bicep muscle
 a. focus task on motions outside of synergistic patterns
 b. use EMG reading to assess muscle firing Thus, a subject's rehabilitation therapy using embodiments of the device may include one or more physical tasks that fall within these different categories within the subject's assessed level of capability or a higher level. For example, a subject classified at Level 1 without using the device, may attempt to perform one or more of the Category A, B, C and/or D, Level 1 tasks or Category A, B, C and/or D, Level 2 tasks while using the device.

When the subject performs these physical tasks, various metrics may be observed and/or recorded in accordance with embodiments of the present invention. For example, the amount of assistance needed from the device during flexion/extension, the number of repetitions achieved and time required to perform them, amount of physical or motivational assistance required (e.g., verbal cues, minimal, moderate, maximal), and/or quality of motion (e.g., jerky, smooth).

The following is an example of a therapy session:
During the Session
Record which number session for the person
Ask the person:
Any changes in health or medications?
Any changes in the use of your arm at home?
Record subjective quotes
Perform basic warm-up (e.g., about 10 minutes). This may include the following:
 roll shoulders both directions
 shoulder retraction, hold, relax
 neck stretches
 elbow: Passive Range of Motion (PROM), Active Assisted Range of Motion (AAROM), stretching as applicable.
The warm-up time may be used to assess patient tone or which muscles to start with (e.g., bicep/tricep)
Start session in bicep mode—don brace and assess if calibrated well (e.g., 2-5 minutes)
Chose activities by classification level of subject (e.g., 15-20 minutes). This may include the following:
 perform muscle specific activity, e.g., seated bicep curl in isolated ranges
 perform functional components, e.g., have subject try to flex arm and actively relax back down to lap attempt functional task to abilities of subject, e.g., put adapted cup with straw in subject's hand and have them bring the cup to mouth Change to tricep mode and assess if calibrated well (e.g., 2-5 minutes)

Chose activities by classification level of subject (e.g., 15-20 minutes). This may include the following:
- perform muscle specific activity, e.g., seated tricep extension in isolated ranges
- perform functional components, e.g., have subject isometric extension and relax onto ball or leg
- attempt functional task to abilities of subject, e.g., attempt tricep facilitated sit-stand Record all activities in a written report as they are occurring. For example, the report may include the following:
- performed tricep facilitated sit to stand; start time: 10:30 AM stop time: 10:35 AM total time: 00:05 min. Assistance in one direction (gain): 8; assistance in other direction (spring): 2
- moderate physical assistance, able to attempt 5 times with smooth motions In the reports, may use the category "recalibrate to tricep mode" or "set up and calibrate" and specify whether using brace in bicep or tricep mode.

Summarize the Session

Record subjective quotes, record time spent performing each task

Rate the overall assessment of subject's performance. This may be in the form of a checklist.

Note any general recommendations for the next session, e.g., attempt more activities in tricep mode, focus on increasing speed of performance, note techniques that worked/did not work well with the person.

The following may be performed once a week during one of the therapy sessions:

Measure Active Range of Motion (AROM), PROM of elbow flexion/extension pre and post session.

Note changes in sensation reported by subject

Have subject touch hand from left knee to nose 5 times. Record time (and distance if not able to touch nose or chin)

Perform modified Ashworth assessment of arm and hand tone using the following rating system:

0 No increase in muscle tone

1 Slight increase in muscle tone, manifested by a catch and release or by minimal resistance at the end of the range of motion when the affected part(s) is moved in flexion or extension 2 Slight increase in muscle tone, manifested by a catch, followed by minimal resistance throughout the reminder (less than half) of the ROM (range of movement)

3 More marked increase in muscle tone through most of the ROM, but affected part(s) easily moved 4 Considerable increase in muscle tone passive, movement difficult 5 Affected part(s) rigid in flexion or extension Embodiments of an EMG-controlled orthotic device may be used in a variety of ways during a rehabilitation or therapy session or while performing one or more physical tasks. For example, the level of assistance provided by the device may be modified in one or both directions during the execution of a task or repetition (e.g., if certain components of the task are more difficult than others), during the execution of a series of tasks or repetitions, over the course of a therapy session or routine (e.g., as the subject may 'warm up' or fatigue over the course of the session), and/or over a period of time spanned by several therapy sessions, as the subject's level of functionality (and consequent need for assistance) may increase or decrease over such time. For instance, if the subject is having difficulty moving the arm in flexion, but only at the beginning of the motion, then the device may provide additional assistance at first and then provide less assistance during the remainder of the range of motion so that the subject uses his or her muscles more than would otherwise be permitted. If the subject becomes fatigued or tires during the course of a task or series of tasks, then the device may provide increased amounts of assistance over time so that the subject may continue to use the muscles, allowing additional movement training or exercise (e.g., conditioning of the muscles) and increasing the subject's endurance level beyond that which would otherwise be permitted. If the subject's conditioning improves over the course of the therapy or series of tasks, then the device may provide less assistance over time or may increase the level of resistance so that the subject uses his or her muscles more than would otherwise be permitted. If the subject has difficulty in one motion direction, e.g., flexion, but not the other, e.g., extension, then the device may provide additional assistance in one direction compared to the other direction. The increased or decreased amount of assistance provided by the device may be adjusted automatically by the device and/or manually by the user and/or trained individual. The device may be used to temporarily increase the stiffness of a subject's limb, to allow body weight support, body stabilization, or the stabilization of objects in bi-manual tasks (for example, holding a large jar with the affected limb wearing the device, while unscrewing the lid with the unaffected hand/arm).

Adjusting the assistance level of an EMG-controlled orthotic device in accordance with an embodiment of the present invention may improve the quality of motion of a subject's affected limb, by increasing the smoothness, speed, accuracy and strength of its motion. When the device is worn on the affected arm, and physical tasks are performed that require use of both hands or arms, the device may allow the unaffected arm to guide the affected arm through a trajectory to achieve a goal, or may allow the affected arm to achieve the gross motor components of a task (e.g., stabilizing a body or object, holding an object in place, providing a surface against which to push, moving a hand or object through gross trajectories), while the unaffected arm performs the higher dexterity functions (e.g., operations that require dexterous finger motions, finer manipulation of objects, tying shoes, unscrewing lids, grasping objects or handles).

An EMG-controlled orthotic device in accordance with a further embodiment of the present invention may provide feedback to a clinician or user during use, e.g., tactile, visual, audio, or other sensory feedback. This feedback may be real-time or may be stored and displayed at a later time. For example, during a task or a series of tasks, the clinician or user may visually observe the muscle activity occurring through the display 20 on the user interface. The user interface may also provide verbal encouragement and/or visual goals for the user during its use. Visually displaying the EMG activity of one or more of the subject's muscles may heighten the subject's awareness of any unintentional muscle activity, allowing the subject to pay closer attention to the states of the muscles, and to consequently remain focused on the states of the muscles. Thus, the device may train a subject to relax a muscle that may be tight, or may be firing unintentionally (e.g., as a result of high tone, synergistic motion patterns, or lack of inhibitory signals from the brain) when the subject focuses on relaxing the affected muscles that control motion about the joint while the device applies torque to move the limb in a direction that stretches the muscle that is tight or is firing unintentionally.

Although various exemplary embodiments of the invention have been disclosed, it should be apparent to those skilled in the art that various changes and modifications can be made which will achieve some of the advantages of the invention without departing from the true scope of the invention.

What is claimed is:

1. A powered orthotic system comprising:
   a wearable component including:
   a brace having a first section and a second section, the first and second sections coupled to each other at a pivot, the brace configured to be removably attached to a corresponding first and second limb segment of a user such that the pivot is proximate to a joint of the user between each limb segment, the first and the second sections movable with respect to each other to define flexion and extension directions;
   an electromyographic sensor;
   an electrically powered actuator assembly in communication with the electromyographic sensor, the actuator assembly coupled to the first and the second sections so as to apply a force that moves the first and the second sections in the flexion direction, the extension direction, or both, the force based on signals from the electromyographic sensor, wherein the actuator assembly includes a motor in a housing and a drive assembly coupled to the motor, the housing positioned proximate to the pivot; and
   a controller in communication with the actuator assembly that provides system parameters to control operation of the actuator assembly; and
   a control unit in communication with the wearable component, the control unit including:
   a processor that modifies the system parameters in the controller; and
   a user interface, in communication with the processor, that permits user selection of the system parameters, wherein the control unit includes an auto-calibration mode in which an initial electromyographic signal level is measured by the electromyographic sensor for one or more muscles of the user when the muscles are at-rest, and the initial electromyographic signal level is used to adjust an electromyographic signal level measured during subsequent operation of the wearable component.

2. The system of claim 1, wherein the wearable component further includes a user interface, in communication with the controller, that permits user selection of operational modes of the wearable component.

3. The system of claim 2, wherein a single input at the wearable component's user interface causes a plurality of system parameters to be modified in the controller.

4. The system of claim 1, wherein the wearable component further includes a battery coupled to the electrically powered actuator assembly.

5. The system of claim 1, wherein the control unit and the wearable component are in wireless communication with each other.

6. The system of claim 1, further comprising one or more additional wearable components, each additional wearable component in communication with the control unit.

7. The system of claim 6, wherein the control unit and each wearable component are in wireless communication with each other.

8. The system of claim 6, further comprising one or more additional control units, each additional control unit in communication with one or more of the wearable components.

9. The system of claim 1, further comprising one or more additional control units, each additional control unit in communication with the wearable component.

10. The system of claim 1, wherein the wearable component further includes memory, coupled to the controller, that stores the system parameters.

11. The system of claim 1, wherein the control unit is removably attachable to the wearable component.

12. The system of claim 1, wherein the wearable component further includes a plurality of electromyographic sensors.

13. The system of claim 1, wherein the control unit includes an auto-calibration mode in which a user-specific force profile is determined automatically by moving the first section relative to the second section in a desired direction to achieve a desired range of motion of the first limb segment relative to the second limb segment.

14. The system of claim 1, wherein the controller includes a force profile override in order to accept manual adjustment of a user-specific force profile, and the wearable component further includes a user interface, in communication with the controller, for invoking the override and providing manual adjustment of the user-specific force profile.

15. The system of claim 1, wherein the controller includes a limb-lock mode in which the first and the second sections are locked into position relative to one another in response to a user command.

16. The system of claim 15, wherein the user command is a muscle movement that is detected by the sensor.

17. The system of claim 15, wherein the user command is verbal.

18. The system of claim 15, wherein the user command is tactile.

19. An improved electrically powered orthotic device having a brace including first and second sections coupled to each other at a pivot, the brace configured to be removably attached to first and second limb segments of a user, the first and second sections moveable with respect to a joint of the user, wherein the improvement comprises:
   a wearable component including an electric actuator assembly coupled to the brace so as to apply a force for driving the first and second sections about the pivot, a controller in communication with the electric actuator assembly, an electromyographic sensor, and a communication port, wherein the electric actuator assembly includes a motor in a housing and a drive assembly coupled to the motor, the housing positioned proximate to the pivot; and
   a control unit including user interface, a processor coupled to the user interface, a memory, and a communication port, wherein the control unit can be placed in communication with the wearable component, via the communication port of the control unit and the communication port of the wearable component, in order to modify parameters of the controller, wherein the control unit includes an auto-calibration mode in which an initial electromyographic signal level is measured by the electromyographic sensor for one or more muscles of the user when the muscles are at-rest, and the initial electromyographic signal level is used to adjust an electromyographic signal level measured during subsequent operation of the wearable component.

20. The system of claim 15, wherein the housing is coupled to the brace and has a longitudinal axis that is parallel to or perpendicular to an axis of rotation of the joint.

* * * * *

UNITED STATES PATENT AND TRADEMARK OFFICE
CERTIFICATE OF CORRECTION

PATENT NO. : 8,585,620 B2
APPLICATION NO. : 12/406732
DATED : November 19, 2013
INVENTOR(S) : John M. McBean and Kailas N. Narendran Page 1 of 1

It is certified that error appears in the above-identified patent and that said Letters Patent is hereby corrected as shown below:

In the Claims

Column 35, in Claim 1, line 12, replace "segment" with --segments--.

Signed and Sealed this
Twenty-seventh Day of May, 2014

Michelle K. Lee
*Deputy Director of the United States Patent and Trademark Office*